US012053516B2

(12) United States Patent
Arnaud-Barbe et al.

(10) Patent No.: US 12,053,516 B2
(45) Date of Patent: Aug. 6, 2024

(54) MENINGOCOCCAL B RECOMBINANT VACCINE

(71) Applicant: SANOFI PASTEUR INC., Cambridge, MA (US)

(72) Inventors: Nadège Arnaud-Barbe, Paris (FR); Vinod Balhara, Toronto (CA); Raffaella Iantomasi, Paris (FR); Marie-Pierre Kazek-Duret, Paris (FR); Jacqueline McCluskey, Cambridge, MA (US); Laurence Quemeneur, Paris (FR); Bachra Rokbi, Paris (FR); John Shiver, Cambridge, MA (US)

(73) Assignee: SANOFI PASTEUR INC., Swiftwater, PA (US)

(*) Notice: Subject to any disclaimer, the term of this patent is extended or adjusted under 35 U.S.C. 154(b) by 0 days.

(21) Appl. No.: 17/674,932

(22) Filed: Feb. 18, 2022

(65) Prior Publication Data
US 2022/0265805 A1 Aug. 25, 2022

Related U.S. Application Data

(60) Provisional application No. 63/172,885, filed on Apr. 9, 2021.

(30) Foreign Application Priority Data

Feb. 19, 2021 (EP) .................... 21305211

(51) Int. Cl.
A61K 39/095 (2006.01)
A61K 39/00 (2006.01)
(Continued)

(52) U.S. Cl.
CPC ............ *A61K 39/095* (2013.01); *A61K 39/39* (2013.01); *A61P 31/04* (2018.01); *A61P 37/04* (2018.01); *A61K 2039/55505* (2013.01)

(58) Field of Classification Search
CPC .................. A61K 39/095; A61K 39/39; A61K 2039/55505; A61K 2039/70; A61P 31/04; A61P 37/04; C12R 2001/36
See application file for complete search history.

(56) References Cited

U.S. PATENT DOCUMENTS 4,695,624 A 9/1987 Marburg et al.
5,494,808 A 2/1996 Fu
(Continued)

FOREIGN PATENT DOCUMENTS

AU 2016273825 A1 1/2017
EP 0689454 A1 1/1996
(Continued)

OTHER PUBLICATIONS

Rossi et al. Infection and Immunity vol. 84, issue 6, pp. 1735-1742, 2016 (Year: 2016).*

(Continued)

Primary Examiner — Jana A Hines
(74) Attorney, Agent, or Firm — LATHROP GPM LLP; James H. Velema, Esq.

(57) ABSTRACT

The present disclosure relates to an immunogenic composition comprising a combination of meningococcal antigens which comprises at least one factor H binding protein (fHBP) A protein, at least one fHBP B protein, at least one *Neisseria* adhesin A (NadA) protein, and at least one detergent-extracted Outer Membrane Vesicle (dOMV). The meningococcal antigens may be from a *Neisseria meningitidis* serogroup B. The combination of antigens provided a broad coverage of bacteria strains. Further, the present disclosure relates to the use of the immunogenic composition in methods for eliciting an immune response.

15 Claims, 16 Drawing Sheets
Specification includes a Sequence Listing.

(51) Int. Cl.
    A61K 39/39      (2006.01)
    A61P 31/04      (2006.01)
    A61P 37/04      (2006.01)

(56) References Cited

U.S. PATENT DOCUMENTS

| | | | |
|---|---|---|---|
| 9,724,402 B2 | 8/2017 | Anderson et al. | |
| 10,300,122 B2 | 5/2019 | Zlotnick et al. | |
| 10,625,025 B2 | 4/2020 | Ogawa | |
| 10,695,505 B2 | 6/2020 | Ettlin | |
| 11,077,180 B2 | 8/2021 | Anderson et al. | |
| 2013/0011429 A1* | 1/2013 | Poolman | C07K 14/22 424/192.1 |
| 2013/0189295 A1* | 7/2013 | Aric | A61K 39/39 424/190.1 |
| 2017/0173140 A1 | 6/2017 | Zlotnick et al. | |
| 2017/0183384 A1 | 6/2017 | Beernink | |

FOREIGN PATENT DOCUMENTS

| | | |
|---|---|---|
| EP | 0735898 A1 | 10/1996 |
| EP | 0761231 A1 | 3/1997 |
| EP | 0835318 A2 | 4/1998 |
| WO | WO 1990/014837 A1 | 12/1990 |
| WO | WO 1994/021292 A1 | 9/1994 |
| WO | WO 1995/017210 A1 | 6/1995 |
| WO | WO 1997/001640 A2 | 1/1997 |
| WO | WO 1998/052581 A1 | 11/1998 |
| WO | WO 1998/057659 A1 | 12/1998 |
| WO | WO 1999/011241 A1 | 3/1999 |
| WO | WO 1999/044636 A2 | 9/1999 |
| WO | WO 1999/052549 A2 | 10/1999 |
| WO | WO 2000/007621 A2 | 2/2000 |
| WO | WO 2000/023105 A2 | 4/2000 |
| WO | WO 2000/056358 A2 | 9/2000 |
| WO | WO 2000/062800 A2 | 10/2000 |
| WO | WO 2001/021152 A1 | 3/2001 |
| WO | WO 2001/021207 A2 | 3/2001 |
| WO | WO 2001/064920 A2 | 9/2001 |
| WO | WO 2001/064922 A2 | 9/2001 |
| WO | WO 2002/058737 A2 | 8/2002 |
| WO | WO 2003/020756 A2 | 3/2003 |
| WO | WO 2009/109550 A1 | 9/2009 |
| WO | WO 2010/046715 A1 | 4/2010 |
| WO | WO 2011/051893 A1 | 5/2011 |
| WO | WO 2011/126863 A1 | 10/2011 |
| WO | WO 2013/046855 A1 | 4/2013 |
| WO | WO 2015/017817 A1 | 2/2015 |
| WO | WO 2015/128480 A1 | 9/2015 |
| WO | WO 2016/008960 A1 | 1/2016 |
| WO | WO 2016/014719 A1 | 1/2016 |
| WO | WO 2018/045286 A1 | 3/2018 |
| WO | WO 2020/030782 A1 | 2/2020 |
| WO | WO 2020/165711 A1 | 8/2020 |

OTHER PUBLICATIONS

Murphy et al. Journal of Infectious Diseases vol. 200, pp. 379-389, 2009. (Year: 2009).*
Atkinson et al., "History of Meningococcal Outbreaks in the United States: Implications for Vaccination and Disease Prevention", Pharmacotherapy, 2016, 36(8): 880-892.
Bambini et al., "Distribution and genetic variability of three vaccine components in a panel of strains representative of the diversity of serogroup B meningococcus", Vaccine, 2009, 27(21): 2794-2803.
Batista et al., "Meningococcal disease, a clinical and epidemiological review", Asian Pac J Trop Med., 2017, 10(11): 1019-1029.
Bijlsma et al., "A decade of herd protection after introduction of meningococcal serogroup C conjugate vaccination", Clin Infect Dis., 2014, 59(9): 1216-1221.
Borrow et al., "Meningococcal surrogates of protection—serum bactericidal antibody activity", Vaccine, 2005, 23(17-18): 2222-2227.
Borrow et al., "Neisseria meningitidis group B correlates of protection and assay standardization—International Meeting Report Emory University, Atlanta, Georgia, United States, Mar. 16-17, 2005", Vaccine, 2006, 24(24): 5093-5107.
Borrow et al., "The Global Meningococcal Initiative: global epidemiology, the impact of vaccines on meningococcal disease and the importance of herd protection", Expert Rev Vaccines, 2017, 16(4): 313-328.
Bruce et al., "Risk factors for meningococcal disease in college students", JAMA, 2001, 286(6): 688-693.
Brunelli et al., "Influence of sequence variability on bactericidal activity sera induced by Factor H binding protein variant 1.1", Vaccine, 2011, 29(5): 1072-1081.
Campsall et al., "Severe meningococcal infection: a review of epidemiology, diagnosis, and management", Crit Care Clin., 2013, 29(3): 393-409.
Capecchi et al., "Neisseria meningitides NadA is a new invasin which promotes bacterial adhesion to and penetration into human epithelial cells", Mol. Microbiol., 2005, 55: 687-698.
Caron et al., "From tailor-made to ready-to-wear meningococcal B vaccines: longitudinal study of a clonal meningococcal B outbreak", Lancet Infect Dis., 2011, 11(6): 455-463.
Chang, "Distribution of Neisseria meningitidis serogroup b (NmB) vaccine antigens in meningococcal disease causing isolates in the United States during 2009-2014, prior to NmB vaccine licensure", J Infect., 2019, S0163-4453(19): 30272-30275.
Christensen et al., "Meningococcal carriage by age: a systematic review and meta-analysis", Lancet Infect Dis., 2010, 10(12): 853-861.
Costa et al., "Human factor H (FH) impairs protective meningococcal anti-FHbp antibody responses and the antibodies enhance FH binding", mBio, 2014, 5(5): e01625-14.
Dyet et al., "Clonal analysis of the serogroup B meningococci causing New Zealand's epidemic", Epidemiol Infect., 2006, 134(2): 377-383.
Einhorn et al., "Immunogenicity in infants of Haemophilus influenzae type B polysaccharide in a conjugate vaccine with Neisseria meningitidis outer-membrane protein", Lancet, 1986, 2(8502): 299-302.
Extended European Search Report for European Patent Application No. 21305211.1, dated Aug. 12, 2021.
Folaranmi et al., "Centers for Disease C. Use of Serogroup B Meningococcal Vaccines in Persons Aged >/=10 Years at Increased Risk for Serogroup B Meningococcal Disease: Recommendations of the Advisory Committee on Immunization Practices", MMWR Morb Mortal Wkly Rep., 2015, 64(22): 608-612.
Frasch et al., "Bactericidal antibody is the immunologic surrogate of protection against meningococcal disease", Vaccine, 2009, 27(Suppl 2): B112-116.
Fredriksen et al., "Production, characterization and control of MenB-vaccine "Folkehelsa": an outer membrane vesicle vaccine against group B meningococcal disease", NIPH Ann., 1991, 14(2): 67-79, discussion—80.
Fu et al. "Recent advances in the large scale fermentation of Neisseria meningitidis group B for the production of an outer membrane protein complex", Biotechnology, Feb. 1995, 13(2): 170-174.
GenBank accession No. AAF42321.1, "Putative adhesin/invasin [Neisseria meningitidis MC58]", Jan. 31, 2014, (GI:7227256), obtained from url: <https://www.ncbi.nlm.nih.gov/protein/7227256>.
Germinario et al., « Young-adult carriers of Neisseria meningitidis in Puglia (Italy): will the pattern of circulating meningococci change following the introduction of meningococcal serogroup C conjugate vaccines?, Hum Vaccin., 2010, 6(12): 1025-1027.
Goldschneider et al., "Human immunity to the meningococcus. I. The role of humoral antibodies", J. Exp. Med., 1969, 129: 1307-1326.
Gorringe et al., "Bexsero—A Multicomponent Vaccine for Prevention of Meningococcal Disease", Human Vaccines & Immunotherapeutics, Feb. 2012, 8(2): 174-183.

(56) References Cited

OTHER PUBLICATIONS

Granoff et al., "Does binding of complement factor H to the meningococcal vaccine antigen, factor H binding protein, decrease protective serum antibody responses?", Clin Vaccine Immunol., 2013, 20(8): 1099-1107.
Grodet et al., "Outbreak in France of Neisseria meningitidis B:15:P1. 12 belonging to sequence type 1403", Microbiol Infect., 2004, 10(9): 845-848.
Harrison et al., "Description and nomenclature of Neisseria meningitidis capsule locus", Emerg Infect Dis., 2013, 19(4): 566-573.
Harrison et al., "Meningococcal capsular group A, C, W, and Y conjugate vaccines", Plotkin's Vaccines ($7^{th}$ Ed.), 2018, 7: 619-643. e11.
Helting et al., "Serotype determinant protein of Neisseria Meningitidis. Large scale preparation by direct detergent treatment of the bacterial cells", Acta Pathol Microbiol Scand C., Apr. 1981, 89(2): 69-78.
Higbee et al., "An immunologic model for rapid vaccine assessment—a clinical trial in a test tube", Altern Lab Anim., Sep. 2009, 37(Suppl 1): 19-27.
International Search Report and Written Opinion for PCT International Patent Application No. PCT/US2022/016894, dated May 13, 2022.
Kvalsvig et al., "The immunopathogenesis of meningococcal disease", J Clin Pathol., 2003, 56(6): 417-422.
Lucidarme, "Characterization of fHBP, nhba (gna2132), nadA, porA, and sequence type in group B meningococcal case isolates collected in England and Wales during Jan. 2008 and potential coverage of an investigational group B meningococcal vaccine", Clin Vaccine Immunol., 2010, 17(6): 919-929.
Luna et al., "Evaluation of the innate immunostimulatory potential of originator and non-originator copies of insulin glargine in an in vitro human immune model", PloS One, Jun. 6, 2018, 13(6): e0197478.
Ma et al., "Assessing the immunopotency of Toll-like receptor agonists in an in vitro tissue-engineered immunological model", Immunology, 2010, 130: 374-387.
Maclennan et al., "Social behavior and meningococcal carriage in British teenagers", Emerg Infect Dis., 2006, 12(6): 950-957.
Maiden et al., "Impact of meningococcal serogroup C conjugate vaccines on carriage and herd immunity", J Infect Dis., 2008, 197(5): 737-743.
Marshall et al., "Safety and immunogenicity of a meningococcal B bivalent rLP2086 vaccine in healthy toddlers aged 18-36 months: a phase 1 randomized-controlled clinical trial", Pediatr Infect Dis J., 2012, 31(10): 1061-1068.
Martin et al., "New Zealand epidemic of meningococcal disease identified by a strain with phenotype B:4:P1.4", J Infect Dis., 1998, 177(2): 497-500.
Martinon-Torres et al., "A randomized, phase 1/2 trial of the safety, tolerability, and immunogenicity of bivalent rLP2086 meningococcal B vaccine in healthy infants", Vaccine, 2014, 32(40): 5206-5211.
McNeil et al., "Role of factor H binding protein in Neisseria meningitidis virulence and its potential as a vaccine candidate to broadly protect against meningococcal disease", MMBR, 2013, 77(2): 234-252.
Meri et al., "Microbial complement inhibitors as vaccines", Vaccine, 2008, 26(Suppl 8): I113-I117.
Moro et al., "Adverse events following Haemophilus influenzae type b vaccines in the Vaccine Adverse Event Reporting System", The Journal of Pediatrics, 2015, 166(4): 992-997.
Murphy et al., "Sequence diversity of the factor H binding protein vaccine candidate in epidemiologically relevant strains of serogroup B Neisseria meningitidis", The Journal of Infectious Diseases, 2009, 200(3): 379-389.
Pace et al., "Meningococcal disease: clinical presentation and sequelae", Vaccine, 2012, 30(Suppl 2): B3-B9.
Pagotto et al., "Stable shuttle vectors for Neisseria gonorrhoeae, *Haemophilus* spp. and other bacteria based on a single origin of replication", Gene, 2000, 244: 13-19.
Pizza et al., "Identification of vaccine candidates against serogroup B meningococcus by whole-genome sequencing", Science, 2000, 287(5459): 1816-1820.
Pollard, "Global epidemiology of meningococcal disease and vaccine efficacy", Pediatr Infect Dis J., 2004, 23(12 Suppl): S274-S279.
Rodriguez et al., "The epidemiological impact of antimeningococcal B vaccination in Cuba", Mem Inst Oswaldo Cruz, 1999, 94(4): 433-440.
Rouphael et al., "Neisseria meningitidis: biology, microbiology, and epidemiology", Methods Mol Biol., 2012, 799: 1-20.
Seib et al., "Neisseria meningitidis factor H-binding protein fHBP: a key virulence factor and vaccine antigen", Expert Rev Vaccines, 2015, 14(6): 841-859.
Stephens et al., "Neisseria meningitidis: biology, microbiology, and epidemiology", Methods Mol Biol., 2012, 799: 1-20.
Stephens et al., "Neisseria meningitidis", ed. Bennett et al., Elsevier Saunders; 2015, pp. 2425-2445.
Stephens, "Biology and pathogenesis of the evolutionarily successful, obligate human bacterium Neisseria meningitidis", Vaccine, 2009, 27(Suppl 2): B71-B77.
Syed, "DTaP5-HB-IPV-Hib Vaccine (Vaxelis(®)): A Review of its Use in Primary and Booster Vaccination", Paediatric Drugs, 2017, 19(1): 69-80.
Trotter et al., "Effectiveness of meningococcal serogroup C conjugate vaccine 4 years after introduction", Lancet, 2004, 364(9431): 365-367.
Vu et al., "Cooperative serum bactericidal activity between human antibodies to meningococcal factor H binding protein and neisserial heparin binding antigen", Vaccine, 2011, 29(10): 1968-1973.
Vuocolo et al., "Vaccination strategies for the prevention of meningococcal disease", Hum Vaccin Immunother., 2018, 14(5): 1203-1215.
Wang et al., "Prevalence and genetic diversity of candidate vaccine antigens among invasive Neisseria meningitidis isolates in the United States", Vaccine, 2011, 29(29-30): 4739-4744.
Watson et al., "Clinical Experience with the Meningococcal B Vaccine, Bexsero®: Prospects for Reducing the Burden of Meningococcal Serogroup B Disease", Vaccine, 2016, 34: 875-880.
Findlow et al., "Broad vaccine protection against meningitidis using factor H binding protein", Vaccine, 2020, 38: 7716-7727.
Pairwise Sequence Alignment, EMBOSS Needle, Aligned Sequence 1: SEQIDNO1, Aligned Sequence 2: Q6VRX9NEIME, Matrix: EBLOSUM62, Mar. 28, 2023, https://www.ebi.ac.uk/Tools/psa/emboss_needle/.
UNIPROT, Q6VRX9_NEIME, Factor H binding protein variant B29_001, Jul. 5, 2004, Retrieved from url: https://www.uniprot.org/uniprotkb/Q6VRY4/entry.

* cited by examiner

SEQUENCE LISTING

```
<160> NUMBER OF SEQ ID NOS: 7

<210> SEQ ID NO 1
<211> LENGTH: 261
<212> TYPE: PRT
<213> ORGANISM: Neisseria meningitidis serogroup B
```

-continued

```
<220> FEATURE:
<223> OTHER INFORMATION: fHbp A05

<400> SEQUENCE: 1

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260

<210> SEQ ID NO 2
<211> LENGTH: 261
<212> TYPE: PRT
<213> ORGANISM: Neisseria meningitidis serogroup B
<220> FEATURE:
<223> OTHER INFORMATION: fHbp A05tmN

<400> SEQUENCE: 2

Cys Ser Ser Gly Ser Gly Ser Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
            35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
```

```
                65                  70                  75                  80
Ser Arg Phe Asp Phe Val Gln Lys Ile Glu Val Asp Gly Gln Thr Ile
                        85                  90                  95

Thr Leu Ala Ser Gly Glu Phe Gln Ile Tyr Lys Gln Asp His Ser Ala
                100                 105                 110

Val Val Ala Leu Gln Ile Glu Lys Ile Asn Asn Pro Asp Lys Ile Asp
                115                 120                 125

Ser Leu Ile Asn Gln Arg Ser Phe Arg Val Ser Asp Leu Gly Gly Glu
                130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
                180                 185                 190

Pro Glu Gln Asn Val Glu Leu Ala Ser Ala Glu Leu Lys Ala Asp Glu
                195                 200                 205

Lys Ser His Ala Val Ile Leu Gly Asp Thr Arg Tyr Gly Ser Glu Glu
                210                 215                 220

Lys Ser Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
                260

<210> SEQ ID NO 3
<211> LENGTH: 260
<212> TYPE: PRT
<213> ORGANISM: Neisseria meningitidis serogroup B
<220> FEATURE:
<223> OTHER INFORMATION: fHbp B01

<400> SEQUENCE: 3

Cys Ser Ser Gly Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
                20                  25                  30

Asp Lys Gly Leu Lys Ser Leu Thr Leu Glu Asp Ser Ile Ser Gln Asn
                35                  40                  45

Gly Thr Leu Thr Leu Ser Ala Gln Gly Ala Glu Lys Thr Tyr Gly Asn
                50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
                100                 105                 110

Ala Leu Gln Thr Glu Gln Glu Gln Asp Pro Glu His Ser Glu Lys Met
                115                 120                 125

Val Ala Lys Arg Arg Phe Arg Ile Gly Asp Ile Ala Gly Glu His Thr
                130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
```

```
                                165                 170                 175
Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
            210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
            245                 250                 255

Ala Ala Lys Gln
            260

<210> SEQ ID NO 4
<211> LENGTH: 260
<212> TYPE: PRT
<213> ORGANISM: Neisseria meningitidis serogroup B
<220> FEATURE:
<223> OTHER INFORMATION: fHbp B01smN

<400> SEQUENCE: 4

Cys Ser Ser Gly Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
    130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
            195                 200                 205

His His Ala Val Ile Ser Gly Ser Val Leu Tyr Asn Gln Asp Glu Lys
        210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His Leu Ile Gly Leu
                245                 250                 255

Ala Ala Lys Gln
```

<210> SEQ ID NO 5
<211> LENGTH: 284
<212> TYPE: PRT
<213> ORGANISM: Neisseria meningitidis serogroup B
<220> FEATURE:
<223> OTHER INFORMATION: NadA1 C-terminally truncated

<400> SEQUENCE: 5

```
Met Thr Ser Asp Asp Val Lys Lys Ala Ala Thr Val Ala Ile Val
1               5                   10                  15

Ala Ala Tyr Asn Asn Gly Gln Glu Ile Asn Gly Phe Lys Ala Gly Glu
                20                  25                  30

Thr Ile Tyr Asp Ile Gly Glu Asp Gly Thr Ile Thr Gln Lys Asp Ala
            35                  40                  45

Thr Ala Ala Asp Val Glu Ala Asp Asp Phe Lys Gly Leu Gly Leu Lys
        50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Glu Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Ala Asp Ile Ala Lys Asn Ser Ala Arg Ile Asp Ser Leu Asp Lys Asn
                245                 250                 255

Val Ala Asn Leu Arg Lys Glu Thr Arg Gln Gly Leu Ala Glu Gln Ala
            260                 265                 270

Ala Leu Ser Gly Leu Phe Gln Pro Tyr Asn Val Gly
        275                 280
```

<210> SEQ ID NO 6
<211> LENGTH: 255
<212> TYPE: PRT
<213> ORGANISM: Neisseria meningitidis serogroup B
<220> FEATURE:
<223> OTHER INFORMATION: fHbp B24

<400> SEQUENCE: 6

```
Cys Ser Ser Gly Gly Gly Gly Val Ala Ala Asp Ile Gly Ala Gly Leu
1               5                   10                  15
```

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 7
<211> LENGTH: 362
<212> TYPE: PRT
<213> ORGANISM: Neisseria meningitidis serogroup B
<220> FEATURE:
<223> OTHER INFORMATION: NadA1

<400> SEQUENCE: 7

Met Lys His Phe Pro Ser Lys Val Leu Thr Thr Ala Ile Leu Ala Thr
1               5                   10                  15

Phe Cys Ser Gly Ala Leu Ala Ala Thr Ser Asp Asp Asp Val Lys Lys
            20                  25                  30

Ala Ala Thr Val Ala Ile Val Ala Ala Tyr Asn Asn Gly Gln Glu Ile
        35                  40                  45

Asn Gly Phe Lys Ala Gly Glu Thr Ile Tyr Asp Ile Gly Glu Asp Gly
    50                  55                  60

Thr Ile Thr Gln Lys Asp Ala Thr Ala Ala Asp Val Glu Ala Asp Asp
65                  70                  75                  80

Phe Lys Gly Leu Gly Leu Lys Lys Val Val Thr Asn Leu Thr Lys Thr
                85                  90                  95

Val Asn Glu Asn Lys Gln Asn Val Asp Ala Lys Val Lys Ala Ala Glu
            100                 105                 110

Ser Glu Ile Glu Lys Leu Thr Thr Lys Leu Ala Asp Thr Asp Ala Ala
        115                 120                 125

```
Leu Ala Asp Thr Asp Ala Ala Leu Asp Glu Thr Thr Asn Ala Leu Asn
    130                 135                 140
Lys Leu Gly Glu Asn Ile Thr Thr Phe Ala Glu Glu Thr Lys Thr Asn
145                 150                 155                 160
Ile Val Lys Ile Asp Glu Lys Leu Glu Ala Val Ala Asp Thr Val Asp
                165                 170                 175
Lys His Ala Glu Ala Phe Asn Asp Ile Ala Asp Ser Leu Asp Glu Thr
                180                 185                 190
Asn Thr Lys Ala Asp Glu Ala Val Lys Thr Ala Asn Glu Ala Lys Gln
            195                 200                 205
Thr Ala Glu Glu Thr Lys Gln Asn Val Asp Ala Lys Val Lys Ala Ala
    210                 215                 220
Glu Thr Ala Ala Gly Lys Ala Glu Ala Ala Ala Gly Thr Ala Asn Thr
225                 230                 235                 240
Ala Ala Asp Lys Ala Glu Ala Val Ala Ala Lys Val Thr Asp Ile Lys
                245                 250                 255
Ala Asp Ile Ala Thr Asn Lys Ala Asp Ile Ala Lys Asn Ser Ala Arg
            260                 265                 270
Ile Asp Ser Leu Asp Lys Asn Val Ala Asn Leu Arg Lys Glu Thr Arg
            275                 280                 285
Gln Gly Leu Ala Glu Gln Ala Ala Leu Ser Gly Leu Phe Gln Pro Tyr
    290                 295                 300
Asn Val Gly Arg Phe Asn Val Thr Ala Ala Val Gly Gly Tyr Lys Ser
305                 310                 315                 320
Glu Ser Ala Val Ala Ile Gly Thr Gly Phe Arg Phe Thr Glu Asn Phe
                325                 330                 335
Ala Ala Lys Ala Gly Val Ala Val Gly Thr Ser Ser Gly Ser Ser Ala
            340                 345                 350
Ala Tyr His Val Gly Val Asn Tyr Glu Trp
    355                 360
```

MENINGOCOCCAL B RECOMBINANT VACCINE

RELATED APPLICATIONS

This application claims priority to European Patent Application No. 21305211.1, filed Feb. 19, 2021, and U.S. Provisional Patent Application Ser. No. 63/172,885, filed Apr. 9, 2021, the entire disclosures of which are hereby incorporated herein by reference.

TECHNICAL FIELD

The present disclosure relates to the vaccine field. The present disclosure relates to immunogenic compositions and vaccines for preventing meningococcal infection, such as *Neisseria meningitidis* (*N. meningitidis* or Nm) serogroup B (MenB) infection.

TECHNICAL BACKGROUND

*Neisseria meningitidis* is a gram-negative diplococcus with humans as the sole known natural host. *N. meningitidis* is a frequent colonizer of the human naso- and oropharynx but can be found in other areas of the body such as the anal mucosa, the conjunctiva and the urogenital tract (Rouphael et al., *Methods Mol Biol.* 2012; 799:1-20; Stephens, Vaccine. 2009; 27 Suppl 2:B71-7; Batista et al., *Asian Pac J Trop Med.* 2017; 10(11):1019-29).

At least 12 different meningococcal serogroups have been classified based on the immunochemistry of the capsular polysaccharides (PS). Some strains are more likely than others to cause infection. Worldwide, most cases of meningococcal disease are caused by serogroups A, B, C, W, X, and Y. Serogroup B is responsible for endemic disease and some outbreaks (Harrison et al., [ed.] Orenstein W A, Offit P A, Edwards K M Plotkin S A. *Vaccines.* 7. Philadelphia (PA): Elsevier; 2018. p. 619-43; Borrow et al., *Expert Rev Vaccines.* 2017; 16(4):313-28; Harrison et al., *Emerg Infect Dis.* 2013; 19(4):566-73, Pollard, *Pediatr Infect Dis J.* 2004; 23 (12 Suppl):S274-9; Kvalsvig et al., *J Clin Pathol.* 2003; 56(6):417-22).

*N. meningitidis* serogroup B is a respiratory transmission bacterium (through droplets) that cannot survive in the environment, requiring close and prolonged contact, or direct physical contact (such as a kiss) for effective transmission. The asymptomatic carrier, present among less than 2% of children under 5 years of age and 20%-25% of adolescents and young adults, is the primary element in the pathogen transmission pathway and its maintenance in nature, even during periods of epidemics (Christensen et al., *Lancet Infect Dis.* 2010; 10(12):853-61; Batista et al., *Asian Pac J Trop Med.* 2017; 10(11):1019-29).

In general, the age groups with the highest incidence of carriage are adolescents and young adults, who are prone to engage in the behaviors recognized as risk factors for carriage and the eventual appearance of invasive meningococcal disease (IMD) ((Christensen et al., *Lancet Infect Dis.* 2010; 10(12):853-61; Stephens, *Vaccine.* 2009; 27 Suppl 2:B71-7; Bruce et al., *JAMA.* 2001; 286(6):688-93; Germinario et al., *Hum Vaccin.* 2010; 6(12):1025-7; MacLennan et al., *Emerg Infect Dis.* 2006; 12(6):950-7). Thus, vaccination of these age groups has the potential to impact the incidence of IMD in other age groups, which has been demonstrated in a number of European countries where vaccination campaigns with serogroup C conjugate vaccines have led to herd protection in unvaccinated age groups (Maiden et al., *J Infect Dis.* 2008; 197(5):737-43; Trotter et al., *Lancet.* 2004; 364(9431):365-7; Bijlsma et al., *Clin Infect Dis.* 2014; 59(9):1216-21).

Invasive meningococcal disease (IMD) is a serious illness caused by *N. meningitidis* (including *N. meningitidis* serogroup B), and symptoms may include intense headache, fever, nausea, vomiting, photophobia, stiff neck, lethargy, myalgia, and a characteristic petechial rash (Harrison et al., [ed.] Orenstein W A, Offit P A, Edwards K M Plotkin S A. *Vaccines.* 7. Philadelphia (PA): Elsevier; 2018. p. 619-43). IMD can lead to meningococcal meningoencephalitis and meningococcemia. Meningococcemia is probably the most rapidly fatal infectious condition to humans, with about 90% of deaths reported within the first 2 days of hospitalization. Inflammatory syndromes may arise in 6%-15% of IMD patients, due to deposits of antigen-antibody complex, composed mainly of capsular polysaccharides, specific immunoglobulins and complement fraction C3. These reactions generally occur 4 to 12 days after disease onset and include arthritis, mostly monoarticular (7%-14% of patients), cutaneous vasculitis, iritis, episcleritis, pleuritis and pericarditis. Simultaneously, reappearance of fever, leukocytosis and increased serum C-reactive protein may occur. Other complications that can occur in IMD patients include activation of herpes simplex infection, symmetrical distal necrosis, extensive ulcerations on vasculitis topographies, digestive bleeding, subdural effusion, myocarditis, rhabdomyolysis, adult respiratory distress syndrome, acid-base and hydroelectrolyte disorders, cerebral infarction and intracranial suppuration.

Sequelae may occur in IMD survivors. The risk of neurological sequelae occurrence is 7%-12% (a smaller rate than that of pneumococcal meningitis), primarily occurring in infants. Hearing loss (persistent or transitory) is the most common complication, occurring in approximately 4% of cases. Other sequelae include: visual deficits, hydrocephaly, ataxia, dysphasia, motor deficits, developmental delays, arthritis, spasticity, convulsions, renal failure, osteonecrosis, atrophic scarring, loss of parts of the extremities, learning disabilities and behavioral disorders among others (Batista et al., *Asian Pac J Trop Med.* 2017; 10(11):1019-29; Stephens et al., *Neisseria meningitidis.* [ed.] J. E. Bennett, R. Dolin and M. J. Blaser. Philadelphia: Elsevier Saunders; 2015. p. 2425-45; Campsall et al., *Crit Care Clin.* 2013; 29(3):393-409; Pace et al., *Vaccine.* 2012; 30 Suppl 2:B3-9).

Serogroup B is an important cause of endemic disease and is responsible for multiple prolonged epidemics in several industrialized countries (Vuocolo et al., *Hum Vaccin Immunother.* 2018; 14(5):1203-15), including Cuba (Rodriguez et al., *Mem Inst Oswaldo Cruz.* 1999; 94(4):433-40), Norway (Fredriksen et al., *NIPH Ann.* 1991; 14(2):67-79; discussion –80) and New Zealand (Martin et al., *J Infect Dis.* 1998; 177(2):497-500; Dyet et al., *Epidemiol Infect.* 2006; 134(2): 377-83). Smaller outbreaks due to a single strain have also been reported in other countries such as France (from 2000-2003) (Grodet et al., *Microbiol Infect.* 2004; 10(9): 845-8; Caron et al., *Lancet Infect Dis.* 2011; 11(6):455-63) and the United States (from 2013-2017), some of which have been associated with colleges and universities (Folaranmi et al., 2015. *MMWR Morb Mortal Wkly Rep.* 2015; 64(22):608-12; Atkinson et al., *Pharmacotherapy.* 2016; 36(8):880-92).

Two broadly protective protein-based vaccines targeting *N. meningitidis* group B have been recently licensed: 1) the 4-component MenB protein vaccine (4CMenB; BEXSERO® vaccine from GlaxoSmithKline, Inc. [GSK]) is licensed in the United States (US) as a two-dose schedule in individuals 10-25 years old, and for use in individuals from 2 months of age up to 50 years in Europe, Australia, Canada and some countries in South America; 2) a bivalent recombinant fHBP protein-based (rLP2086) vaccine (TRUMENBA® vaccine from Pfizer) is licensed in the US and in Europe as a 2- or 3-dose schedule in individuals 10-25 years old.

Clinical trials with those both licensed vaccines revealed that fever was an adverse event of special concern for pediatric populations. Fever >38° C. was reported in up to 70% of infants receiving BEXSERO vaccine with routine vaccines (fever >39° C. in 6-12%), leading to recommend the use of prophylactic paracetamol at the time of BEXSERO vaccine immunization (and within the first 24 hours of vaccination). During a TRUMENBA vaccine Phase I/IIb study in pediatric populations, fever (mostly <39.0° C.) was reported in 64% and 90% in participants receiving 20- or 60-μg rLP2086 dose, respectively, and the study was terminated early (Martinon-Torres et al., *Vaccine.* 2014; 32(40): 5206-11).

Humans immunized with these vaccines develop complement-mediated serum bactericidal antibody (SBA) responses. However, for TRUMENBA and BEXSERO vaccines, low fHBP-associated SBA activity and coverage were demonstrated against some MenB strains, especially in toddlers and infants (Brunelli et al., *Vaccine.* 2011; 29(5): 1072-81; Marshall et al., *Pediatr Infect Dis J.* 2012; 31(10): 1061-8). It was demonstrated that binding of a host molecule to a vaccine antigen could decrease immunogenicity by covering important epitopes or decreasing vaccine uptake, which could lead to reduced antigen processing and presentation (Meri et al., *Vaccine.* 2008; 26 Suppl 8:I113-7). Preclinical studies demonstrated that binding of factor H (fH) to wild-type recombinant fHBP antigens impaired protective serum anti-fHBP antibody responses in human fH transgenic mice and infant rhesus macaques (Costa et al., *mBio.* 2014; 5(5):e01625-14; Granoff et al., *Clin Vaccine Immunol.* 2013; 20(8):1099-107).

Therefore, it appears that there is still a need to have immunogenic compositions, such as vaccines, against *Neisseria meningitidis*, such as MenB, with a large coverage in terms of bacteria strains.

There is a need to have immunogenic compositions with a broader MenB strains coverage than BEXSERO or TRUMENBA.

There is also a need to have immunogenic compositions with a good reactogenic profile.

There is a need to have immunogenic compositions with a good reactogenic and safety profile for infant and pediatric uses.

Furthermore, there is a need to have immunogenic compositions with an improved reactogenic profile compared to TRUMENBA.

There is a need to have immunogenic compositions with an improved reactogenic profile compared to BEXSERO.

Also, there is a need for immunogenic compositions against MenB which can be easily combined with other antigens, such as *Neisseria meningitidis* ACWY antigens, for example ACWY polysaccharides conjugated to diphtheria or tetanus toxoid.

The present disclosure has for intent to satisfy all or part of those needs.

SUMMARY

In one aspect, it is disclosed a multicomponent meningococcal immunogenic composition comprising at least 4 antigens and aiming at providing broad protection against meningococcal infection, for example invasive meningococcal disease (IMD) caused by MenB with an acceptable safety profile for infant indication. It is composed of 3 main surface exposed recombinant *Neisseria* proteins selected on the basis of their key role in the *N. meningitidis* pathogenesis as well as their ability to induce serum bactericidal antibodies (SBA) to homologous and heterologous MenB strains (Pizza et al., *Science.* 2000; 287(5459):1816-20): 2 non-lipidated factor H binding proteins (fHBP) from subfamily A and B and a *Neisseria* adhesin A (NadA) protein. To improve immunogenicity and potential strain coverage of the multicomponent MenB vaccine, an outer membrane vesicle (OMV) obtained by detergent extraction (detergent-extracted OMV, dOMV, also referred to as Outer Membrane Protein Complex (OMPC)) was added to the formulation. The dOMV was from a MenB strain, for example a strain expressing a PorA protein, such as the PorA VR2 P1.2. dOMV efficacy is linked to bactericidal antibodies directed mainly against the homologous PorA, which is highly abundant on the surface of the bacterium.

Unexpectedly, the inventors have observed that the combinations of MenB antigens in the immunogenic compositions as disclosed herein were conferring to the compositions a broad coverage in terms of MenB strains against which an immune response can be elicited, while inducing low reactogenic and pro-inflammatory effects.

Indeed, as shown in the Examples section, the immunogenic compositions of the disclosure, such as vaccines, allowed reaching a broader MenB strains coverage than TRUMENBA or BEXSERO. Notably, the immunogenic compositions disclosed herein elicited protective immune response against 6 MenB strains not covered by BEXSERO.

Advantageously, the antigens of the immunogenic compositions disclosed herein provide cross-protection among the prevalent IMD-causing MenB strains.

Advantageously, the immunogenic compositions disclosed herein include 2 non-lipidated fHBP recombinant antigens, A05 (according to Pfizer's classification, aka variant 3.45 in Novartis nomenclature, or peptide ID45 according to PubMLST's nomenclature) and B01 (according to Pfizer's classification, aka variant 1.55 in Novartis nomenclature, or peptide ID55 according to PubMLST's nomenclature), representing 1 variant antigen from each of the 2 genetically and immunologically diverse subfamilies of fHBP which allows ensuring a broad protection against all MenB strains and to allow infant indication from six weeks onward.

A further advantage is that the immunogenic compositions disclosed herein comprise dOMV which may induce a specific protective response against strains expressing an homologous PorA, such as PorA VR2 strains, and for example a PorA VR2 P1.2 strain, as well as protective cross-reactivity against heterologous strains.

A further advantage of the immunogenic compositions disclosed herein is that they elicit immune response against MenB strains from the ST-41/44, the ST-32, the ST-269, the ST-213, the ST-35, the ST-461, the ST-11 and the ST-461 Clonal Complexes. Another advantage is that the immunogenic compositions disclosed herein elicit immune response against the ST-11 Clonal Complex which is an emerging hypervirulent Clonal Complex.

In addition, as shown in the Examples section, the immunogenic compositions disclosed herein present a reactogenic profile comparable to, and even globally less reactogenic than, the one of BEXSERO which is improved (i.e., less reactogenic) compared to TRUMENBA. Notably, the immunogenic compositions as disclosed present a weaker proinflammatory cytokine response than TRUMENBA. Furthermore, they have minimal effect on cell viability.

According to one of its aspects, the present disclosure relates to an immunogenic composition comprising a combination of meningococcal antigens, said combination comprising at least one factor H binding protein (fHBP) A protein, at least one fHBP B protein, at least one *Neisseria* adhesin A (NadA) protein, and at least one detergent-extracted Outer Membrane Vesicle (dOMV). The antigens are present in an immunologically effective amount.

In one embodiment, the meningococcal antigens may be from a *Neisseria meningitidis* serogroup B.

According to another of its aspects, the present disclosure relates to an immunogenic composition comprising a combination of *Neisseria meningitidis* serogroup B antigens, said combination comprising at least one factor H binding protein (fHBP) A protein, at least one fHBP B protein, at least one *Neisseria* adhesin A (NadA) protein, and at least one detergent-extracted Outer Membrane Vesicle (dOMV). The fHBP A protein and/or the fHBP B protein may be non-lipidated.

In another embodiment, a fHBP A protein may be a lipidated or a non-lipidated protein, and for example is a non-lipidated protein.

In another embodiment, a fHBP B protein may be a lipidated or a non-lipidated protein, and for example is a non-lipidated protein.

In another embodiment, a fHBP A protein and/or a fHBP B protein may be non-lipidated. In one embodiment, both a fHBP A protein and a fHBP B protein may be non-lipidated.

In one embodiment, a fHBP A protein may be a non-naturally occurring fHBP.

In one embodiment, a fHBP B protein may be a non-naturally occurring fHBP.

In one embodiment, a fHBP A and/or a fHBP B protein may be non-naturally occurring fHBP.

In one embodiment, a fHBP A and/or a fHBP B protein may be a mutated fHBP. In one embodiment, a fHBP A and/or a fHBP B protein may be a mutated non-lipidated fHBP.

In one embodiment, a fHBP A protein may be a mutated protein comprising at least about 85%, at least about 90%, at least about 95%, at least about 98%, at least about 99%, or at least about 99.5% identity with SEQ ID NO: 1.

In another embodiment, a fHBP A protein may comprise at least one amino acid substitution selected from at least one of: a) an amino acid substitution of the asparagine at amino acid 115 (N115); b) an amino acid substitution of the aspartic acid at amino acid 121 (D121); c) an amino acid substitution of the serine at amino acid 128 (S128); d) an amino acid substitution of the leucine at amino acid 130 (L130); e) an amino acid substitution of the valine at position 131 (V131); f) an amino acid substitution of the glycine at position 133 (G133); g) an amino acid substitution of the lysine at position 219 (K219); and h) an amino acid substitution of the glycine at position 220 (G220), based on the numbering of SEQ ID NO:6.

In one embodiment, a fHBP A protein may be a mutated protein comprising at least about 85%, at least about 90%, at least about 95%, at least about 98%, at least about 99%, or at least about 99.5% identity with SEQ ID NO: 1 and comprising at least one amino acid substitution selected from at least one of: a) an amino acid substitution of the asparagine at amino acid 115 (N115); b) an amino acid substitution of the aspartic acid at amino acid 121 (D121); c) an amino acid substitution of the serine at amino acid 128 (S128); d) an amino acid substitution of the leucine at amino acid 130 (L130); e) an amino acid substitution of the valine at position 131 (V131); f) an amino acid substitution of the glycine at position 133 (G133); g) an amino acid substitution of the lysine at position 219 (K219); and h) an amino acid substitution of the glycine at position 220 (G220), based on the numbering of SEQ ID NO:6.

In one embodiment, a fHBP A protein may comprise at least the amino acid substitution G220S based on the numbering of SEQ ID NO:6. A fHBP A protein may be a non-lipidated protein comprising at least about 85%, at least about 90%, at least about 95%, at least about 98%, at least about 99%, or at least about 99.5% identity with SEQ ID NO: 1 and comprising at least the amino acid substitution G220S, based on the numbering of SEQ ID NO:6.

In one embodiment, a fHBP A protein may comprise at least the three amino acid substitutions selected in the group consisting of G220S, L130R, and G133D, based on the numbering of SEQ ID NO:6. In another embodiment, a fHBP A protein may comprise only the three amino acid substitutions G220S, L130R, and G133D, based on the numbering of SEQ ID NO:6. A fHBP A protein may be a mutated protein comprising at least about 85%, at least about 90%, at least about 95%, at least about 98%, at least about 99%, or at least about 99.5% identity with SEQ ID NO: 1 and comprising at least or only the three amino acid substitutions selected in the group consisting of G220S, L130R, and G133D, based on the numbering of SEQ ID NO:6.

In another embodiment, a fHBP A protein may comprise or consist of SEQ ID NO: 2.

In one embodiment, a fHBP B protein may be a mutated protein comprising at least about 85%, at least about 90%, at least about 95%, at least about 98%, at least about 99%, or at about least 99.5% identity with SEQ ID NO: 3.

In another embodiment, a fHBP B protein may comprise at least one amino acid substitution selected from at least one of: a) an amino acid substitution of the glutamine at amino acid 38 (Q38); b) an amino acid substitution of the glutamic acid at amino acid 92 (E92); c) an amino acid substitution of the arginine at amino acid 130 (R130); d) an amino acid substitution of the serine at amino acid 223 (S223); and e) an amino acid substitution of the histidine at amino acid 248 (H248), based on the numbering of SEQ ID NO:6.

In one embodiment, a fHBP B protein may be a mutated protein comprising at least about 85%, at least about 90%, at least about 95%, at least about 98%, at least about 99%, or at about least 99.5% identity with SEQ ID NO: 3 and comprising at least one amino acid substitution selected from at least one of: a) an amino acid substitution of the glutamine at amino acid 38 (Q38); b) an amino acid substitution of the glutamic acid at amino acid 92 (E92); c) an amino acid substitution of the arginine at amino acid 130 (R130); d) an amino acid substitution of the serine at amino acid 223 (S223); and e) an amino acid substitution of the histidine at amino acid 248 (H248), based on the numbering of SEQ ID NO:6.

In another embodiment, a fHBP B protein may comprise at least the amino acid substitution H248L, based on the numbering of SEQ ID NO:6. In another embodiment, a fHBP B protein may comprise only the amino acid substitution H248L, based on the numbering of SEQ ID NO:6. A fHBP B protein may be a mutated protein comprising at least about 85%, at least about 90%, at least about 95%, at least about 98%, at least about 99%, or at least about 99.5% identity with SEQ ID NO: 3 and comprising at least or only the amino acid substitution H248L, based on the numbering of SEQ ID NO:6.

In another embodiment, a fHBP B protein may comprise or consist of SEQ ID NO: 4.

In one embodiment, a fHBP A protein and/or a fHBP B may be present in an amount ranging from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose, or at about 25 μg/dose, or at about 50 μg/dose, or else at about 100 μg/dose.

As used herein, the term "dose" refers to the total amount or volume of composition administered to an individual. A dose may range from about 0.1 ml to about 1 ml, for example from about 0.2 ml to about 0.8 ml, from about 0.4 ml to about 0.6 ml, or may be of about 0.5 ml.

In one embodiment, a NadA protein may be a NadA1 protein.

In another embodiment, a NadA protein may comprise at least about 85%, at least about 90%, at least about 95%, at least about 98%, at least about 99%, or at least about 99.5% identity with SEQ ID NO: 5. In another embodiment, a NadA protein may comprise or consist of SEQ ID NO:5.

In one embodiment, a NadA protein may be present in an amount ranging from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose, or at about 25 μg/dose, or at about 50 μg/dose, or else at about 100 μg/dose. In one embodiment, a NadA protein may be present in an amount at about 50 μg/dose.

In one embodiment, a dOMV may comprise outer membrane protein porin A (PorA). In one embodiment, a dOMV may comprise outer membrane protein porin B (PorB). In another embodiment, a dOMV may comprise outer membrane protein porin A (PorA) and outer membrane protein porin B (PorB).

In another embodiment, a dOMV may comprise outer membrane protein porin A (PorA) and/or outer membrane protein porin B (PorB). A dOMV may comprise porin A (Serosubtype PorA VR2 P1.2), porin B (Serotype PorB P2.2a) and, optionally immunotype LOS L3,7. PorA and PorB may represent about 50% of the proteins of the dOMV.

PorA may be present in an amount ranging from about 3% to about 15%, or in an amount of about 5% to about 9 or about 10% relative to the total proteins present in said dOMV. PorB may be present in an amount ranging from about 30% to about 70%, or from about 35% to about 65%, or from about 38% to about 58% relative to the total proteins present in the dOMV.

In one embodiment, a dOMV may comprise porin A (PorA). In one embodiment, PorA may be a PorA of VR2 family. In an example, a dOMV may comprise a PorA VR2 P1.2 subtype.

In one embodiment, a dOMV may be obtained from MenB strain 99M expressing PorA VR2, P1.2.

In one embodiment, a dOMV may comprise PorA VR2 P1.2 and PorB P2.2a.

In one embodiment, a dOMV may be obtained with a detergent-extraction method using at least a step of deoxycholate treatment.

In one embodiment, a dOMV may be present in an amount ranging from about 5 μg/dose to about 400 μg/dose, or from about 10 μg/dose to about 300 μg/dose, or from about 25 μg/dose to about 250 μg/dose, or from about 35 μg/dose to about 225 μg/dose, or from about 50 μg/dose to about 200 μg/dose, or from about 75 μg/dose to about 180 μg/dose, or from about 100 μg/dose to about 150 μg/dose, or from about 110 μg/dose to about 125 μg/dose, or at about 25 μg/dose, or at about 50 μg/dose, or at about 125 μg/dose.

In another embodiment, a composition as disclosed herein may further comprise an adjuvant. In one embodiment, an adjuvant may be an aluminum-based adjuvant. In one embodiment, an aluminum-based adjuvant may be an aluminum-based adjuvant selected in a group comprising aluminum hydroxide adjuvant, aluminum phosphate adjuvant, sulphate aluminum salt adjuvant, aluminium hydroxyphosphate sulfate adjuvant, potassium aluminium sulfate adjuvant, aluminum hydroxycarbonate, a combination of aluminum hydroxide and magnesium hydroxide, and mixtures thereof. In one embodiment, an adjuvant may be an aluminum phosphate adjuvant.

In another embodiment, a composition as disclosed herein may further comprise a pharmaceutically acceptable excipient.

In another embodiment, a composition as disclosed herein may further comprise a buffer. In one embodiment, a buffer may be selected in a group comprising a Tris buffer, an acetate buffer, a citrate buffer, a phosphate buffer, an HEPES buffer, or a histidine buffer. In one embodiment, a buffer may be an acetate buffer. In one embodiment, an acetate buffer may be a sodium acetate buffer. In one embodiment, a sodium acetate buffer may be present at a concentration ranging from about 10 mM to about 300 mM, or ranging from about 10 mM to about 250 mM, or ranging from about 20 mM to about 250 mM, or ranging from about 20 mM to about 150 mM, or from about 20 mM to about 130 mM, or from about 30 mM to about 120 mM, or from about 40 mM to about 100 mM, or from about 50 mM to about 80 mM, or from about 50 mM to about 60 mM, or for example at a concentration of about 50 mM.

In another embodiment, a composition as disclosed herein may further comprise a salt such as a sodium salt, a calcium salt, or a magnesium salt. A sodium salt may be for example a sodium salt selected in the group comprising sodium chloride, sodium phosphate. In one embodiment a sodium salt may be sodium chloride. A calcium salt may be a calcium chloride salt. A magnesium salt may be a magnesium chloride salt. In one embodiment, a sodium salt may be present at concentration ranging from about 10 mM to about 300 mM, or from about 30 mM to about 280 mM, or from about 50 mM to about 250 mM, or from about 60 mM to about 220 mM, or from about 80 mM to about 200 mM, or from about 100 mM to about 180 mM, or from about 120 mM to about 160 mM, or may be for example at a concentration of about 150 mM. A calcium or a magnesium salt may be present in an amount ranging from about 1 mM to about 15 mM, or from about 5 mM to about 10 mM.

In another embodiment, a composition as disclosed herein may have a pH in a range of about 4.0 to about 9.0. In one embodiment, a pH of the compositions disclosed herein may range from about 4.5 to about 8.5, or from about 4.8 to about 8.2, or from about 5.0 to about 8.0, or from about 5.2 to about 7.5, or from about 5.4 to about 7.0, or from about 5.5 to about 6.8, or from about 5.7 to about 6.5, or from about 5.8 to about 6.2, or may be about 6.0. In another embodiment, a composition as disclosed herein may comprise or consist of a non-lipidated fHBP A protein comprising or consisting of SEQ ID NO: 2, a non-lipidated fHBP B protein comprising or consisting of SEQ ID NO: 4, a NadA protein and dOMV from a MenB expressing PorA proteins. In the composition NadA may be NadA1 or may comprise at least about 85%, at least about 90%, at least about 95%, at least about 98%, at least about 99%, at least about 99.5%, or about 100% amino acid sequence identity to SEQ ID NO: 5 or consist of SEQ ID NO:5, and/or dOMV may comprise a PorA VR2 subtype or a PorA VR2 P1.2 and optionally a PorB P2.2a or may be obtained from MenB strain 99M. A composition as disclosed herein may comprise an aluminum phosphate adjuvant. A composition as disclosed herein may comprise a 50 mM acetate buffer and pH 6.0.

In another embodiment, a composition as disclosed herein may comprise or consist of a non-lipidated mutated fHBP A protein comprising at least about 85%, at least about 90%, at least about 95%, at least about 98%, at least about 99%, or at least about 99.5% identity with SEQ ID NO: 1, a non-lipidated mutated fHBP B protein comprising at least about 85%, at least about 90%, at least about 95%, at least about 98%, at least 99%, or at least about 99.5% identity with SEQ ID NO: 3, a NadA protein and dOMV from a MenB expressing PorA proteins. In the composition NadA may be NadA1 or may comprise at least about 85%, at least about 90%, at least about 95%, at least about 98%, at least about 99%, at least about 99.5%, or about 100% amino acid sequence identity to SEQ ID NO: 5 or consist of SEQ ID NO:5, and/or dOMV may comprise a PorA VR2 subtype or a PorA VR2 P1.2 and optionally a PorB P2.2a or may be obtained from MenB strain 99M. A composition as disclosed herein may comprise an aluminum phosphate adjuvant. A composition as disclosed herein may comprise a 50 mM acetate buffer and pH 6.0.

In another embodiment, a composition as disclosed herein may comprise or consist of a non-lipidated mutated fHBP A protein comprising at least about 85%, at least about 90%, at least about 95%, at least about 98%, at least about 99%, or at least about 99.5% identity with SEQ ID NO: 1 and comprising at least one amino acid substitution selected from at least one of: a) an amino acid substitution of the asparagine at amino acid 115 (N115); b) an amino acid substitution of the aspartic acid at amino acid 121 (D121); c) an amino acid substitution of the serine at amino acid 128 (S128); d) an amino acid substitution of the leucine at amino acid 130 (L130); e) an amino acid substitution of the valine at position 131 (V131); f) an amino acid substitution of the glycine at position 133 (G133); g) an amino acid substitution of the lysine at position 219 (K219); and h) an amino acid substitution of the glycine at position 220 (G220), based on the numbering of SEQ ID NO:6, a non-lipidated mutated fHBP B protein comprising at least about 85%, at least about 90%, at least about 95%, at least about 98%, at least about 99%, or at least about 99.5% identity with SEQ ID NO: 3 and comprising at least one amino acid substitution selected from at least one of: a) an amino acid substitution of the glutamine at amino acid 38 (Q38); b) an amino acid substitution of the glutamic acid at amino acid 92 (E92); c) an amino acid substitution of the arginine at amino acid 130 (R130); d) an amino acid substitution of the serine at amino acid 223 (S223); and e) an amino acid substitution of the histidine at amino acid 248 (H248), based on the numbering of SEQ ID NO:6, a NadA protein and dOMV from a MenB expressing PorA proteins. In the composition NadA may be NadA1 or may comprise at least about 85%, at least about 90%, at least about 95%, at least about 98%, at least about 99%, at least about 99.5%, or about 100% amino acid sequence identity to SEQ ID NO: 5 or consist of SEQ ID NO:5, and/or dOMV may comprise a PorA VR2 subtype or a PorA VR2 P1.2 and optionally a PorB P2.2a or may be obtained from MenB strain 99M. A composition as disclosed herein may comprise an aluminum phosphate adjuvant. A composition as disclosed herein may comprise a 50 mM acetate buffer and pH 6.0.

In another embodiment, a composition as disclosed herein may comprise or consist of a non-lipidated mutated fHBP A protein comprising at least about 85%, at least about 90%, at least about 95%, at least about 98%, at least about 99%, or at least about 99.5% identity with SEQ ID NO: 1 and comprising at least one amino acid substitution selected in the group consisting of G220S, L130R, and G133D, based on the numbering of SEQ ID NO:6, a non-lipidated mutated fHBP B protein comprising at least about 85%, at least about 90%, at least about 95%, at least about 98%, at least about 99%, or at least about 99.5% identity with SEQ ID NO: 3 and comprising at least the amino acid substitution H248L, based on the numbering of SEQ ID NO:6, a NadA protein and dOMV from a MenB expressing PorA proteins. In the composition NadA may be NadA1 or may comprise at least about 85%, at least about 90%, at least about 95%, at least about 98%, at least about 99%, at least about 99.5%, or about 100% amino acid sequence identity to SEQ ID NO: 5 or consist of SEQ ID NO:5, and/or dOMV may comprise a PorA VR2 subtype or a PorA VR2 P1.2 and optionally a PorB P2.2a or may be obtained from MenB strain 99M. A composition as disclosed herein may comprise an aluminum phosphate adjuvant. A composition as disclosed herein may comprise a 50 mM acetate buffer and pH 6.0.

In another embodiment, a composition as disclosed herein may comprise or consist of a non-lipidated mutated fHBP A protein comprising at least about 85%, at least about 90%, at least about 95%, at least about 98%, at least about 99%, or at least about 99.5% identity with SEQ ID NO: 1 and comprising at least the three amino acid substitutions selected in the group consisting of G220S, L130R, and G133D, based on the numbering of SEQ ID NO:6, a non-lipidated mutated fHBP B protein comprising at least about 85%, at least about 90%, at least about 95%, at least about 98%, at least about 99%, or at least about 99.5% identity with SEQ ID NO: 3 and comprising at least the amino acid substitution H248L, based on the numbering of SEQ ID NO:6, a NadA protein and dOMV from a MenB expressing PorA proteins. In the composition NadA may be NadA1 or may comprise at least about 85%, at least about 90%, at least about 95%, at least about 98%, at least about 99%, at least about 99.5%, or about 100% amino acid sequence identity to SEQ ID NO: 5 or consist of SEQ ID NO:5, and/or dOMV may comprise a PorA VR2 subtype or a PorA VR2 P1.2 and optionally a PorB P2.2a or may be obtained from MenB strain 99M. A composition as disclosed herein may comprise an aluminum phosphate adjuvant. A composition as disclosed herein may comprise a 50 mM acetate buffer and pH 6.0.

In another embodiment, a composition as disclosed herein may comprise or consist of a non-lipidated mutated fHBP A protein comprising at least about 85%, at least about 90%, at least about 95%, at least about 98%, at least about 99%, or at least about 99.5% identity with SEQ ID NO: 1 and comprising only the three amino acid substitutions selected in the group consisting of G220S, L130R, and G133D, based on the numbering of SEQ ID NO:6, a non-lipidated mutated fHBP B protein comprising at least about 85%, at least about 90%, at least about 95%, at least about 98%, at least about 99%, or at least about 99.5% identity with SEQ ID NO: 3 and comprising only the amino acid substitution H248L, based on the numbering of SEQ ID NO:6, a NadA protein and dOMV from a MenB expressing PorA proteins. In the composition NadA may be NadA1 or may comprise at least about 85%, at least about 90%, at least about 95%, at least about 98%, at least 99%, at least about 99.5%, or about 100% amino acid sequence identity to SEQ ID NO: 5 or consist of SEQ ID NO:5, and/or dOMV may comprise a PorA VR2 subtype or a PorA VR2 P1.2 and optionally a PorB P2.2a or may be obtained from MenB strain 99M. A composition as disclosed herein may comprise an aluminum phosphate adjuvant. A composition as disclosed herein may comprise a 50 mM acetate buffer and pH 6.0.

In another embodiment, a composition as disclosed herein may comprise or consist of a non-lipidated fHBP A protein comprising or consisting of SEQ ID NO: 2, a non-lipidated fHBP B protein comprising or consisting of SEQ ID NO: 4, a NadA protein comprising or consisting of SEQ ID NO: 5, dOMV from a MenB expressing PorA VR2 P1.2 and optionally a PorB P2.2a or obtained from MenB strain 99M. A composition as disclosed herein may comprise an aluminum phosphate adjuvant. A composition as disclosed herein may comprise a 50 mM acetate buffer and pH 6.0.

In another embodiment, a composition as disclosed herein may comprise or consist of a non-lipidated fHBP A protein consisting of SEQ ID NO: 2, a non-lipidated fHBP B protein consisting of SEQ ID NO: 4, a NadA protein consisting of SEQ ID NO: 5 and dOMV from a MenB expressing PorA VR2 P1.2 and optionally a PorB P2.2a or obtained from MenB strain 99M. A composition as disclosed herein may comprise an aluminum phosphate adjuvant.

In another embodiment, a composition as disclosed herein may comprise or consist of a non-lipidated fHBP A protein consisting of SEQ ID NO: 2, a non-lipidated fHBP B protein consisting of SEQ ID NO: 4, a NadA protein consisting of SEQ ID NO: 5, dOMV from a MenB expressing PorA VR2 P1.2 and optionally a PorB P2.2a or obtained from MenB strain 99M., an aluminum phosphate adjuvant, 50 mM acetate buffer and pH 6.0.

In another embodiment, a composition as disclosed herein may comprise or consist of a mRNA coding for a fHBP A protein comprising at least about 85%, at least about 90%, at least about 95%, at least about 98%, at least about 99%, at least about 99.5%, or about 100% amino acid sequence identity to SEQ ID NO: 2, a mRNA coding for a fHBP B protein comprising at least about 85%, at least about 90%, at least about 95%, at least about 98%, at least about 99%, at least about 99.5%, or about 100% amino acid sequence identity to SEQ ID NO: 4, a mRNA coding for a NadA protein comprising at least about 85%, at least about 90%, at least about 95%, at least about 98%, at least about 99%, at least about 99.5%, or about 100% amino acid sequence identity to SEQ ID NO: 5 and dOMV from a MenB expressing a PorA. The PorA may be a PorA VR2 subtype or a PorA VR2 P1.2.

In another embodiment, a composition as disclosed herein may comprise or consist of about 25 to about 100 µg/dose of a non-lipidated fHBP A protein comprising SEQ ID NO: 2, about 25 to about 100 µg/dose of a non-lipidated fHBP B protein comprising SEQ ID NO: 4, about 25 to about 100 µg/dose of a NadA protein comprising SEQ ID NO: 5, about 20 to about 150 µg/dose of dOMV from a MenB strain expressing PorA VR2 P1.2, about 100 to about 600 µg/dose of aluminum phosphate adjuvant, 50 mM acetate buffer and pH 6.0.

In another embodiment, a composition as disclosed herein may comprise or consist of about 25 to about 100 µg/dose of a non-lipidated fHBP A protein consisting of SEQ ID NO: 2, about 25 to about 100 µg/dose of a non-lipidated fHBP B protein consisting of SEQ ID NO: 4, about 25 to about 100 µg/dose of a NadA protein consisting of SEQ ID NO: 5, about 20 to about 150 µg/dose of dOMV from a MenB strain expressing PorA VR2 P1.2, about 100 to about 600 µg/dose of aluminum phosphate adjuvant, 50 mM acetate buffer and pH 6.0.

In another aspect, the present disclosure relates to a vaccine comprising a composition as disclosed herein.

In another aspect, the present disclosure relates to a composition as disclosed herein as a medicament, in particular as a vaccine.

In another aspect, the present disclosure relates to a composition as disclosed herein for use in protecting against a meningococcal infection, and in one exemplary embodiment against *N. meningitidis* serogroup B infection.

In another aspect, the present disclosure relates to a composition as disclosed herein for use in inducing an immune response against a meningococcus bacterium, and in one exemplary embodiment against *N. meningitidis* serogroup B bacterium.

In another aspect, the present disclosure relates to a composition as disclosed herein for use in inducing an immune response against a *N. meningitidis* serogroup B bacterium from the ST-41/44, the ST-32, the ST-269, the ST-213, the ST-35, the ST-461, the ST-11 and/or ST-461 Clonal Complexes.

In another aspect, the present disclosure relates to a composition as disclosed herein for use in inducing an immune response against a *N. meningitidis* serogroup B bacterium from the ST-11 Clonal Complex.

In another aspect, the present disclosure relates to a method for protecting an individual against a meningococcal infection, and in one exemplary embodiment against *N. meningitidis* serogroup B infection, the method comprising at least the step of administering to the individual an immunogenic composition as disclosed herein, or a vaccine as disclosed herein.

In another aspect, the present disclosure relates to a method for reducing a risk of occurrence of an invasive meningococcal disease caused by a meningococcal infection in an individual, and in one exemplary embodiment against *N. meningitidis* serogroup B infection, the method comprising at least the step of administering to the individual an immunogenic composition as disclosed herein, or a vaccine as disclosed herein.

In another aspect, the present disclosure relates to a method for eliciting an immune response against a meningococcus bacterium in an individual, and in one exemplary embodiment against *N. meningitidis* serogroup B bacterium, the method comprising at least the step of administering to the individual an immunogenic composition as disclosed herein, or a vaccine as disclosed herein.

In another aspect, the present disclosure relates to a method for eliciting an immune response against a *N. meningitidis* serogroup B bacterium from the ST-41/44, the ST-32, the ST-269, the ST-213, the ST-35, the ST-461, the ST-11 and/or ST-461 Clonal Complexes, the method comprising at least the step of administering to the individual an immunogenic composition as disclosed herein, or a vaccine as disclosed herein.

In another aspect, the present disclosure relates to a method for eliciting an immune response against a *N. meningitidis* serogroup B bacterium from the ST-11 Clonal Complex, the method comprising at least the step of administering to the individual an immunogenic composition as disclosed herein, or a vaccine as disclosed herein.

In another aspect, the present disclosure relates to a method for preparing an immunogenic composition as disclosed herein or a vaccine as disclosed herein, the method comprising at least a step of admixing meningococcal antigens and optionally an aluminum salt, said antigens comprising at least one factor H binding protein (fHBP) A protein, at least one fHBP B protein, at least one Neisseria adhesin A (NadA) protein, and at least one detergent-extracted Outer Membrane Vesicle (dOMV).

In one embodiment, a step of admixing may comprise a blending of a first mixture of at least one factor H binding protein (fHBP) A protein optionally adsorbed onto $AlPO_4$ and of at least one fHBP B protein optionally adsorbed onto $AlPO_4$ salt with a second mixture of at least one NadA protein optionally adsorbed onto $AlPO_4$ and of dOMV.

In one embodiment, a step of admixing may comprise a blending of a first mixture of at least one factor H binding protein (fHBP) A protein adsorbed onto $AlPO_4$ and of at least one fHBP B protein adsorbed onto $AlPO_4$ salt with a second mixture of at least one NadA protein adsorbed onto $AlPO_4$ and of dOMV.

In another embodiment, antigens and aluminum salt for use in a method for preparing as disclosed herein may be in a buffer.

In another aspect, the present disclosure relates to a kit-of-parts comprising a plurality of containers wherein each of the container is comprising at least one or a combination of at least two meningococcal antigens, said antigens being selected from the group comprising fHBP A protein, fHBP B protein, NadA protein, and detergent-extracted Outer Membrane Vesicle (dOMV).

In one embodiment, at least one of the antigens of the kit-of-parts may be in dried-form. In one embodiment, at least one of the antigens may be in lyophilized or dry micropellets form. In one embodiment, a kit may optionally comprise a container comprising a physiologically injectable vehicle.

DESCRIPTION OF THE FIGURES

FIG. 2A represents the specific anti-NadA IgG titers measured by ELISA in sera collected on D0 (Open/White symbols) and D42 (Closed/Black symbols) from rabbits immunized on D0 and D28 with BEXSERO or with the Formulations F1-F5 and F1 co-administered with MENQUADFI. FIG. 2B represents the specific anti-dOMV IgG measured by ELISA in sera collected on D0 and D42 from rabbits immunized on D0, D28 and D56 with Formulations F1 to F5 and F1 co-administered with MENQUADFI.

FIG. 14A represents the results obtained with F2 and F3 formulations and FIG. 14B and FIG. 14C represent the results obtained with F1, F4 and F5 formulations.

FIG. 17A represents the results obtained with F2 and F3 formulations and FIG. 17B represents the results obtained with F1, F4 and F5 formulations.

DESCRIPTION OF THE SEQUENCES

Figure 1A:
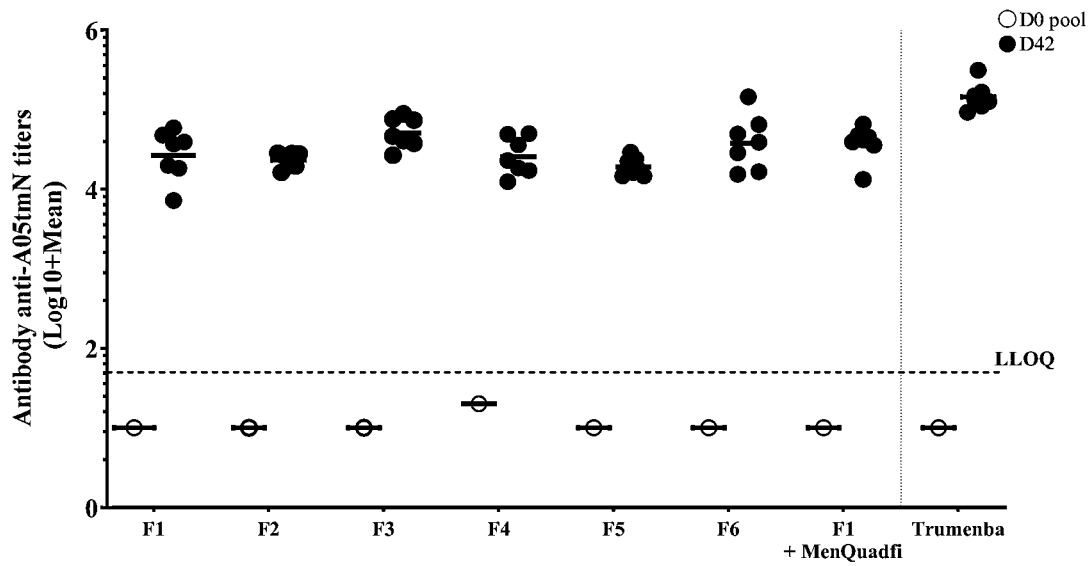
FIGS. 1A & 1B represent the specific anti-A05tmN (FIG. 1A) or anti-B01smN (FIG. 1B) IgG titers measured by ELISA in sera collected on D0 (Open/White symbols) and D42 (Closed/Black symbols) from rabbits immunized on D0, D28 and D56 with TRUMENBA or with Formulations F1 to F6 or F1 co-administered with MENQUADFI (LLOQ means lower limit of quantification).

SEQ ID NO: 1 represents fHBP A05 wild-type sequence without the signal peptide responsible for lipidation.

CSSGSGSGGGGVAADIGTGLADALTAPLDHKDKGLKSLTLEDSISQNGTL

TLSAQGAEKTFKVGDKDNSLNTGKLKNDKISRFDFVQKIEVDGQTITLAS

GEFQIYKQDHSAVVALQIEKINNPDKIDSLINQRSFLVSGLGGEHTAFNQ

LPSGKAEYHGKAFSSDDAGGKLTYTIDFAAKQGHGKIEHLKTPEQNVELA

SAELKADEKSHAVILGDTRYGSEEKGTYHLALFGDRAQEIAGSATVKIRE

KVHEIGIAGKQ

SEQ ID NO: 2 represents the mutated fHBP A05 sequence without the signal peptide responsible for lipidation and with the mutations G220S, L130R, G133D (numbering is determined with respect to sequence SEQ ID NO: 6 (fHBP B24)).

CSSGSGSGGGGVAADIGTGLADALTAPLDHKDKGLKSLTLEDSISQNGTL

TLSAQGAEKTFKVGDKDNSLNTGKLKNDKISRFDFVQKIEVDGQTITLAS

GEFQIYKQDHSAVVALQIEKINNPDKIDSLINQRSFRVSDLGGEHTAFNQ

LPSGKAEYHGKAFSSDDAGGKLTYTIDFAAKQGHGKIEHLKTPEQNVELA

SAELKADEKSHAVILGDTRYGSEEKSTYHLALFGDRAQEIAGSATVKIRE

KVHEIGIAGKQ

SEQ ID NO: 3 represents fHBP B01 wild-type sequence without the signal peptide responsible for lipidation.

CSSGGGGSGGGGVTADIGTGLADALTAPLDHKDKGLKSLTLEDSISQNG

TLTLSAQGAEKTYGNGDSLNTGKLKNDKVSRFDFIRQIEVDGQLITLES

GEFQVYKQSHSALTALQTEQEQDPEHSEKMVAKRRFRIGDIAGEHTSFD

KLPKDVMATYRGTAFGSDDAGGKLTYTIDFAAKQGHGKIEHLKSPELNV

DLAVAYIKPDEKHHAVISGSVLYNQDEKGSYSLGIFGEKAQEVAGSAEV

ETANGIHHIGLAAKQ

SEQ ID NO: 4 represents the mutated fHBP B01 sequence without the signal peptide responsible for lipidation and with the mutation H248L (numbering is determined with respect to sequence SEQ ID NO: 6 (fHBP B24).

CSSGGGGSGGGGVTADIGTGLADALTAPLDHKDKGLKSLTLEDSISQNG

TLTLSAQGAEKTYGNGDSLNTGKLKNDKVSRFDFIRQIEVDGQLITLES

GEFQVYKQSHSALTALQTEQEQDPEHSEKMVAKRRFRIGDIAGEHTSFD

KLPKDVMATYRGTAFGSDDAGGKLTYTIDFAAKQGHGKIEHLKSPELNV

DLAVAYIKPDEKHHAVISGSVLYNQDEKGSYSLGIFGEKAQEVAGSAEV

ETANGIHLIGLAAKQ

SEQ ID NO: 5 represents NadA1 sequence from MenB MC58 strain in which the 23 amino acids of the signal peptide in N-terminus and the last 55 amino acids of the C-terminus have been deleted.

MTSDDDVKKAATVAIVAAYNNGQEINGFKAGETIYDIGEDGTITQKDATA

ADVEADDFKGLGLKKVVTNLTKTVNENKQNVDAKVKAAESEIEKLTTKLA

DTDAALADTDAALDETTNALNKLGENITTFAEETKTNIVKIDEKLEAVAD

TVDKHAEAFNDIADSLDETNTKADEAVKTANEAKQTAEETKQNVDAKVKA

AETAAGKAEAAAGTANTAADKAEAVAAKVTDIKADIATNKADIAKNSARI

DSLDKNVANLRKETRQGLAEQAALSGLFQPYNVG

SEQ ID NO: 6 represents the fHBP B24 wild-type sequence on the basis of which the numbering of the positions of the mutations in A05 and B01 are determined.

CSSGGGGVAADIGAGLADALTAPLDHKDKGLQSLTLDQSVRKNEKLKLAA

QGAEKTYGNGDSLNTGKLKNDKVSRFDFIRQIEVDGQLITLESGEFQVYK

QSHSALTAFQTEQIQDSEHSGKMVAKRQFRIGDIAGEHTSFDKLPEGGRA

-continued

TYRGTAFGSDDAGGKLTYTIDFAAKQGNGKIEHLKSPELNVDLAAADIKP

DGKRHAVISGSVLYNQAEKGSYSLGIFGGKAQEVAGSAEVKTVNGIRHIG

LAAKQ

SEQ ID NO: 7 represents the wild-type NadA1 sequence from MenB MC58 strain.

MKHFPSKVLTTAILATFCSGALAATSDDDVKKAATVAIVAAYNNGQEING

FKAGETIYDIGEDGTITQKDATAADVEADDFKGLGLKKVVTNLTKTVNEN

KQNVDAKVKAAESEIEKLTTKLADTDAALADTDAALDETTNALNKLGENI

TTFAEETKTNIVKIDEKLEAVADTVDKHAEAFNDIADSLDETNTKADEAV

KTANEAKQTAEETKQNVDAKVKAAETAAGKAEAAAGTANTAADKAEAVAA

KVTDIKADIATNKADIAKNSARIDSLDKNVANLRKETRQGLAEQAALSGL

FQPYNVGRFNVTAAVGGYKSESAVAIGTGFRFTENFAAKAGVAVGTSSGS

SAAYHVGVNYEW

DETAILED DESCRIPTION

Definitions

It must be noted that as used herein and in the appended claims, the singular forms "a", "an", and "the" include plural referents unless the context clearly dictates otherwise. Thus, for example, reference to "an antigen" includes a plurality of such antigens and reference to "the protein" includes reference to one or more proteins, and so forth.

The terms "about" or "approximately" as used herein refer to the usual error range for the respective value readily known to the skilled person in this technical field. Reference to "about" a value or parameter herein includes (and describes) embodiments that are directed to that value or parameter per se. In some embodiments, the term "about" refers to ±10%, ±9%, ±8%, ±7%, ±6%, ±5%, ±4%, ±3%, ±2%, ±1% of a given value. However, whenever the value in question refers to an indivisible object, such as a molecule or other object that would lose its identity once subdivided, then "about" refers to ±1 of the indivisible object.

The term "antigen" comprises any molecule, for example a peptide, a protein, a polysaccharide or a glycoconjugate, which comprises at least one epitope that will elicit an immune response and/or against which an immune response is directed. For example, an antigen is a molecule which, optionally after processing, induces an immune response, which is for example specific for the antigen or cells expressing the antigen. After processing, an antigen may be presented by MHC molecules and reacts specifically with T lymphocytes (T cells). Thus, an antigen or fragments thereof should be recognizable by a T cell receptor and should be able to induce in the presence of appropriate co-stimulatory signals, clonal expansion of the T cell carrying the T cell receptor specifically recognizing the antigen or fragment, which results in an immune response against the antigen or cells expressing the antigen. According to the present disclosure, any suitable antigen may be envisioned which is a candidate for an immune response. An antigen may correspond to or may be derived from a naturally occurring antigen.

It is understood that aspects and embodiments of the present disclosure described herein include "having," "comprising," "consisting of," and "consisting essentially of" aspects and embodiments. The words "have" and "comprise," or variations such as "has," "having," "comprises," or "comprising," will be understood to imply the inclusion of the stated element(s) (such as a composition of matter or a method step) but not the exclusion of any other elements. The term "consisting of" implies the inclusion of the stated element(s), to the exclusion of any additional elements. The term "consisting essentially of" implies the inclusion of the stated elements, and possibly other element(s) where the other element(s) do not materially affect the basic and novel characteristic(s) of the disclosure. It is understood that the different embodiments of the disclosure using the term "comprising" or equivalent cover the embodiments where this term is replaced with "consisting of" or "consisting essentially of".

The phrase "a disease caused by a strain of *Neisseria meningitidis*" encompasses any clinical symptom or combination of clinical symptoms that are present in an infection of a human with *Neisseria meningitidis*. These symptoms include but are not limited to: colonization of the upper respiratory tract (e.g., mucosa of the nasopharynx and tonsils) by a pathogenic strain of *Neisseria meningitidis*, penetration of the bacteria into the mucosa and the submucosal vascular bed, septicemia, septic shock, inflammation, hemorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischemia, respiratory distress syndrome, pericarditis and meningitis.

As used herein, the terms "individual" or "subject" or "patient" are used interchangeably and intends to refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In some exemplary embodiments, the individual or subject is a human.

In the context of the disclosure, the expression "pharmaceutically acceptable carrier" refers to a carrier or vehicle that is physiologically acceptable for administration to a mammal, such as a human being, while retaining the physiological activity of the immunogenic composition as disclosed herein, i.e., its ability to induce an immune response with a low reactogenic effect.

As used herein, the terms "prevent", "preventing" or "delay progression of" (and grammatical variants thereof) with respect to a disease or disorder relate to prophylactic treatment of the disease or the disorder, e.g., in an individual suspected to have the disease, or at risk for developing the disease. Prevention may include, but is not limited to, preventing or delaying onset or progression of the disease and/or maintaining one or more symptoms of the disease or disorder at a desired or sub-pathological level. The term "prevent" does not require the 100% elimination of the possibility or likelihood of occurrence of the event. Rather, it denotes that the likelihood of the occurrence of the event has been reduced in the presence of a composition or method as described herein.

The term "protective immunity" means that a vaccine or immunization schedule that is administered to a mammal induces an immune response that prevents, retards the development of, or reduces the severity of a disease that is caused by *Neisseria meningitidis*, or diminishes or altogether eliminates the symptoms of the disease. Protective immunity can be accompanied by production of bactericidal antibodies. It should be noted that production of bactericidal antibodies against *Neisseria meningitidis* is accepted in the field as predictive of a vaccine's protective effect in humans. (Goldschneider et al. (1969) J. Exp. Med. 129:1307).

Within the disclosure, the term "significantly" used with respect to change intends to mean that the observe change is noticeable and/or it has a statistic meaning.

Within the disclosure, the term "substantially" used in conjunction with a feature of the disclosure intends to define a set of embodiments related to this feature which are largely but not wholly similar to this feature. The difference between the set of embodiments related to a given feature and the given feature is such that in the set of embodiments, the nature and function of the given feature is not materially affected.

The phrase "in a sufficient amount to elicit an immune response" or "immunologically effective amount" used with regard to an antigen or a combination of an antigen and an adjuvant, intend to refer to an amount which, when administered to a subject, is effective for eliciting an immune response against the antigen. This amount may vary depending various factors, such as the health or physical condition of the subject, its age, the capacity of the subject's immune system to produce antibodies, the degree of protection desired, the formulation of the composition containing the antigen, the treating doctor's assessment of the medical situation. This amount may be determined by routine methods known to the skilled person. Immune response indicators include but are not limited to: antibody titer or specificity, as detected by an assay such as enzyme-linked immunoassay (ELISA), bactericidal assay, flow cytometry, immunoprecipitation, Ouchterlony immunodiffusion; binding detection assays of, for example, spot, Western blot or antigen arrays; cytotoxicity assays, etc.

As used herein, in the context of an immune response elicitation, the terms "treat", "treatment", "therapy" and the like refer to the administration or consumption of a composition as disclosed herein with the purpose to cure, heal, alleviate, relieve, alter, remedy, ameliorate, improve, or affect a disease or a disorder, the symptoms of the condition, or to prevent or delay the onset of the symptoms, complications, or otherwise arrest or inhibit further development of the disorder in a statistically significant manner. Also, as used herein, in the context of the present disclosure, the terms "treat", "treatment" and the like refer to relief from or alleviation of pathological processes mediated by *Neisseria meningitidis* infection. In the context of the present disclosure, insofar as it relates to any of the other conditions recited herein, the terms "treat", "treatment", and the like refer to relieving or alleviating one or more symptoms associated with such condition.

As used herein, the term "vaccine" is intended to mean an immunogenic composition directed to a pathogen agent which is administered to a subject to induce an immune response with the intent to protect or treat the subject from an illness caused by the pathogen agent. A vaccine as disclosed herein is intended for use as a preventive (prophylactic) vaccine, for administration to a subject prior to infection, with the intent to prevent, or reduced the likelihood of occurrence of, initial (and/or recurrent) infection.

As used herein, the term "messenger RNA" or "mRNA" refers to a polynucleotide that encodes at least one polypeptide. mRNA, as used herein, encompasses both modified and unmodified RNA. mRNA may comprise one or more coding and non-coding regions. A coding region is alternatively referred to as an open reading frame (ORF). Non-coding regions in mRNA include the 5' cap, 5' untranslated region (UTR), 3' UTR, and a poly(A) tail. mRNA can be purified from natural sources, produced using recombinant expression systems (e.g., in vitro transcription) and optionally purified, or chemically synthesized.

The mRNA disclosed herein may be modified or unmodified. In some embodiments, the mRNA comprises at least one chemical modification. In some embodiments, the mRNA disclosed herein may comprise one or more modifications that typically enhance RNA stability. Exemplary modifications can include backbone modifications, sugar modifications, or base modifications. In some embodiments, the disclosed mRNA may be synthesized from naturally occurring nucleotides and/or nucleotide analogues (modified nucleotides) including, but not limited to, purines (adenine (A) and guanine (G)) or pyrimidines (thymine (T), cytosine (C), and uracil (U)). In certain embodiments, the disclosed mRNA may be synthesized from modified nucleotide analogues or derivatives of purines and pyrimidines, such as, e.g., 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxy acetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, β-D-mannosyl-queosine, phosphoramidates, phosphorothioates, peptide nucleotides, methylphosphonates, 7-deazaguanosine, 5-methylcytosine, and inosine.

In some embodiments, the disclosed mRNA may comprise at least one chemical modification including, but not limited to, pseudouridine, N1-methylpseudouridine, 2-thiouridine, 4'-thiouridine, 5-methylcytosine, 2-thio-I-methyl-1-deaza-pseudouridine, 2-thio-I-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methyluridine, 5-methyluridine, 5-methoxyuridine, and 2'-O-methyl uridine.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention. All publications mentioned herein are incorporated herein by reference to disclose and describe the methods and/or materials in connection with which the publications are cited.

The list of sources, ingredients, and components as described hereinafter are listed such that combinations and mixtures thereof are also contemplated and within the scope herein.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All lists of items, such as, for example, lists of ingredients, are intended to and should be interpreted as Markush groups. Thus, all lists can be read and interpreted as items "selected from the group consisting of" the list of items "and combinations and mixtures thereof."

Referenced herein may be trade names for components including various ingredients utilized in the present disclosure. The inventors herein do not intend to be limited by materials under any particular trade name. Equivalent materials (e.g., those obtained from a different source under a different name or reference number) to those referenced by trade name may be substituted and utilized in the descriptions herein.

Antigens

The immunogenic compositions as disclosed herein comprise at least a combination of meningococcal antigens. The combination of antigens may comprise at least one factor H binding protein (fHBP) A protein, at least one fHBP B protein, at least one *Neisseria* adhesin A (NadA) protein, and at least one detergent-extracted Outer Membrane Vesicle (dOMV).

In one embodiment, the meningococcal antigens may be from a *Neisseria meningitidis* serogroup B.

fHBP

The meningococcal fHBP also referred to in the art as lipoprotein 2086 (LP2086), ORF2086, Genome-derived Neisserial antigen (GNA) 1870, or "741", is a lipoprotein expressed at the bacterial surface of almost all invasive meningococcal isolates. fHBP is an important virulence factor as it binds human complement factor H (fH), a negative regulator of the alternative complement pathway (Seib et al., *Expert Rev Vaccines*. 2015; 14(6):841-59). The binding of fHBP to human fH enables the pathogen to escape alternative complement-mediated killing by the host innate immune system and to survive in human serum and blood.

Three major genetic and immunological fHBP variants have been described: variant 1, corresponding to subfamily B, and variants 2 and 3, both classified in subfamily A (Seib et al., *Expert Rev Vaccines*. 2015; 14(6):841-59). Further to the nomenclature provided by Pfizer (fHBP A and B) and Novartis (variants 1, 2 and 3), fHBPs are identified in the PubMLST database with a unique ID number. Although there is significant antigenic variability between fHBP subfamilies A and B, protein sequences within a subfamily are highly conserved with >86% sequence identity, among different strains. Each unique fHBP found in *N. meningitidis* is also assigned a fHBP peptide ID according to neisseria.org or pubmlst.org/neisseria/fHBP/website. Because the length of variant 2 (v.2) fHBP protein (from strain 8047, fHBP ID 77) and variant 3 (v.3) fHBP (from strain M1239, fHBP ID 28) differ by −1 and +7 amino acid residues, respectively, from that of MC58 (fHBP ID 1), the numbering used to refer to residues for v.2 and v.3 fHBP proteins differ from numbering based on the actual amino acid sequences of these proteins. Thus, for example, reference to a leucine residue (L) at position 166 of the v.2 or v.3 fHBP sequence refers to the residue at position 165 of the v.2 protein and at position 173 in the v.3 protein. Members of variants 1, 2 and 3 are present in approximately 65, 25 and 10% of the MenB clinical isolates causing invasive diseases, respectively. The ten most prevalent fHBP variants represented in the MenB strain global population account for approximately 80% of the invasive disease-causing strains in the United States and Europe combined (Bambini et al., *Vaccine*. 2009; 27(21): 2794-803; Chang, *J Infect* 2019; S0163-4453(19):30272-5; Lucidarme, *Clin Vaccine Immunol* 2010; 17(6):919-29; and Murphy et al., The *Journal of infectious diseases.* 2009; 200(3):379-89; Wang et al., *Vaccine*. 2011; 29(29-30):4739-44).

The fHBPs to be used according to the present disclosure may be wild-type (or naturally occurring) polypeptides or may be modified by amino acid substitutions, insertions, or deletions (non-naturally occurring), provided that the polypeptide can elicit an immune response.

The fHBPs to be used according to the present disclosure may be lipidated or non-lipidated fHBPs. Lipidated proteins usually comprise in their N-terminus sequence a specific peptide sequence for the lipidation. This sequence may be cleaved during the maturation stage of the protein. Those lipidation signal peptides are specific to each kind of proteins and to the cells of the host producing the protein.

ORF2086 polypeptide is expressed in *N. meningitidis* as a precursor protein having a lipoprotein signal motif. During processing, the motif is cleaved to leave an N-terminal cysteine residue that is co-translationally modified with a lipid anchor that tethers the protein to the neisserial outer membrane (McNeil et al. (2013) MMBR 77(2):234-252).

To avoid lipidation of a recombinant protein, various techniques known in the art can be used. As example, it may be possible to delete the lipidation peptide signal or to replace the lipidation peptide signal with another peptide signal not recognized by the cells in which the protein is produced. U.S. Pat. No. 10,300,122 B2 describes the use of this technique for ORF 2086.

It is also possible to either substituting the codon coding for the N-terminal cysteine with a codon coding for another amino acid or to remove the codon coding for the N-terminal cysteine. For example, regarding fHBPs, U.S. Pat. No. 10,300,122 B2 describes the fusion of an ATG (methionine) codon directly to the second 5' terminal codon of the ORF2086 coding for the mature polypeptide resulting in deleting the cysteine lipidation site (or substituting the cysteine by the methionine). Also, for example, U.S. Pat. No. 9,724,402 B2 or U.S. Pat. No. 11,077,180 B2 disclose the obtaining of non-lipidated fHBP where the N-terminal Cys is substituted with an amino acid that is not a Cys residue.

The fHBPs to be used according to the present disclosure may be naturally occurring or non-naturally occurring proteins. Non-naturally occurring proteins refers to "man-made proteins" and encompass fHBP with heterologous components that are not found in nature by opposition to naturally occurring proteins. Non-naturally occurring proteins may be chimeric proteins or mutated proteins. "Chimeric proteins" in the context of the present disclosure intends to refer to protein comprising two or more different components, each derived from a different fHBP (e.g., variant 1, 2, or 3). Mutations in a mutated protein may include amino acid substitution, insertion, or deletion. In one embodiment, a mutation is an amino acid substitution.

Non-naturally occurring fHBPs suitable for the immunogenic compositions as disclosed herein are still able to elicit an immune response against fHBPs. In one embodiment, the non-naturally occurring fHBPs to be used according to the present disclosure may be mutated fHBPs. Mutations, such as amino acids substitutions, may be introduced in order to reduce or suppress the binding of the fHBP antigen to the factor H (fH) of the coagulation normally present in the blood of an individual. The prevention of the binding of fH to the fHBP antigens used in the immunogenic compositions of the disclosure therefore may increase the amounts of antigens accessible to the immune system and improve the efficacy and efficiency of the immune response towards those antigens. Advantageously, the mutated fHBP may elicit an anti-fHBP antibody repertoire directed at fHBP epitopes within the fH binding site, which resulted in greater protective complement deposition activity than the antibodies elicited by the wild-type (WT) fHBP antigens, which targeted fHBP epitopes outside of the fH binding site.

The non-naturally occurring fHBPs considered for the immunogenic compositions as disclosed herein may present a reduced affinity towards fH compared to the corresponding naturally occurring fHBP or an improved thermal stability. Affinity towards fH protein and thermal stability may be measured as disclosed in WO 2016/014719 A1 (as in Examples 1 or 3 of this document).

For convenience and clarity, except otherwise specifically indicated, the native, or naturally occurring, amino acid sequence of fHBP B24 (or fHBP ID 1 or v.1 fHBP of the N. meningitidis strain MC58) of sequence SEQ ID NO:6 is selected as a reference sequence for all naturally occurring and non-naturally occurring fHBP amino acid sequences herein. Therefore, in referring to an amino acid residue position in a fHBP, the position number used herein corresponds to the amino acid residue number of SEQ ID NO:6 (fHBP B24). Consequently, position number 1 refers to the first amino acid residue shown in SEQ ID NO:6, which is a cysteine. This is still true even in case where further amino acids would be added at the N-terminus of SEQ ID NO:6, before this cysteine.

In one embodiment, a mutation, as for example an amino acid substitution, which may be introduced in a fHBP A or B antigens to be used within the present disclosure may be as disclosed in WO 2011/126863 A1, WO 2015/017817 A1, or WO 2016/014719 A1.

Immunogenic compositions as disclosed herein may comprise non-naturally occurring fHBPs that differ in amino acid sequence from a wild-type N. meningitidis fHBP by from 1 to 10 amino acids (e.g., by from 1, 2, 3, 4, 5, 6, 7, 8, 9, or 10 amino acids), from 10 amino acids to 15 amino acids, from 15 amino acids to 20 amino acids, from 20 amino acids to 30 amino acids, from 30 amino acids to 40 amino acids, or from 40 amino acids to 50 amino acids.

In some embodiments, a fHBP may comprise an amino acid sequence having at least about 80%, at least about 85%, at least about 90%, at least about 95%, at least about 98%, at least about 99%, or at least about 99.5%, amino acid sequence identity to a reference fHBP sequence.

Identity (e.g., percent homology) may be determined using various known sequence comparison tools, such as any homology comparison software computing a pairwise sequence alignment, including for example, the Blast software of the National Center of Biotechnology Information (NCBI), such as by using default parameters. The identity is a global identity, i.e., an identity over the entire amino acid or nucleic acid sequences and not over portions thereof. Pairwise global alignment was defined by Needleman et al., Journal of Molecular Biology, 1970, pages 443-53, volume 48). For example, when starting from a polypeptide sequence and comparing to other polypeptide sequences, the EMBOSS-6.0.1 Needleman-Wunsch algorithm (available from http://emboss.sourceforge.net/apps/cvs/emboss/apps/needle.html) may be used to find the optimum alignment of two sequences along their entire length—a "Global alignment".

fHBP antigens to be used in immunogenic compositions disclosed herein may be obtained as disclosed in WO 2016/014719 A1. The fHBPs may be obtained as recombinant proteins from recombinant expression vectors (or constructs) transfected into a host cell for production, for example an E coli strain. Suitable vectors for transferring and expressing fHBP-encoding nucleic acid may vary in composition. Integrative vectors can be conditionally replicative or suicide plasmids, bacteriophages, and the like.

A construct may include various elements, including for example, promoters, selectable genetic markers (e.g., genes conferring resistance to antibiotics (for instance kanamycin, erythromycin, chloramphenicol, or gentamycin)), origin of replication (to promote replication in a host cell, e.g., a bacterial host cell), and the like. The choice of vector will depend upon a variety of factors such as the type of cell in which propagation is desired and the purpose of propagation. Certain vectors are useful for amplifying and making large amounts of the desired DNA sequence. Other vectors are suitable for expression in cells in culture. The choice of appropriate vector is well within the skill of the art. Many such vectors are available commercially.

In one example, a vector may be an expression vector based on episomal plasmids comprising selectable drug resistance markers and elements that provide for autonomous replication in different host cells (e.g., in both E. coli and N. meningitidis). One example of such a "shuttle vector" is the plasmid pFPIO (Pagotto et al. (2000) Gene 244: 13-19). Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding the subject fHBP, may provide for propagating the subject nucleic acids, or both.

Examples of vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. pET21 is also an expression vector that may be used. Bacteriophage vectors may include λgtl0, λgtl1, λgtl8-23, λZAP/R and the EMBL series of bacteriophage vectors. Further vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

A recombinant expression vector may comprise a nucleotide sequence encoding an fHBP operably linked to a transcriptional control element, e.g., a promoter. A promoter may be constitutive or inducible. A promoter may be adapted for use in a prokaryotic host cell or in a eukaryotic host cell.

An expression vector provides transcriptional and translational regulatory sequences, and may provide for inducible or constitutive expression, where the coding region is operably linked under the transcriptional control of the transcriptional initiation region, and a transcriptional and translational termination region. These control regions may be native to an fHBP from which the subject fHBP is derived or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like).

Expression vectors generally have convenient restriction sites located near the promoter sequence to provide for the insertion of nucleic acid sequences encoding proteins of interest. Constructs (recombinant vectors) can be prepared by, for example, inserting a polynucleotide of interest into a construct backbone, typically by means of DNA ligase attachment to a cleaved restriction enzyme site in the vector. Alternatively, the desired nucleotide sequence can be inserted by homologous recombination or site-specific recombination. Typically, homologous recombination may be accomplished by attaching regions of homology to the vector on the flanks of the desired nucleotide sequence, while site-specific recombination can be accomplished through use of sequences that facilitate site-specific recombination (e.g., cre-lox, att sites, etc.). Nucleic acid comprising such sequences can be added by, for example, ligation of oligonucleotides, or by polymerase chain reaction using primers comprising both the region of homology and a portion of the desired nucleotide sequence.

In addition, the expression construct may include additional elements. For example, the expression vector may have one or two replication systems, thus allowing it to be maintained in organisms, for example in mammalian or insect cells for expression and in a prokaryotic host for cloning and amplification. In addition, the expression construct may comprise a selectable marker gene to allow the selection of transformed host cells. Selection genes are well known in the art and will vary with the host cell used.

Amino acid substitutions may be introduced in the fHBP nucleotide sequences by any techniques known in the art. For example, the amino acid substitutions may be obtained as disclosed in WO 2011/126863 A1, WO 2015/017817 A1, or WO 2016/014719 A1. In other exemplary embodiments, the amino acids substitution may be obtained as disclosed in WO 2015/128480, WO 2010/046715, WO 2016/008960, WO 2020/030782, or WO 2011/051893.

Recombinant fHBPs may be obtained in purified form from culture by any purification methods known in the art, as for example described in the Examples section.

In one embodiment, a fHBP A protein and/or a fHBP B may be present in immunogenic compositions as disclosed herein in an amount from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose. In one embodiment, a fHBP A protein and/or a fHBP B may be present in an amount at about 25 μg/dose, or at about 50 μg/dose, or at about 100 μg/dose.

fHBP A

In one embodiment, an immunogenic composition as disclosed herein may comprise at least one fHBP A variant antigen. The at least one fHBP A protein may be a lipidated or a non-lipidated protein. In one exemplary embodiment, an fHBP A protein may be a non-lipidated protein.

In one embodiment, a fHBP A protein may be a naturally or a non-naturally occurring fHBP. In one embodiment, a fHBP A protein may be a naturally occurring fHBP. In another embodiment, a fHBP A protein may be a non-naturally occurring fHBP.

In one embodiment, a fHBP A protein may be a protein comprising at least about 85%, at least about 90%, at least about 95%, at least about 98%, at least about 99%, at least about 99.5% or about 100% amino acid sequence identity to SEQ ID NO: 1. The at least one fHBP A protein may be a lipidated or a non-lipidated protein and/or may be a naturally or a non-naturally occurring fHBP (a non-naturally occurring fHBP A05 protein is not 100% identical to fHBP A05 or SEQ ID NO: 1).

A non-naturally occurring fHBP A protein may be a chimeric protein as disclosed in WO 2011/126863 A1 or WO 2015/017817 A1 or a mutated fHBP A protein as disclosed in WO 2016/014719 A1, WO 2011/051893, WO 2016/008960 or WO 2015/128480. In one exemplary embodiment, a fHBP A protein may be a mutated protein.

In one exemplary embodiment, a non-naturally occurring fHBP A protein may be a mutated protein. A non-naturally occurring fHBP A protein may be a non-lipidated protein. In one exemplary embodiment, a fHBP A protein may be a non-naturally occurring, such as a mutated, non-lipidated fHBP A protein.

In one embodiment, a non-naturally occurring fHBP A protein may differ in amino acid sequence from a wild-type N. meningitidis fHBP A protein, such as fHBP A05, by from 1 to 10 amino acids (e.g., by from 1, 2, 3, 4, 5, 6, 7, 8, 9, or 10 amino acids), from 10 amino acids to 15 amino acids, from 15 amino acids to 20 amino acids, from 20 amino acids to 30 amino acids, from 30 amino acids to 40 amino acids, or from 40 amino acids to 50 amino acids.

In one embodiment, a non-naturally occurring fHBP A protein may be a mutated protein comprising at least about 85%, at least about 90%, at least about 95%, at least about 98%, or at least about 99%, or at least about 99.5% amino acid sequence identity to SEQ ID NO: 1. A non-naturally occurring fHBP A05 protein is not 100% identical to fHBP A05 or SEQ ID NO: 1.

In another embodiment, a non-naturally occurring, or mutated, fHBP A protein may comprise at least one amino acid substitution selected from at least one of: a) an amino acid substitution of the asparagine at amino acid 115 (N115); b) an amino acid substitution of the aspartic acid at amino acid 121 (D121); c) an amino acid substitution of the serine at amino acid 128 (S128); d) an amino acid substitution of the leucine at amino acid 130 (L130); e) an amino acid substitution of the valine at position 131 (V131); f) an amino acid substitution of the glycine at position 133 (G133); g) an amino acid substitution of the lysine at position 219 (K219); and h) an amino acid substitution of the glycine at position 220 (G220), based on the numbering of SEQ ID NO:6.

In another embodiment, a non-naturally occurring, or mutated, fHBP A protein may comprise at least one amino acid deletion or substitution in any one of the following positions as disclosed in WO 2011/051893 with regard to the numbering of the fHBP sequence identified as SEQ ID NO: 5 in WO 2011/051893 (mature lipoprotein form of fHBP A19): D37, K45, T56, E83, E95, E112, S122, I124, R127, T139, F141, N142, Q143, L197, D210, R212, K218, N43, N116, K119, T220 and/or 240. In one embodiment, the amino acid deletion or substitution is/are as disclosed in WO 2011/051893.

In another embodiment, a non-naturally occurring, or mutated, fHBP A protein may comprise at least one amino acid deletion or substitution in any one of the following positions as disclosed in WO 2016/008960 with regard to the numbering of the fHBP sequence identified as SEQ ID NO: 17 in WO 2016/008960 (A124 or variant 3.28 or ID28): S32, L126 and/or E243. One, two or three residues may be deleted. Alternatively, they may be substituted by a different amino acid. For example, Leu-126 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g., it is made within the following four groups: (1) acidic i.e., aspartate, glutamate; (2) basic i.e., lysine, arginine, histidine; (3) non-polar i.e., alanine, valine, leucine, isoleucine, proline, phenylalanine, methionine, tryptophan; and (4) uncharged polar i.e., glycine, asparagine, glutamine, cysteine, serine, threonine, tyrosine. In other embodiments the substitution is non-conservative. In one embodiment, substitutions at the specified residues are as follows: S32V; L126R; and/or E243A.

In another embodiment, a non-naturally occurring, or mutated, fHBP A protein may comprise at least one amino acid deletion or substitution in any one of the following positions as disclosed in WO 2016/008960 with regard to the numbering of the fHBP sequence identified as SEQ ID NO: 5 in WO 2016/008960 (mature lipoprotein form): S32, L123 and/or E240. One, two or three residues may be deleted. Alternatively, they may be substituted by a different amino acid. For example, Leu-123 can be substituted by any of the other 19 naturally-occurring amino acids. When a substitution is made, the replacement amino acid in some embodiments may be a simple amino acid such as glycine or alanine. In other instances, the replacement amino acid is a conservative substitution e.g., it is made within the following four groups: (1) acidic i.e., aspartate, glutamate; (2) basic i.e., lysine, arginine, histidine; (3) non-polar i.e., alanine, valine, leucine, isoleucine, proline, phenylalanine, methionine, tryptophan; and (4) uncharged polar i.e., glycine, asparagine, glutamine, cysteine, serine, threonine, tyrosine. In other embodiments the substitution is non-conservative. In one embodiment, the substitutions at the specified residues may be as follows: S32V; L123R; and/or E240A.

In another embodiment, a non-naturally occurring, or mutated, fHBP A protein may comprise at least one amino acid deletion or substitution in any one of the following positions as disclosed in WO 2015/128480 with regard to the numbering of the fHBP sequence identified as SEQ ID NO: 5 in WO 2015/128480 (fHBP A19 or v2.16 or ID16): S32, V33, L39, L41, F69, V100, I113, F122, L123, V124, S125, G126, L127, G128, S151, H239, and/or E240. In one embodiment, residues for mutation may be S32, V100, L123, V124, S125, G126, L127, G128, H239, and/or E240. Mutations at these residues give proteins having good stability compared to wild-type fHBP A. In one embodiment, residues for mutations may be S32, L123, V124, S125, G126, L127, and/or G128. In one embodiment, residues for mutations may be S32, L123, V124, S125, G126, L127, and/or G128. In another embodiment, residues S32 and/or L123 may be mutated, e.g., S32V and/or L123. Where one or more of V100, S125, and/or G126 is mutated, mutation of a residue outside this trio may be also introduced.

The specified residue can be deleted, but preferably it is substituted by a different amino acid. For example, Ser-32 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g., it is made within the following four groups: (1) acidic i.e., aspartate, glutamate; (2) basic i.e., lysine, arginine, histidine; (3) non-polar i.e., alanine, valine, leucine, isoleucine, proline, phenylalanine, methionine, tryptophan; and (4) uncharged polar i.e., glycine, asparagine, glutamine, cysteine, serine, threonine, tyrosine. In other embodiments the substitution is non-conservative. In some embodiments the substitution does not use alanine.

As for example, substitutions at the specified residues may be as follows: S32V; V33C; L39C; L41C; F69C; V100T; I113S; F122C; L123R; V124I; S125G or S125T; G126D; L127I; G128A; S151C; H239R; or E240H.

In another embodiment, a non-naturally occurring, or mutated, fHBP A protein may comprise at least one amino acid deletion or substitution in any one of the following positions as disclosed in WO 2015/128480 with regard to the numbering of the fHBP sequence identified as SEQ ID NO: 17 in WO 2015/128480 (A124 or variant 3.28 or ID28): S32, V33, L39, L41, F72, V103, T116, F125, L126, V127, S128, G129, L130, G131, S154, H242, and/or E243. In one embodiment, residues for mutation may be S32, V103, L126, V127, S128, G129, L130, G131, H242, and/or E243. In one embodiment, residues for mutations may be S32, L126, V127, S128, G129, L130, and/or G131. In another embodiment, residues S32, L126, V127, S128, G129, L130, and/or G131 may be mutated, as for example residues S32 and/or L126 e.g., S32V and/or L126R.

The specified residue can be deleted, but preferably it is substituted by a different amino acid. For example, Ser-32 can be substituted by any of the other 19 naturally-occurring amino acids. When a substitution is made, the replacement amino acid in some embodiments may be a simple amino acid such as glycine or alanine. In other embodiments, the replacement amino acid is a conservative substitution e.g., it is made within the following four groups: (1) acidic i.e., aspartate, glutamate; (2) basic i.e., lysine, arginine, histidine; (3) non-polar i.e., alanine, valine, leucine, isoleucine, proline, phenylalanine, methionine, tryptophan; and (4) uncharged polar i.e., glycine, asparagine, glutamine, cysteine, serine, threonine, tyrosine. In other embodiments the substitution is non-conservative. In some embodiments the substitution does not use alanine.

As for example, substitutions at the specified residues may be as follows: S32V; I33C; L39C; L41C; F72C; V103T; T116S; F125C; L126R; V127I; S128G or S128T; G129D; L130I; G131A; S154C; H242R; E243H.

An amino acid substitution of the asparagine at amino acid 115 (N115) may be a N115I substitution (I: isoleucine). Other amino acids with non-polar, positively charged or aromatic side chains, such as valine, leucine, lysine, arginine, histidine, phenylalanine, tyrosine or tryptophan, also may be substituted at this position. Thus, in some cases, the fHBP may comprise an N115V substitution, an N115L substitution, an N115K substitution, an N115R substitution, an N115H substitution, an N115F substitution, an N115Y substitution, or an N115W substitution.

An amino acid substitution of the aspartic acid at amino acid 121 (D121) may be a D121G substitution (G: glycine). Other amino acids with non-polar, positively charged or aromatic side chains, such as leucine, isoleucine, valine, lysine, arginine, histidine, phenylalanine, tyrosine or tryptophan, also may be substituted at this position. Thus, for example, in some cases the fHBP variant may comprise a D121L substitution, a D121I substitution, a D121V substitution, a D121K substitution, a D121R substitution, a D121H substitution, a D121F substitution, a D121Y substitution, or a D121W substitution.

An amino acid substitution of the serine acid at amino acid 128 (S128) may be a S128T substitution (T: threonine). Other amino acids with polar, charged or aromatic side chains, such as methionine, asparagine, glutamine, aspartate, glutamate, lysine, arginine, histidine, phenylalanine, tyrosine or tryptophan, also may be substituted at this position. Thus, for example, in some cases the fHBP variant may comprise an S128M substitution, an S128N substitution, an S128D substitution, an S128E substitution, an S128K substitution, an S128R substitution, an S128H substitution, an S128F substitution, an S128Y substitution, or an S128W substitution.

A fHBP A may comprise an amino acid substitution of the leucine at amino acid 130 (L130). An amino acid substitution of the leucine at amino acid 130 (L130) may be a L130R substitution (R: arginine).

A fHBP A may comprise an amino acid substitution of the valine at amino acid 131 (V131). Other amino acids with charged or aromatic side chains, such as glutamate, lysine, arginine, histidine, phenylalanine, tyrosine or tryptophan, also may be substituted at this position. Thus, for example, in some cases, the fHBP may comprise a V131E substitution, a V131K substitution, a V131R substitution, a V131H substitution, a V131F substitution, a V131Y substitution, or a V131W substitution.

A fHBP A may comprise an amino acid substitution of the glycine at amino acid 133 (G133). An amino acid substitution of the glycine at amino acid 133 (G133) may be a G133D substitution (D: aspartic acid).

A fHBP A may comprise an amino acid substitution of the lysine at position 219 (K219). Other amino acids with polar, negatively charged or aromatic side chains, such as glutamine, aspartate, glutamate, phenylalanine, tyrosine or tryptophan, also may be substituted at this position. Thus, for example, in some cases, the fHBP may comprise a K219Q substitution, a K219D substitution, a K219E substitution, a K219F substitution, a K219Y substitution, or a K219W substitution.

An amino acid substitution of the glycine acid at amino acid 220 (G220) may be a G220S substitution (S: serine). Other amino acids with polar, charged or aromatic side chains, such as asparagine, glutamine, aspartate, glutamate, lysine, arginine, histidine, phenylalanine, tyrosine or tryptophan, also may be substituted at this position. Thus, for example, in some cases, the fHBP may comprise a G220N substitution, a G220Q substitution, a G220D substitution, a G220E substitution, a G220K substitution, a G220R substitution, a G220H substitution, a G220F substitution, a G220Y substitution, or a G220W substitution.

In one exemplary embodiment, an amino acid substitution of the leucine at amino acid 130 (L130) may be a L130R substitution (R: arginine).

In one exemplary embodiment, an amino acid substitution of the glycine at amino acid 133 (G133) may be a G133D substitution (D: aspartic acid).

In one exemplary embodiment, an amino acid substitution of the glycine at position 220 (G220) may be a G220S substitution (S: serine).

In another embodiment, a non-naturally occurring, or mutated, fHBP A protein may comprise at least one of the amino acid substitutions selected in the group consisting of G220S, L130R, and G133D, based on the numbering of SEQ ID NO:6. In another embodiment, a non-naturally occurring fHBP A protein may comprise at least the three amino acid substitutions selected in the group consisting of G220S, L130R, and G133D, based on the numbering of SEQ ID NO:6. In another embodiment, a fHBP A protein may comprise only the three amino acid substitutions G220S, L130R, and G133D, based on the numbering of SEQ ID NO:6.

In one embodiment, a non-naturally occurring (or mutated) fHBP A protein may be a non-lipidated mutated fHBP A protein comprising at least one of the amino acid substitutions selected in the group consisting of a) an amino acid substitution of the asparagine at amino acid 115 (N115); b) an amino acid substitution of the aspartic acid at amino acid 121 (D121); c) an amino acid substitution of the serine at amino acid 128 (S128); d) an amino acid substitution of the leucine at amino acid 130 (L130); e) an amino acid substitution of the valine at position 131 (V131); f) an amino acid substitution of the glycine at position 133 (G133); g) an amino acid substitution of the lysine at position 219 (K219); and h) an amino acid substitution of the glycine at position 220 (G220), based on the numbering of SEQ ID NO:6.

In another embodiment, a non-naturally occurring (or mutated) fHBP A protein may be a non-lipidated mutated fHBP A protein comprising at least one of the amino acid substitutions selected in the group consisting of a N115I substitution, a N115V substitution, a N115L substitution, a N115K substitution, a N115R substitution, an N115H substitution, an N115F substitution, an N115Y substitution, an N115W substitution, a D121G substitution, a D121L substitution, a D121I substitution, a D121V substitution, a D121K substitution, a D121R substitution, a D121H substitution, a D121F substitution, a D121Y substitution, a D121W substitution, a S128T substitution, a S128M substitution, a S128N substitution, a S128D substitution, a S128E substitution, a S128K substitution, a S128R substitution, a S128H substitution, a S128F substitution, a S128Y substitution, a S128W substitution, a L130R substitution, a V131E substitution, a V131K substitution, a V131R substitution, a V131H substitution, a V131F substitution, a V131Y substitution, a V131W substitution, a G133D substitution, a K219Q substitution, a K219D substitution, a K219E substitution, a K219F substitution, a K219Y substitution, a K219W substitution, a G220S substitution, a G220N substitution, a G220Q substitution, a G220D substitution, a G220E substitution, a G220K substitution, a G220R substitution, a G220H substitution, a G220F substitution, a G220Y substitution, or a G220W substitution, based on the numbering of SEQ ID NO:6.

In one exemplary embodiment, a non-naturally occurring (or mutated) fHBP A protein may be a non-lipidated mutated fHBP A protein comprising at least one of the amino acid substitutions selected in the group consisting of G220S, L130R, and G133D, based on the numbering of SEQ ID NO:6. In another embodiment, a non-naturally occurring, or mutated, non-lipidated fHBP A protein may comprise at least the three amino acid substitutions selected in the group consisting of G220S, L130R, and G133D, based on the numbering of SEQ ID NO:6. In another exemplary embodiment, a non-lipidated mutated fHBP A protein may comprise only the three amino acid substitutions G220S, L130R, and G133D, based on the numbering of SEQ ID NO:6.

In one exemplary embodiment, a fHBP A protein may be a non-lipidated and mutated protein comprising at least about 85%, at least about 90%, at least about 95%, at least about 98%, at least about 99%, or at least about 99.5% amino acid sequence identity to SEQ ID NO: 1 and comprising at least one of the amino acid substitutions selected in the group consisting of G220S, L130R, and G133D, based on the numbering of SEQ ID NO:6. The mutated, non-lipidated fHBP A protein may comprise at least the three amino acid substitutions selected in the group consisting of G220S, L130R, and G133D, based on the numbering of SEQ ID NO:6. In another exemplary embodiment, the non-lipidated mutated fHBP A protein may comprise only the three amino acid substitutions G220S, L130R, and G133D, based on the numbering of SEQ ID NO:6.

In one embodiment a fHBP A protein may comprise at least about 85%, at least about 90%, at least about 95%, at least about 98%, at least about 99%, or at least about 99.5% amino acid sequence identity to SEQ ID NO: 2.

In another embodiment, a fHBP A protein may comprise or consist of SEQ ID NO: 2.

Another embodiment is directed to a mRNA coding for a fHBP A protein comprising at least about 85%, at least about 90%, at least about 95%, at least about 98%, at least about 99%, or at least about 99.5% amino acid sequence identity to SEQ ID NO: 2. The mRNA may code for a fHBP A protein comprising or consisting of SEQ ID NO:1 or code for a fHBP A protein comprising or consisting of SEQ ID NO: 2.

Amino acid substitutions may be introduced in the fHBP A nucleotide sequences by any techniques known in the art. For example, the amino acid substitutions may be obtained as disclosed in WO 2016/014719 A1.

In one embodiment, a fHBP A protein may be present in immunogenic compositions as disclosed herein in an amount from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose. In one embodiment, a fHBP A protein and/or a fHBP B may be present in an amount at about 25 μg/dose, or at about 50 μg/dose, or at about 100 μg/dose.

fHBP B

In one embodiment, an immunogenic composition as disclosed herein may comprised at least one fHBP B variant antigen. The at least one fHBP B protein may be a lipidated or a non-lipidated protein. In one exemplary embodiment, an fHBP B protein may be a non-lipidated protein.

In one embodiment, the fHBP A and the fHBP B proteins may be lipidated. In one embodiment, the fHBP A and the fHBP B proteins may be non-lipidated. Alternatively, the fHBP A proteins may be lipidated and the fHBP B proteins may be non-lipidated. Still alternatively, the fHBP A proteins may be non-lipidated and the fHBP B proteins may be lipidated.

In one embodiment, a fHBP B protein may be a naturally or a non-naturally occurring fHBP. In one embodiment, a fHBP B protein may be a naturally occurring fHBP. In another embodiment, a fHBP B protein may be a non-naturally occurring fHBP.

In one embodiment, the fHBP A and the fHBP B proteins may be naturally occurring fHBP. In one embodiment, the fHBP A and the fHBP B proteins may be non-naturally occurring fHBP. Alternatively, the fHBP A proteins may be naturally occurring fHBP and the fHBP B proteins may be non-naturally occurring fHBP. Still alternatively, the fHBP A proteins may be non-naturally occurring fHBP and the fHBP B proteins may be naturally occurring fHBP.

In one embodiment, a fHBP B protein may be a protein comprising at least about 85%, at least about 90%, at least about 95%, at least about 98%, at least about 99%, at least about 99.5% or about 100% amino acid sequence identity to SEQ ID NO: 3. The at least one fHBP B protein may be a lipidated or a non-lipidated protein and/or may be a naturally or a non-naturally occurring fHBP (a non-naturally occurring fHBP B01 protein is not 100% identical to fHBP B01 or SEQ ID NO: 3).

A non-naturally occurring fHBP B protein may be a chimeric protein as disclosed in WO 2011/126863 A1 or WO 2015/017817 A1 in or a mutated fHBP B protein as disclosed in WO 2016/014719 A1, WO 2011/051893, or in WO 2020/030782. In one exemplary embodiment, a fHBP B protein may be a mutated protein.

In one exemplary embodiment, a non-naturally occurring fHBP B protein may be a mutated protein. A non-naturally occurring fHBP B protein may be a non-lipidated protein. In one exemplary embodiment, a fHBP B protein may be a non-naturally occurring, such as a mutated, non-lipidated fHBP B protein.

In one embodiment, a non-naturally occurring fHBP B protein may differ in amino acid sequence from a wild-type N. meningitidis fHBP B protein, such as fHBP B01, by from 1 to 10 amino acids (e.g., by from 1, 2, 3, 4, 5, 6, 7, 8, 9, or 10 amino acids), from 10 amino acids to 15 amino acids, from 15 amino acids to 20 amino acids, from 20 amino acids to 30 amino acids, from 30 amino acids to 40 amino acids, or from 40 amino acids to 50 amino acids.

In one embodiment, a non-naturally occurring fHBP B protein may be a mutated protein comprising at least 8 about 5%, at least about 90%, at least about 95%, at least about 98%, or at least about 99%, or at least about 99.5% amino acid sequence identity to SEQ ID NO: 3. A non-naturally occurring fHBP B protein is not 100% identical to fHBP B01 or SEQ ID NO:3.

In another embodiment, a non-naturally occurring, or mutated, fHBP B protein may comprise at least one amino acid substitution selected from at least one of: a) an amino acid substitution of the glutamine at amino acid 38 (Q38); b) an amino acid substitution of the glutamic acid at amino acid 92 (E92); c) an amino acid substitution of the arginine at amino acid 130 (R130); d) an amino acid substitution of the serine at amino acid 223 (S223); and e) an amino acid substitution of the histidine at amino acid 248 (H248), based on the numbering of SEQ ID NO:6.

In another embodiment, a non-naturally occurring, or mutated, fHBP B protein may comprise at least one amino acid deletion or substitution in any one of the following positions as disclosed in WO 2011/051893 with regard to the numbering of the fHBP sequence identified as SEQ ID NO: 4 in WO 2011/051893 (mature lipoprotein form of fHBP B24): D37, K45, T56, E83, E95, E112, K122, V124, R127, T139, F141, D142, K143, I198, S211, L213, K219, N43, D116, H119, S221 and K241.

In another embodiment, a non-naturally occurring, or mutated, fHBP B protein may comprise at least one amino substitution in any one of the following positions as disclosed in WO 2020/030782 with regard to the numbering of the fHBP sequence identified as SEQ ID NO: 2 in WO 2020/030782 (mature lipoprotein form of fHBP B09): E211, S216 or E232.

In another embodiment, a non-naturally occurring, or mutated, fHBP B protein may comprise at least one of the following amino substitution in any one of the following positions as disclosed in WO 2020/030782 with regard to the numbering of the fHBP sequence identified as SEQ ID NO: 2 in WO 2020/030782 (mature lipoprotein form of fHBP B09): E211A, S216R or E232A.

In another embodiment, a non-naturally occurring, or mutated, fHBP B protein may comprise at least one amino substitution in any one of the following positions as disclosed in WO 2020/030782 with regard to the numbering of the fHBP sequence identified as SEQ ID NO: 6 in WO 2020/030782 (mature lipoprotein form of fHBP B44): E214, S219 or E235.

In another embodiment, a non-naturally occurring, or mutated, fHBP B protein may comprise at least one of the following amino substitution in any one of the following positions as disclosed in WO 2020/030782 with regard to the numbering of the fHBP sequence identified as SEQ ID NO: 2 in WO 2020/030782 (mature lipoprotein form of fHBP B44): E214A, S219R or E235A.

In another embodiment, a non-naturally occurring, or mutated, fHBP B protein may comprise at least one of the following amino substitution in any one of the following positions as disclosed in WO2010046715 with regard to the numbering of the fHBP sequence identified as SEQ ID NO: 1 in WO2010046715 (mature lipoprotein form of fHBP 24: 103, 106, 107, 108, 109, 145, 147, 149, 150, 154, 156, 157, 180, 181, 182, 183, 184, 185, 191, 193, 194, 195, 196, 199, 262, 264, 266, 267, 268, 272, 274, 283, 285, 286, 288, 289, 302, 304 306, 311 and 313. In one embodiment, one or more amino acids which may be changed in the factor H binding protein may be selected from the group comprising amino acid number 103, 106, 107, 108, 180, 181, 183, 184, 185, 191, 193, 195, 262, 264, 266, 272, 274, 283, 286, 304 and 306 with regard to the numbering of the fHBP sequence identified as SEQ ID NO: 1 in WO2010046715.

An amino acid substitution of the glutamine at amino acid 38 (Q38) may be a Q38R substitution (R: arginine). Other amino acids with positively charged or aromatic side chains, such as lysine, histidine, phenylalanine, tyrosine or tryptophan, also may be substituted at this position. Thus, in some cases, the fHBP may comprise a Q38K substitution, a Q38H substitution, a Q38F substitution, a Q38Y substitution, or a Q38W substitution.

An amino acid substitution of the glutamic acid at amino acid 92 (E92) may be a E92K substitution. Other amino acids with positively charged or aromatic side chains, such as arginine, histidine, phenylalanine, tyrosine or tryptophan, also may be substituted at this position. Thus, for example, in some cases the fHBP variant may comprise an E92R substitution, an E92H substitution, an E92F substitution, an E92Y substitution, or an E92W substitution.

An amino acid substitution of the arginine at amino acid 130 (R130) may be a R130G substitution (G: glycine). Other amino acids with negatively charged or aromatic side chains, such as aspartate, glutamate, phenylalanine, tyrosine, or tryptophan, may also be substituted at R130. Thus, for example, in some cases the fHBP variant may comprise an R130D substitution, an R130E substitution, an R130F substitution, an R130Y substitution, or an R130W substitution.

An amino acid substitution of the serine at amino acid 223 (S223) may be an S223R substitution (R: arginine). Other amino acids with positively charged or aromatic side chains, such as lysine, histidine, phenylalanine, tyrosine or tryptophan, also may be substituted at this position. Thus, for example, in some cases, the fHbp variant comprises an S223K substitution, an S223H substitution, an S223F substitution, an S223Y substitution, or an S223W substitution.

In one exemplary embodiment, an amino acid substitution of the histidine at amino acid 248 (H248) may be an H248L substitution (L: leucine). Other amino acids with non-polar, negatively charged or aromatic side chains, such as isoleucine, valine, aspartate, glutamate, phenylalanine, tyrosine or tryptophan, also may be substituted at H248. Thus, for example, in some cases, the fHBP may comprise an H248I substitution, an H248V substitution, an H248D substitution, an H248E substitution, an H248F substitution, an H248Y substitution, or an H248W substitution.

In another embodiment, a non-naturally occurring, or mutated, fHBP B protein may comprise at least the amino acid substitution H248L. In another embodiment, a non-naturally occurring fHBP B protein may comprise only the amino acid substitution H248L, based on the numbering of SEQ ID NO:6.

In one embodiment, a non-naturally occurring (or mutated) fHBP B protein may be a non-lipidated mutated fHBP B protein comprising at least one of the amino acid substitutions selected in the group consisting of a) an amino acid substitution of the glutamine at amino acid 38 (Q38); b) an amino acid substitution of the glutamic acid at amino acid 92 (E92); c) an amino acid substitution of the arginine at amino acid 130 (R130); d) an amino acid substitution of the serine at amino acid 223 (S223); and e) an amino acid substitution of the histidine at amino acid 248 (H248), based on the numbering of SEQ ID NO:6.

In another embodiment a non-naturally occurring (or mutated) fHBP B protein may be a non-lipidated mutated fHBP B protein comprising at least one of the amino acid substitutions selected in the group consisting of a Q38R substitution, a Q38K substitution, a Q38H substitution, a Q38F substitution, a Q38Y substitution, a Q38W substitution, a E92K substitution, a E92R substitution, a E92H substitution, a E92F substitution, a E92Y substitution, a E92W substitution, a R130G substitution, a R130D substitution, a R130E substitution, a R130F substitution, a R130Y substitution, a R130W substitution, a S223R substitution, a S223K substitution, a S223H substitution, a S223F substitution, a S223Y substitution, a S223W substitution, a H248L substitution, a H248I substitution, a H248V substitution, a H248D substitution, a H248E substitution, a H248F substitution, a H248Y substitution, or a H248W substitution, based on the numbering of SEQ ID NO:6.

In another exemplary embodiment, a non-naturally occurring, or mutated, fHBP B protein may be a non-lipidated mutated fHBP B protein comprising at least the amino acid substitution H248L, based on the numbering of SEQ ID NO:6. In another exemplary embodiment, a non-lipidated mutated fHBP B protein may comprise only the amino acid substitution H248L, based on the numbering of SEQ ID NO:6.

In one exemplary embodiment, a fHBP A protein may be a non-lipidated and mutated protein comprising at least about 85%, at least about 90%, at least about 95%, at least about 98%, or at least about 99% amino acid sequence identity to SEQ ID NO: 3 and comprising at least the amino acid substitution H248L, based on the numbering of SEQ ID NO:6. The non-lipidated mutated fHBP B protein may comprise only the amino acid substitution H248L, based on the numbering of SEQ ID NO:6.

In one embodiment a fHBP B protein may comprise at least about 85%, at least about 90%, at least about 95%, at least about 98%, at least about 99%, or at least about 99.5% amino acid sequence identity to SEQ ID NO: 4.

In another embodiment, a fHBP B protein may comprise or consist of SEQ ID NO: 4.

Another embodiment is directed to a mRNA coding for a fHBP B protein comprising at least about 85%, at least about 90%, at least about 95%, at least about 98%, at least about 99%, or at least about 99.5% amino acid sequence identity to SEQ ID NO: 4. The mRNA may code for a fHBP B protein comprising or consisting of SEQ ID NO:3 or code for a fHBP A protein comprising or consisting of SEQ ID NO: 4.

Amino acid substitutions may be introduced in the fHBP B nucleotide sequences by any techniques known in the art. For example, the amino acid substitutions may be obtained as disclosed in WO 2016/014719 A1.

In one embodiment, a fHBP B protein may be present in immunogenic compositions as disclosed herein in an amount from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose. In one embodiment, a fHBP A protein and/or a fHBP B may be present in an amount at about 25 μg/dose, or at about 50 μg/dose, or at about 100 μg/dose.

NadA

*Neisseria* adhesin A (NadA, previously known as GNA1994) is a surface-exposed trimeric protein forming oligomers anchored via a transmembrane domain into the outer membrane and plays a key role in adhesion and invasion to epithelial cells (Capecchi et al., *Mol. Microbiol.* 2005; 55:(687-98)). The sequences of NadA antigen from many strains have been published, and the protein's activity as a Neisserial adhesin has been well documented. The nadA gene is present in approximately 50% of meningococcal isolates. NadA exhibits growth-phase dependent expression, with maximal levels in the stationary growth phase.

The NadA antigen was included in the published genome sequence for meningococcal serogroup B strain MC58 as gene NMB1994 (GenBank accession number GI:7227256).

A NadA polypeptide for use according to the present disclosure may be wild-type polypeptide or may be modified by amino acid substitutions, insertions, or deletions, provided that the polypeptide can elicit an immune response against NadA.

In some embodiments, a NadA protein to be used may be a N-terminally and/or C-terminally truncated NadA or NadA proteins comprising amino acids deletions or insertions, for example as disclosed in references WO 01/64920; WO 01/64922; or WO 03/020756.

In one embodiment, a recombinant NadA protein to be used in an immunogenic composition as disclosed herein may be a NadA1 variant. As shown in the Examples, NadA1 was shown to induce a strong hSBA response.

NadA1 may be obtained from the NadA sequence of MenB MC58 strain.

In one embodiment, a NadA protein may comprise or consist of the sequence SEQ ID NO: 7.

In some embodiments, a NadA protein may comprise at least 190 consecutive amino acids from SEQ ID NO: 7, for example 200 or more, 210 or more, 220 or more, 230 or more, 240 or more, 250 or more consecutive amino acids from SEQ ID NO: 7, for example 260 or more, or 270 or more, or 280 or more, or 290 or more, or 300 or more, or 310 or more, or 320 or more, or 330 or more, or 340 or more, or 350 or more, or 360 or more amino acids from SEQ ID NO: 7.

In some embodiments, a NadA protein may lack from 5 to 10 amino acids, or from 10 to 15, or from 15 to 20, or 25, or 30 or 35, or 40 or 45, or 50 or 55 amino acids from the C-terminus and/or the N-terminus, for example of SEQ ID NO: 7. Where N-terminus residues are deleted, such deletion should not remove the ability of NadA to adhere to human epithelial cells.

In one embodiment, a NadA protein may lack the signal peptide at the N-terminus. For example, a NadA protein may lack 23 amino acids that the N-terminus, for example of SEQ ID NO: 7.

In one embodiment, a NadA protein may lack the membrane anchoring peptide at the C-terminus. For example, a NadA protein may lack 55 amino acids at the C-terminus, for example of SEQ ID NO: 7.

NadA may be used in a monomeric or an oligomeric form, for example in a trimeric form.

For example, a NadA protein may be without its C-terminal membrane anchor (e.g., deletion of residues 308-362 for strain MC58 (SEQ ID NO: 7)). Expression of NadA without its membrane anchor domain in *E. coli* may results in secretion of the protein into the culture supernatant with concomitant removal of the 23 amino acids signal peptide (e.g., deletion of residues 2 to 24 of SEQ ID NO: 7, to leave a 284 amino acids protein—SEQ ID NO: 5).

In one embodiment, a NadA protein may comprise at least about 85%, at least about 90%, at least about 95%, at least about 98%, at least about 99%, or at least about 99.5% amino acid sequence identity to SEQ ID NO: 5. In another embodiment, a NadA protein may comprise or consist of SEQ ID NO:5.

Another embodiment is directed to a mRNA coding for a NadA protein comprising at least about 85%, at least about 90%, at least about 95%, at least about 98%, at least about 99%, or at least about 99.5% amino acid sequence identity to SEQ ID NO: 5. The mRNA may code for a NadA protein comprising or consisting of SEQ ID NO: 5.

NadA proteins to be used in immunogenic compositions disclosed herein may be obtained according to any recombinant techniques known in the art, for example as generally above disclosed. The NadA proteins may be obtained as recombinant proteins from recombinant expression vectors (or constructs) transfected into a host cell for production, for example an *E coli* strain. Recombinant NadA may be obtained in purified form from culture by any purification methods known in the art, as for example described in the Examples section.

In one embodiment, a NadA protein may be present in an amount ranging from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose. In one embodiment, a NadA protein may be present in an or at about 50 μg/dose.

dOMV

Immunogenic compositions as disclosed herein comprise a detergent-extracted Outer Membrane Vesicle (dOMV), also referred to as Outer Membrane Protein Complex (OMPC). Usually, the detergent-extracted Outer Membrane Vesicles are referred to as dOMV or OMV when used as antigens. They are referred to as OMPC when used as protein carrier.

OMPC was used as carrier protein platform for the polyribosylribitol phosphate (PRP) conjugate vaccine PedvaxHIB (*Haemophilus influenzae* type b vaccine) (Einhorn et al., *Lancet* (London, England). 1986; 2(8502):299-302; Moro et al., *The Journal of pediatrics.* 2015; 166(4): 992-7) and for VAXELIS (diphtheria, tetanus, pertussis, poliomyelitis, hepatitis B and *H. influenzae* type b vaccine) (Syed, *Paediatric drugs.* 2017; 19(1):69-80).

dOMV are large proteolipid vesicles comprising integral outer member protein found in the bacteria's outer membrane and residual lipo-oligosaccharide (LOS) (Helting, *Acta Pathol Microbiol Scand C,* 1981; 89(2):69-78). More than 300 proteins may be identified in the dOMV. 75% of the total protein content of the dOMV are represented by 10 most abundant proteins, including the outer membrane proteins porin A (PorA) and porin B (PorB) which represent up to 50% of the total proteins.

The *Neisseria meningitidis* porin protein (Por) is an antigenic determinant for serovar typing. Two classes of Porins, PorA and PorB, and antigenically distinct variants within each class resulting from sequence variations in the por gene variable regions (VRs) encoding surface-exposed loops are identified.

dOMV suitable for the immunogenic compositions disclosed herein may be obtained from various MenB strains. dOMV may be isolated from a detergent-extract of a MenB strain. A suitable MenB strain may be a wild-type MenB strain or a MenB strain engineered to overexpress a Porin protein, such as a PorA or a PorB protein, and for example a PorA protein.

In one embodiment, dOMV may be obtained from a MenB strain expressing PorA proteins.

In one embodiment, dOMV may be obtained from MenB strains expressing a PorA VR2 subtype. A PorA VR2 subtype may be a PorA VR2 type P1.2, P1.4, P1.7, P1.10, or P1.13 protein.

In one embodiment, dOMV may be obtained from MenB strains expressing a PorA VR2 type P1.2 protein.

In one embodiment, a dOMV may be obtained from MenB strain expressing a PorA VR2 subtype and PorB P2.2a. A dOMV may be obtained from MenB strain expressing a PorA VR2 P1.2 and PorB P2.2a.

In one embodiment, a dOMV may comprise a PorA VR2 subtype and PorB P2.2a. A dOMV may comprise a PorA VR2 P1.2 and PorB P2.2a.

In another embodiment, a dOMV may comprise PorA VR2 P1.2 and PorB P2.2a and immunotype LOS L3,7. PorA and PorB may represent about 50% of the proteins of the dOMV.

In some embodiments, dOMV may be obtained from a single MenB strain, or from different MenB strains. In the latter case, the MenB strains may express the same sub-type of PorA protein, or different PorA protein sub-type, or different type of pore protein, such as PorA and PorB proteins.

Useable MenB strains from which dOMV presenting the sought Porin protein may be identified for instance from the PubMLST database (https://pubmlst.org/). For example, a suitable MenB strain may be obtained by selecting within such database MenB strains from epidemic outbreaks, and then selecting within such subset the MenB strains having a gene coding for the porin protein of interest, such as PorA VR2 P1.2 protein. Then, it may be evaluated with known techniques in the art whether the selected strain(s) effectively expresses the porin protein of interest.

As examples of MenB strains suitable to obtain dOMV according to the disclosure, one may mention the following ones: NG H36, BZ 232, DK 353, B6116/77, BZ 163, 0085/00, NG P20, 0046/02, M11 40123, M12 240069, N5/99, 99M, or M07 240677.

In one exemplary embodiment, a MenB strain may be the MenB strain 99M expressing the PorA VR2 P1.2 protein subtype.

In one embodiment, a dOMV may comprise porin A (PorA) VR2 subtype P1.2.

In another embodiment, a dOMV may comprise outer membrane protein porin A (PorA) and/or outer membrane protein porin B (PorB). PorA may be present in an amount ranging from about 3% to about 15%, or in an amount of about 5% to about 9 or 10% relative to the total proteins present in said dOMV. PorB may be present in an amount ranging from about 30% to about 70%, or from about 35% to about 65%, or from about 38% to about 58% relative to the total proteins present in the dOMV.

In one embodiment, a dOMV may be obtained with a detergent-extraction method using at least a step of deoxycholate treatment.

A suitable method to obtain dOMV may be as disclosed in Helting et al. (*Acta Pathol Microbiol Scand C.* 1981 April; 89(2):69-78) or in Example 2 of U.S. Pat. No. 4,695,624. For example, bacteria culture may be centrifuged to obtain a pellet which may be then extracted with a detergent, for example a deoxycholate or sodium dodecyl sulfate (SDS) under heating, for example from about 50° C. to about 60° C., or at about 56° C., and for a time ranging from about 10 to about 20 minutes, or at about 15 minutes. Resulting materials may then be centrifugated, and the pellets may be further suspended and purified according to any methods known in the art.

In one embodiment, a dOMV may be present in an amount ranging from about 5 µg/dose to about 400 µg/dose, or from about 10 µg/dose to about 300 µg/dose, or from about 25 µg/dose to about 250 µg/dose, or from about 35 µg/dose to about 225 µg/dose, or from about 50 µg/dose to about 200 µg/dose, or from about 75 µg/dose to about 180 µg/dose, or from about 100 µg/dose to about 150 µg/dose, or from about 110 µg/dose to about 125 µg/dose. In one embodiment, a dOMV may be present in an amount at about 25 µg/dose, or at about 50 µg/dose, or at about 125 µg/dose.

Further Antigens

In one embodiment, an immunogenic composition as disclosed herein may comprise at least one further antigen than the combination of *Neisseria meningitidis* antigens as disclosed herein.

In an exemplary embodiment, a further antigen may be a saccharide antigen from *N. meningitidis* serogroup A, C, W135, Y and/or X conjugated to a carrier protein. In one embodiment, the further antigens may be a combination of conjugates of MenA, MenC, MenW-135 and MenY capsular polysaccharides to a carrier protein.

In an exemplary embodiment, a further antigen may be a saccharide antigen from *N. meningitidis* serogroup A, C, W135, and/or Y conjugated to a carrier protein. In one embodiment, the further antigens may be a combination of conjugates of MenA, MenC, MenW-135 and MenY capsular polysaccharides to a carrier protein.

The carrier protein for the different capsular polysaccharide may be different or identical. Carrier proteins may include inactivated bacterial toxins such as diphtheria toxoid, CRM197, tetanus toxoid, pertussis toxoid, *E. coli* LT, *E. coli* ST, and exotoxin A from *Pseudomonas aeruginosa*. Bacterial outer membrane proteins such as, porins, transferrin binding proteins, pneumolysin, pneumococcal surface protein A (PspA), or pneumococcal adhesin protein (PsaA), could also be used. Other proteins, such as ovalbumin, keyhole limpit hemocyanin (KLH), bovine serum albumin (BSA) or purified protein derivative of tuberculin (PPD) may also be used as carrier proteins. It may be a CRM197 protein, a tetanus or a diphtheria toxoid. In one embodiment, it is a tetanus toxoid.

The conjugates may be a population comprising molecules with a molecular weight in the range of 700 kDa to 1400 kDa or 800 kDa to 1300 kDa.

Within each dose, the amount of an individual saccharide antigen may be between 1-50 µg measured as mass of saccharide. For example, a total of 40 µg of saccharides per dose may be administered. For example, 10 µg of each polysaccharide and approximately 55 µg of carrier protein, such as tetanus toxoid protein, may be administered.

In one embodiment, the further antigens may be a combination of MenA, MenC, MenW-135 and MenY capsular polysaccharides each conjugated to a tetanus toxoid carrier protein, wherein the MenA polysaccharide is conjugated to the tetanus toxoid carrier via an adipic acid dihydrazide (ADH) linker while the MenC, MenW-135 and MenY polysaccharides are each directly conjugated to the tetanus toxoid carrier (TT).

In one embodiment, the further antigens may be a combination of conjugates of MenA, MenC, MenW-135 and MenY capsular polysaccharides to tetanus toxoid carrier protein. In an exemplary embodiment, the conjugated saccharide antigens from *N. meningitidis* serogroup A, C, W135 and/or Y may be as disclosed in WO 2018/045286 A1 or WO 2002/058737 A2.

In one embodiment, the further antigens are the ones of the commercially available MenACYW-TT conjugate vaccine MENQUADFI®.

Adjuvant

In one embodiment, a composition as disclosed herein may further comprise an adjuvant.

In one embodiment, an adjuvant may be an aluminum-based adjuvant (or aluminum salt). An aluminum-based adjuvant may be aluminum hydroxide adjuvant (e.g., aluminum oxyhydroxide—AlOOH), aluminum phosphate adjuvant (e.g., aluminum hydroxyphosphate—Al(OH)PO$_4$—or orthophosphate—AlPO$_4$), sulphate aluminum salt adjuvant, aluminium hydroxyphosphate sulfate adjuvant, potassium aluminium sulfate adjuvant, aluminum hydroxycarbonate, a combination of aluminum hydroxide and magnesium hydroxide (commercially available as Imject® Alum), or a mixture thereof. In one embodiment, an aluminum-based adjuvant may be an aluminum hydroxide adjuvant (e.g., aluminum oxyhydroxide—AlOOH), an aluminum phosphate adjuvant (e.g., aluminum hydroxyphosphate—Al(OH)PO$_4$—or orthophosphate—AlPO$_4$), or a mixture thereof. In one embodiment, an aluminum-based adjuvant may be an aluminum phosphate adjuvant, such as an aluminum hydroxyphosphate (Al(OH)PO$_4$) or an aluminum orthophosphate—(AlPO$_4$). The adjuvant may take any suitable form, such as gel, crystalline, amorphous, etc. In one embodiment, an aluminum-based adjuvant may be an amorphous hydroxyphosphate aluminum salt. In one embodiment, an aluminum-based adjuvant may be an orthophosphate aluminum salt. In another embodiment an aluminum-based adjuvant may be a crystalline oxyhydroxide aluminum salt (boehmite).

A hydroxyphosphate or orthophosphate aluminum adjuvant may be obtained by precipitation of aluminum oxyhydroxide in presence of phosphate. The reaction conditions and reactant concentrations during the precipitation reaction influence the degree of substitution of phosphate for hydroxyl in the salt.

Hydroxyphosphate or orthophosphate aluminum adjuvant may have a PO/Al molar ratio between 0.3 and 0.99, and for example a ratio between 0.8 and 0.95 (e.g., 0.88+0.05).

Hydroxyphosphate aluminum [Al(OH)x(PO4)y] adjuvant, wherein the sum of the valence of each anion times its mole fraction is −3] can be distinguished from AlPO$_4$ by the presence of hydroxyl groups. For example, an IR spectrum band at 3146 cm$^{-1}$ (e.g., when heated to 200° C.) indicates the presence of structural hydroxyls.

Aluminum oxyhydroxide [AlO(OH)] can be distinguished from Al(OH)3 by IR spectroscopy, in particular by the presence of an adsorption band at 1070 cm$^{-1}$ and a strong shoulder at 3090-3100 cm$^{-1}$.

Mixtures of different aluminum-based adjuvants may also be used.

In one embodiment, an adjuvant may be an aluminum phosphate adjuvant.

In exemplary embodiments, an immunogenic composition as disclosed herein may comprise single aluminum-based adjuvant, i.e., which may represent more than 90%, more than 99%, or even more than 99.9% of the aluminum adjuvant present in the composition. The aluminum-based adjuvant may be present such that the concentration of Al$^{3+}$ may be from about 0.5 mg/mL to about 1.5 mg/mL of Al$^{3+}$, or from about 0.8 to about 1.2 mg/mL of Al$^{3+}$ or may be of about 1.00 mg/ml of Al$^{3+}$.

An aluminum-based adjuvant, such as aluminum phosphate adjuvant, may be present in a composition disclosed herein in an amount ranging from about 100 µg/dose to about 1000 µg/dose, or from about 150 µg/dose to about 900 µg/dose, or from about 200 µg/dose to about 800 µg/dose, or from about 250 µg/dose to about 700 µg/dose, or from about 300 µg/dose to about 600 µg/dose, or from about 350 µg/dose to about 550 µg/dose, or from about 400 µg/dose to about 500 µg/dose, or from about 400 µg/dose to about 800 µg/dose, or at about 400 µg/dose, or at about 800 µg/dose.

A composition may include other adjuvants in addition to (or in place of) the aluminum-based adjuvants.

Suitable adjuvants may include, but are not limited to: calcium phosphate adjuvant, MF59 (4.3% w/v squalene, 0.5% w/v Tween 80™, 0.5% w/v Span 85), a CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's adjuvant (incomplete Freund's adjuvant; complete Freund's adjuvant), N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(I'-2'-dip-almitoyl-sn-glycero-3-hydroxyphosphoryloxy)-ethylamine (CGP 19835A, referred to as MTP-PE), and RIBI, which comprises three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen or antigenic epitope thereof.

Further exemplary adjuvants to enhance effectiveness of a composition may include, but are not limited to: (1) oil-in-water emulsion formulations (with or without other specific immunostimulating agents such as muramyl peptides (see below) or bacterial cell wall components), such as for example (a) MF59 (WO 90/14837), comprising 5% Squalene, 0.5% Tween 80, and 0.5% Span 85 (optionally comprising MTP-PE) formulated into submicron particles using a microfluidizer, (b) SAF, comprising 10% Squalane, 0.4% Tween 80, 5% pluronic-blocked polymer L121, and thr-MDP either microfluidized into a submicron emulsion or vortexed to generate a larger particle size emulsion, and (c) RIBI adjuvant system (RAS), (Ribi Immunochem, Hamilton, Mont.) comprising 2% Squalene, 0.2% Tween 80, and one or more bacterial cell wall components such as monophosphorylipid A (MPL), trehalose dimycolate (TDM), and cell wall skeleton (CWS), e.g., MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g., WO 00/07621; (3) Complete Freund's Adjuvant (CFA) or Incomplete Freund's Adjuvant (IF A); (4) cytokines, such as interleukins (e.g., IL-1, IL-2, IL-4, IL-5, IL-6, IL-7, IL-12 (WO99/44636), etc.), interferons (e.g., gamma interferon), macrophage colony stimulating factor (M-CSF), tumor necrosis factor (TNF), etc.; (5) monophosphoryl lipid A (MPL) or 3-O-deacylated MPL (3dMPL) e.g., GB-2220221, EP-A-0689454, optionally in the substantial absence of alum when used with pneumococcal saccharides e.g., WO 00/56358; (6) combinations of 3dMPL with, for example, QS21 and/or oil-in-water emulsions e.g., EP-A-0835318, EP-A-0735898, EP-A-0761231; (7) oligonucleotides comprising CpG motifs (see, e.g., WO 98/52581), e.g., an oligonucleotide comprising at least one CG dinucleotide, where the cytosine is unmethylated; (8) a polyoxyethylene ether or a polyoxyethylene ester (see, e.g., WO 99/52549); (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g., a CpG oligonucleotide) (WO 00/62800); (11) an immunostimulant and a particle of metal salt e.g., WO 00/23105; (12) a saponin and an oil-in-water emulsion e.g., WO 99/11241; (13) a saponin (e.g., QS21)+3dMPL+1M2 (optionally+a sterol) e.g., WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

Adjuvants suitable for administration to a human may be an aluminum salt adjuvant (e.g., aluminum phosphate or aluminum hydroxide).

Immunogenic Compositions

An immunogenic composition discloses here may comprise a combination of meningococcal antigens, said combination comprising at least one factor H binding protein (fHBP) A protein, at least one fHBP B protein, at least one *Neisseria* adhesin A (NadA) protein, and at least one detergent-extracted Outer Membrane Vesicle (dOMV).

An immunogenic composition discloses here may comprise a combination of *Neisseria meningitidis* serogroup B antigens, said combination comprising at least one factor H binding protein (fHBP) A protein, at least one fHBP B protein, at least one *Neisseria* adhesin A (NadA) protein, and at least one detergent-extracted Outer Membrane Vesicle (dOMV). The fHBP A protein and/or the fHBP B protein may be non-lipidated.

The fHBP A protein may be a mutated protein comprising at least about 85% identity with SEQ ID NO: 1 and/or the fHBP B protein may be a mutated protein comprising at least about 85% identity with SEQ ID NO: 3.

The fHBP A protein may comprise at least one amino acid substitution selected from at least one of: a) an amino acid substitution of the asparagine at amino acid 115 (N115); b) an amino acid substitution of the aspartic acid at amino acid 121 (D121); c) an amino acid substitution of the serine at amino acid 128 (S128); d) an amino acid substitution of the leucine at amino acid 130 (L130); e) an amino acid substitution of the valine at position 131 (V131); f) an amino acid substitution of the glycine at position 133 (G133); g) an amino acid substitution of the lysine at position 219 (K219); and h) an amino acid substitution of the glycine at position 220 (G220), based on the numbering of SEQ ID NO:6, or comprises or consists of SEQ ID NO: 2, and/or the fHBP B protein may comprise at least one amino acid substitution selected from at least one of: a) an amino acid substitution of the glutamine at amino acid 38 (Q38); b) an amino acid substitution of the glutamic acid at amino acid 92 (E92); c) an amino acid substitution of the arginine at amino acid 130 (R130); d) an amino acid substitution of the serine at amino acid 223 (S223); and e) an amino acid substitution of the histidine at amino acid 248 (H248), based on the numbering of SEQ ID NO:6, or comprises or consists of SEQ ID NO: 4.

The fHBP A protein and/or the fHBP B may be present in an amount ranging from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose, or at about 25 μg/dose, or at about 50 μg/dose, or at 1 about 00 μg/dose.

The NadA protein may be NadA1 protein or may comprise at least about 85% identity with SEQ ID NO: 5 or comprises or consists of SEQ ID NO:5.

The NadA protein may be present in an amount ranging from about 20 μg/dose to about 200 μg/dose, or from about 25 μg/dose to about 180 μg/dose, or from about 40 μg/dose to about 140 μg/dose, or from about 50 μg/dose to about 120 μg/dose, or from about 75 μg/dose to about 100 μg/dose, or at about 50 μg/dose.

The dOMV may comprise porin A (PorA).

The dOMV may be present in an amount ranging from about 5 μg/dose to about 400 μg/dose, or from about 10 μg/dose to about 300 μg/dose, or from about 25 μg/dose to about 250 μg/dose, or from about 35 μg/dose to about 225 μg/dose, or from about 50 μg/dose to about 200 μg/dose, or from about 75 μg/dose to about 180 μg/dose, or from about 100 μg/dose to about 150 μg/dose, or from about 110 μg/dose to about 125 μg/dose, or at about 25 μg/dose, or at about 50 μg/dose, or at about 125 μg/dose.

The composition may comprise an adjuvant, for example an aluminum-based adjuvant, for example an aluminum-based adjuvant selected in a group comprising aluminum hydroxide adjuvant, aluminum phosphate adjuvant, sulphate aluminum salt adjuvant, aluminium hydroxyphosphate sulfate adjuvant, potassium aluminium sulfate adjuvant, aluminum hydroxycarbonate, a combination of aluminum hydroxide and magnesium hydroxide, and mixtures thereof, for example being an aluminum phosphate adjuvant.

The composition may be comprise or consist of about 25 to about 100 μg/dose of a non-lipidated fHBP A protein comprising or consisting of SEQ ID NO: 2, about 25 to about 100 μg/dose of a non-lipidated fHBP B protein comprising or consisting of SEQ ID NO: 4, about 25 to about 100 μg/dose of a NadA protein comprising or consisting of SEQ ID NO: 5, about 20 to about 150 μg/dose of dOMV from a MenB strain expressing PorA VR2 P1.2, about 100 to about 600 μg/dose of aluminum phosphate adjuvant, 50 mM acetate buffer and pH 6.0.

The composition may further comprise at least a conjugated capsular saccharide from one or more of *Neisseria meningitidis* serogroups A, C, W135 and/or Y.

It is also disclosed a vaccine comprising a composition as described herein.

A composition or a vaccine as disclosed herein may be for use in protecting against a meningococcal infection or may be for use in inducing an immune response against a meningococcus bacterium.

It is further disclosed a composition comprising or consisting of a mRNA coding for a fHBP A protein comprising at least about 85%, at least about 90%, at least 95%, at least about 98%, at least about 99%, at least about 99.5%, or about 100% amino acid sequence identity to SEQ ID NO: 2, a mRNA coding for a fHBP B protein comprising at least about 85%, at least about 90%, at least about 95%, at least about 98%, at least about 99%, at least about 99.5%, or about 100% amino acid sequence identity to SEQ ID NO: 4, a mRNA coding for a NadA protein comprising at least about 85%, at least about 90%, at least about 95%, at least about 98%, at least about 99%, at least about 99.5%, or about 100% amino acid sequence identity to SEQ ID NO: 5 and dOMV from a MenB expressing a PorA VR2 P1.2.

Formulations

In another aspect, the present disclosure relates to a vaccine comprising a composition as disclosed herein.

An immunogenic or vaccine composition as disclosed herein may be formulated into preparations in solid, semi-solid, liquid forms, such as tablets, capsules, powders, aerosols, solutions, suspensions, or emulsions. Typical routes of administering such compositions include, without limitation, oral, topical, transdermal, inhalation, parenteral, sublingual, buccal, intranasal. The term parenteral as used herein includes subcutaneous injections, intravenous, intramuscular, intradermal, intrasternal injection or infusion techniques. In some embodiments, a vaccine composition as disclosed herein may be administered by transdermal, subcutaneous, intradermal or intramuscular route. Compositions of the present disclosure are formulated based upon the mode of delivery, including, for example, compositions formulated for delivery via parenteral delivery, such as intramuscular, intradermal, or subcutaneous injection.

An immunogenic composition as disclosed herein may be administered via any suitable route, such as by mucosal administration (e.g., intranasal or sublingual), parenteral administration (e.g., intramuscular, subcutaneous, transcutaneous, or intradermal route), or oral administration. As appreciated by the man skilled in the art, an immunogenic composition may be suitably formulated to be compatible with the intended route of administration. In one embodiment, an immunogenic composition as disclosed herein may be formulated to be administered via the intramuscular route, or the intradermal route, or the subcutaneous route. In one embodiment, an immunogenic composition may be formulated to be administered via the intramuscular route.

Compositions as disclosed herein are formulated so as to allow the active ingredients comprised therein to be bioavailable upon administration of the composition to a subject.

Actual methods of preparing such dosage forms are known, or will be apparent, to those skilled in this art; for example, see Remington: The Science and Practice of Pharmacy, 20th Edition (Philadelphia College of Pharmacy and Science, 2000).

Immunogenic compositions as disclosed herein may be formulated with any pharmaceutically acceptable excipient. The compositions may comprise at least one inert diluent or carrier. One exemplary pharmaceutically acceptable vehicle is a physiological saline buffer. Other physiologically acceptable vehicles are known to those skilled in the art and are described, for instance, in Remington's Pharmaceutical Sciences (18th edition), ed. A. Gennaro, 1990, Mack Publishing Company, Easton, Pa. An immunogenic composition as described herein may optionally comprise pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, human serum albumin, essential amino acids, nonessential amino acids, L-arginine hydrochlorate, saccharose, D-trehalose dehydrate, sorbitol, tris (hydroxymethyl) aminomethane and/or urea. In addition, the vaccine composition may optionally comprise pharmaceutically acceptable additives including, for example, diluents, binders, stabilizers, and preservatives.

In one embodiment, the composition may be in the form of a liquid, for example, a solution, an emulsion or a suspension. The liquid may be for delivery by injection. Compositions intended to be administered by injection may comprise at least one of: a surfactant, preservative, wetting agent, dispersing agent, suspending agent, buffer, stabilizer and isotonic agent may be included. The liquid compositions as disclosed herein may include at least one of: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose; agents to act as cryoprotectants such as sucrose or trehalose.

In another embodiment, a composition as disclosed herein may have a pH in a range of about 4.0 to about 9.0.

The pH of an immunogenic composition disclosed herein may range from about 4.5 to about 8.5, or from about 4.8 to about 8.2, or from about 5.0 to about 8.0, or from about 5.2 to about 7.5, or from about 5.4 to about 7.0, or from about 5.5 to about 6.8, or from about 5.7 to about 6.5, or from about 5.8 to about 6.2. In one embodiment, a pH of a composition as disclosed herein may be about 6.0. Stable pH may be maintained by the use of a buffer.

In one embodiment, a composition as disclosed herein may further comprise a buffer. As possible usable buffers, one may cite a Tris buffer, an acetate buffer, a citrate buffer, a phosphate buffer, an HEPES buffer, or a histidine buffer.

In an exemplary embodiment, a composition as disclosed herein may comprise a sodium acetate buffer. A sodium acetate buffer may be present at a at a concentration ranging from about 10 mM to about 300 mM, or ranging from about 10 mM to about 250 mM, or ranging from about 20 mM to about 250 mM, or ranging from about 20 mM to about 150 mM, or from about 20 mM to about 130 mM, or from about 30 mM to about 120 mM, or from about 40 mM to about 100 mM, or from about 50 mM to about 80 mM, or from about 50 mM to about 60 mM, or for example at a concentration of about 50 mM.

Immunogenic compositions may be isotonic with respect to mammals, such as humans.

An immunogenic composition may also comprise one or several additional salts, such as a sodium salt, a calcium salt, or a magnesium salt. In one embodiment, a sodium salt may be selected in the group comprising sodium chloride, sodium phosphate. In one embodiment, a sodium salt may be sodium chloride. A calcium salt may be a calcium chloride salt. A magnesium salt may be a magnesium chloride salt. In one embodiment, a sodium salt may be present in a concentration ranging from about 10 mM to about 300 mM, or from about 30 mM to about 280 mM, or from about 50 mM to about 250 mM, or from about 60 mM to about 220 mM, or from about 80 mM to about 200 mM, or from about 100 mM to about 180 mM, or from about 120 mM to about 160 mM, or may be for example at a concentration of about 150 mM. A calcium or a magnesium may be present in an amount ranging from about 1 mM to about 15 mM, or from about 5 mM to about 10 mM.

The parenteral preparation can be enclosed in ampoules, disposable syringes or multiple dose vials made of glass or plastic. An injectable composition is for example sterile.

Immunogenic compositions as disclosed herein may be sterilized by conventional sterilization techniques, for example with UV or gamma-radiation, or may be sterile filtered. The compositions resulting from sterile filtration of liquid immunogenic compositions as disclosed herein may be packaged and stored in liquid form or lyophilized. A lyophilized composition may be reconstituted with a sterile aqueous carrier prior to administration. Dry compositions may include stabilizers such as mannitol, sucrose, or dodecyl maltoside, as well as mixtures thereof e.g., lactose/sucrose mixtures, sucrose/mannitol mixtures, etc.

The compositions as disclosed herein are administered in a therapeutically effective amount, which will vary depending on a variety of factors including the activity of the specific therapeutic agent employed; the metabolic stability and length of action of the therapeutic agent; the age, body weight, general health, sex, and diet of the patient; the mode and time of administration; the rate of excretion; the drug combination; the severity of the specific disorder or condition; and the subject undergoing therapy.

In one embodiment, a composition as disclosed herein may comprise or consist of a non-lipidated fHBP A protein comprising or consisting of SEQ ID NO: 2, a non-lipidated fHBP B protein comprising or consisting of SEQ ID NO: 4, a NadA protein comprising or consisting of SEQ ID NO: 5, dOMV from a MenB expressing PorA VR2 P1.2. The composition may comprise an aluminum phosphate adjuvant. The composition may comprise a 50 mM acetate buffer and pH 6.0

In one embodiment, a composition as disclosed herein may comprise or consist of a non-lipidated fHBP A protein consisting of SEQ ID NO: 2, a non-lipidated fHBP B protein consisting of SEQ ID NO: 4, a NadA protein consisting of SEQ ID NO: 5, dOMV from a MenB expressing PorA VR2 P1.2, an aluminum phosphate adjuvant, 50 mM acetate buffer and pH 6.0.

In another embodiment, a composition as disclosed herein may comprise or consist of about 25 to about 100 μg/dose of a non-lipidated fHBP A protein consisting of SEQ ID NO: 2, about 25 to about 100 μg/dose of a non-lipidated fHBP B protein consisting of SEQ ID NO: 4, about 25 to about 100 μg/dose of a NadA protein consisting of SEQ ID NO: 5, about 20 to about 150 μg/dose of dOMV from a MenB strain expressing PorA VR2 P1.2, about 100 to about 800 μg/dose of aluminum phosphate adjuvant, 50 mM acetate buffer and pH 6.0.

In another embodiment, a composition as disclosed herein may comprise or consist of about 25 μg/dose of a non-lipidated fHBP A protein consisting of SEQ ID NO: 2, about 25 μg/dose of a non-lipidated fHBP B protein consisting of SEQ ID NO: 4, about 25 μg/dose of a NadA protein consisting of SEQ ID NO: 5, about 25 μg/dose of dOMV from a MenB strain expressing PorA VR2 P1.2, about 100 μg/dose of aluminum phosphate adjuvant, 50 mM acetate buffer and pH 6.0.

In another embodiment, a composition as disclosed herein may comprise or consist of about 25 μg/dose of a non-lipidated fHBP A protein consisting of SEQ ID NO: 2, about 25 μg/dose of a non-lipidated fHBP B protein consisting of SEQ ID NO: 4, about 50 μg/dose of a NadA protein consisting of SEQ ID NO: 5, about 50 μg/dose of dOMV from a MenB strain expressing PorA VR2 P1.2, about 400 μg/dose of aluminum phosphate adjuvant, 50 mM acetate buffer and pH 6.0.

In another embodiment, a composition as disclosed herein may comprise or consist of about 50 μg/dose of a non-lipidated fHBP A protein consisting of SEQ ID NO: 2, about 50 μg/dose of a non-lipidated fHBP B protein consisting of SEQ ID NO: 4, about 50 μg/dose of a NadA protein consisting of SEQ ID NO: 5, about 25 μg/dose of dOMV from a MenB strain expressing PorA VR2 P1.2, about 400 μg/dose of aluminum phosphate adjuvant, 50 mM acetate buffer and pH 6.0.

In another embodiment, a composition as disclosed herein may comprise or consist of about 50 μg/dose of a non-lipidated fHBP A protein consisting of SEQ ID NO: 2, about 50 μg/dose of a non-lipidated fHBP B protein consisting of SEQ ID NO: 4, about 50 μg/dose of a NadA protein consisting of SEQ ID NO: 5, about 50 μg/dose of dOMV from a MenB strain expressing PorA VR2 P1.2, about 400 μg/dose of aluminum phosphate adjuvant, 50 mM acetate buffer and pH 6.0.

In another embodiment, a composition as disclosed herein may comprise or consist of about 50 μg/dose of a non-lipidated fHBP A protein consisting of SEQ ID NO: 2, about 50 μg/dose of a non-lipidated fHBP B protein consisting of SEQ ID NO: 4, about 50 μg/dose of a NadA protein consisting of SEQ ID NO: 5, about 125 μg/dose of dOMV from a MenB strain expressing PorA VR2 P1.2, about 400 μg/dose of aluminum phosphate adjuvant, 50 mM acetate buffer and pH 6.0.

In another embodiment, a composition as disclosed herein may comprise or consist of about 50 μg/dose of a non-lipidated fHBP A protein consisting of SEQ ID NO: 2, about 50 μg/dose of a non-lipidated fHBP B protein consisting of SEQ ID NO: 4, about 50 μg/dose of a NadA protein consisting of SEQ ID NO: 5, about 50 μg/dose of dOMV from a MenB strain expressing PorA VR2 P1.2, about 200 μg/dose of aluminum phosphate adjuvant, 50 mM acetate buffer and pH 6.0.

In another embodiment, a composition as disclosed herein may comprise or consist of about 75 μg/dose of a non-lipidated fHBP A protein consisting of SEQ ID NO: 2, about 75 μg/dose of a non-lipidated fHBP B protein consisting of SEQ ID NO: 4, about 75 μg/dose of a NadA protein consisting of SEQ ID NO: 5, about 75 μg/dose of dOMV from a MenB strain expressing PorA VR2 P1.2, about 300 μg/dose of aluminum phosphate adjuvant, 50 mM acetate buffer and pH 6.0.

In another embodiment, a composition as disclosed herein may comprise or consist of about 100 μg/dose of a non-lipidated fHBP A protein consisting of SEQ ID NO: 2, about 100 μg/dose of a non-lipidated fHBP B protein consisting of SEQ ID NO: 4, about 100 μg/dose of a NadA protein consisting of SEQ ID NO: 5, about 125 μg/dose of dOMV from a MenB strain expressing PorA VR2 P1.2, about 400 μg/dose of aluminum phosphate adjuvant, 50 mM acetate buffer and pH 6.0.

In another embodiment, a composition as disclosed herein may comprise or consist of about 100 μg/dose of a non-lipidated fHBP A protein consisting of SEQ ID NO: 2, about 100 μg/dose of a non-lipidated fHBP B protein consisting of SEQ ID NO: 4, about 50 μg/dose of a NadA protein consisting of SEQ ID NO: 5, about 50 μg/dose of dOMV from a MenB strain expressing PorA VR2 P1.2, about 400 μg/dose of aluminum phosphate adjuvant, 50 mM acetate buffer and pH 6.0.

In another embodiment, a composition as disclosed herein may comprise or consist of about 100 μg/dose of a non-lipidated fHBP A protein consisting of SEQ ID NO: 2, about 100 μg/dose of a non-lipidated fHBP B protein consisting of SEQ ID NO: 4, about 50 µg/dose of a NadA protein consisting of SEQ ID NO: 5, about 50 µg/dose of dOMV from a MenB strain expressing PorA VR2 P1.2, about 800 µg/dose of aluminum phosphate adjuvant, 50 mM acetate buffer and pH 6.0.

In one embodiment, the present disclosure relates to a container comprising a composition as disclosed herein. A container may comprise an immunogenic composition comprising a combination of meningococcal antigens, said combination comprising at least one factor H binding protein (fHBP) A protein, at least one fHBP B protein, at least one *Neisseria* adhesin A (NadA) protein, and at least one detergent-extracted Outer Membrane Vesicle (dOMV).

Further, a container may comprise a composition comprising or consisting of from about 25 to 100 µg/dose of a non-lipidated fHBP A protein consisting of SEQ ID NO: 2, from about 25 to 100 µg/dose of a non-lipidated fHBP B protein consisting of SEQ ID NO: 4, from about 25 to 100 µg/dose of a NadA protein consisting of SEQ ID NO: 5, from about 20 to 150 µg/dose of dOMV from a MenB strain expressing PorA VR2 P1.2, from about 100 to 800 µg/dose of aluminum phosphate adjuvant, 50 mM acetate buffer and pH 6.0.

A container may be a vial. A vial may be a multi-dose vials or may be a single-dose vial. Suitable vials may be a small glass or plastic container sealed with the most suitable stopper and seal.

Alternatively, a container may be a pre-filled syringe. A prefilled syringe may include a syringe barrel storing a liquid composition as disclosed herein. A gasket and a plunger are inserted in the syringe barrel. The gasket seals the syringe barrel in a liquid-tight manner to prevent leakage of the liquid drug, and the plunger slides the gasket. Various types of prefilled syringes are known in the art, as for example described in U.S. Pat. No. 10,625,025 or in WO 2013/046855.

In case where a composition as disclosed herein is to be mixed and injected with another vaccine composition, as for example a tetravalent MenACWY-conjugated composition, both compositions may be packaged in a container being a single vial or a pre-filled syringe or in a dual-chamber syringe. A dual-chamber syringe also known as a sequential or bypass syringe, may comprise a single barrel separated by a septum into two compartments, proximal and distal. Depression of the syringe's plunger forces admixing of the two vaccine compositions in the distal compartment. Various types of dual-chamber syringes are known in the art, as for example described in U.S. Pat. No. 10,695,505. A dual-chamber syringe may be also used in case a vaccine composition is formulated in a dried-form, such as a lyophilized form, and is stored with the liquid vehicle for reconstitution. In such case, the dried vaccine is stored in one chamber and the liquid for reconstitution and injection is stored in a second chamber.

Manufacturing Methods

The compositions as disclosed herein may be prepared by methodology well known in the pharmaceutical art.

In one embodiment, the present disclosure relates to a method for preparing an immunogenic composition as disclosed herein or a vaccine as disclosed herein, the method comprising at least a step of admixing meningococcal antigens and, optionally, an aluminum salt, said antigens comprising at least one factor H binding protein (fHBP) A protein, at least one fHBP B protein, at least one *Neisseria* adhesin A (NadA) protein, and at least one detergent-extracted Outer Membrane Vesicle (dOMV).

In one embodiment, a step of admixing may comprise a blending of a first mixture of at least one factor H binding protein (fHBP) A protein, optionally adsorbed onto $AlPO_4$ and of at least one fHBP B protein, optionally adsorbed onto $AlPO_4$ salt with a second mixture of at least one NadA protein, optionally adsorbed onto $AlPO_4$ and of at least one dOMV.

In one embodiment, a step of admixing may comprise a blending of a first mixture of at least one factor H binding protein (fHBP) A protein adsorbed onto $AlPO_4$ and of at least one fHBP B protein adsorbed onto $AlPO_4$ salt with a second mixture of at least one NadA protein adsorbed onto $AlPO_4$ and of at least one dOMV.

The antigens fHBP A and B and NadA may be first adsorbed on an aluminum-based adjuvant, e.g., $AlPO_4$, and then mixed together and with dOMV. The mixing may be made in any order. Alternatively, the fHBP A and B adsorbed on the aluminum-based adjuvant may be mixed together in an appropriate buffer. NadA adsorbed on aluminum-based adjuvant and dOMV may be mixed together in a appropriate buffer. Then the two mix may be blended to obtain an immunogenic composition as disclosed herein.

Further antigen, such as conjugated MenACWY polysaccharides may be then mixed with a composition as disclosed herein. Further antigenic composition, such as conjugated MenACWY polysaccharides composition may be blended together with an immunogenic composition as disclosed herein, just prior to administration to a patient, optionally via a dual chamber syringe that mixes the two compositions together prior to administration.

In another embodiment the immunogenic composition or vaccine as disclosed herein is co-administered with a conjugated MenACWY polysaccharides immunogenic composition or vaccine. The conjugated MenACWY polysaccharides immunogenic composition or vaccine that may be co-administered with the immunogenic composition or vaccine as disclosed herein may be MenA, MenC, MenW-135 and MenY capsular polysaccharides each conjugated to a tetanus toxoid carrier protein, optionally wherein the MenA polysaccharide is conjugated to the tetanus toxoid carrier via an adipic acid dihydrazide (ADH) linker while the MenC, MenW-135 and MenY polysaccharides are each directly conjugated to the tetanus toxoid carrier. The co-administered conjugated MenACWY polysaccharides immunogenic composition or vaccine may be as disclosed in WO 2018/045286 A1 or WO 2002/058737 A2. The co-administered conjugated MenACWY polysaccharides immunogenic composition or vaccine may be the commercially available MenACYW-TT conjugate vaccine MENQUADFI®.

In another embodiment, antigens and aluminum salt for use in a method for preparing as disclosed herein may be in a buffer.

A composition as disclosed herein may be manufactured in liquid or in a solid, e.g., lyophilized, form.

In one embodiment, immunogenic compositions as disclosed herein may be packaged and stored in dry form such as lyophilized compositions or as micropellets obtained via a prilling process as described in WO 2009/109550. In one embodiment the different components of a composition, e.g., the MenB antigens, and possibly the further antigens, may all be present in the same micropellets. In another embodiment, the components of an immunogenic composition as disclosed herein may each be in distinct micropellets, that is one component per micropellet, or all the components or some of them, in that case the other component or components may be each in distinct micropellets, may be combined by pairs or triplets (bivalent or trivalent formulations) in the same micropellets (fHBP A+B and NadA+dOMV, fHBP A+NadA and fHBP B+dOMV, fHBP B+NadA and fHBP A+dOMV, fHBP A+NadA+fHBP B and dOMV, or fHBP A+dOMV+fHBP B and NadA, etc). In such embodiment, the different micropellets comprising separately the different components or any combination of at least two of the different components may be mixed before administration to a subject. In one embodiment, they may be mixed before reconstitution in a liquid carrier. In another embodiment, they may be mixed at the time of reconstitution in liquid carrier by being added in one volume of liquid carrier. In another embodiment, they may be, first, each separately added to distinct volumes of liquid carrier, and second, the different volumes of liquid carrier may be then mixed together to give the final liquid composition to be administered to the subject.

In one embodiment, the four antigens and the AlPO$_4$ are in the same container.

In another embodiment, the adjuvant and the antigens may be prepared in at least two distinct compositions. The distinct compositions may then be blended together, just prior to administration to a patient, optionally via a dual chamber syringe that mixes the two compositions together prior to administration. In another embodiment, the distinct compositions may be administered separately, that is administered at the same time (in practice only a few seconds or minutes apart, e.g., less than 5 minutes), but via at least two distinct sites of administration, such as at least two distinct sites of injections. In another embodiment, the distinct compositions may be administered sequentially, that is at least two distinct points in time, such as at least 5 minutes apart, or up to hours or 1 or 2 days apart. In such embodiment, the distinct compositions may be administered at the same site of administration, such as the same injection site, or at different sites of administration, such as different injection sites. In such embodiment, at least one of the different components of a composition as disclosed herein may be provided separately as kit-of-parts.

Kit-of-Parts

In one embodiment, the present disclosure relates to a kit-of-parts comprising a plurality of containers wherein each of the container is comprising at least one or a combination of at least two meningococcal antigens, said antigens being selected from the group comprising fHBP A protein, fHBP B protein, NadA protein, and detergent-extracted Outer Membrane Vesicle (dOMV).

In one embodiment, at least one of the antigens of the kit-of-parts may be in dried-form. In one embodiment, at least one of the antigens may be in lyophilized or dry micropellets form. In one embodiment, a kit may optionally comprise a container comprising a physiologically injectable vehicle.

In one embodiment, the different antigens of an immunogenic composition as disclosed herein may be prepared and stored in separate containers or vials. They then may be mixed at the time of the administration to an individual.

In one embodiment, each of the antigens, fHBP A, fHBP B, NadA and dOMV may be stored each in one container. In another embodiment, the antigens may be combined by pairs or triplets (bivalent or trivalent formulations). All type of combinations may be envisioned: fHBP A+B and NadA+dOMV, fHBP A+NadA and fHBP B+dOMV, fHBP B+NadA and fHBP A+dOMV, fHBP A+NadA+fHBP B and dOMV, or fHBP A+dOMV+fHBP B and NadA, etc.

In one embodiment the fHBP A and B antigens may be stored in a first container, the NadA antigen may be stored in a second container, and the dOMV antigen may be stored in a third container. In another embodiment, the fHBP A and B antigens may be stored in a first container, and the NadA antigen and dOMV antigens may be stored both in a second container.

The antigens may be stored in a liquid formulation or in a dried form. When formulated in dried form, a supplemental container may be added to contain an injectable liquid carrier to be used to resuspend and mix the different antigens. A suitable injectable liquid carrier may comprise a buffer. Further it may comprise an adjuvant such as above indicated. An adjuvant may be an aluminum-based adjuvant, such as a AlPO$_4$.

Optionally, a kit-of-parts may comprise at least one further container or a plurality of further containers, for at least one further antigen or a plurality of further antigens. In one embodiment, the further antigens may be conjugated MenACWY polysaccharides.

In one embodiment, a kit-of-parts may comprise a first container comprising an immunogenic composition as disclosed herein and a second container comprising conjugated MenACWY polysaccharides.

Uses and Methods of Treatment

In one embodiment, the present disclosure relates to a composition as disclosed herein for use as a medicament, in particular as a vaccine.

In another aspect, the present disclosure relates to a composition as disclosed herein for use in protecting against a meningococcal infection, and in one exemplary embodiment against *N. meningitidis* serogroup B infection.

In another aspect, the present disclosure relates to a composition as disclosed herein for use in inducing an immune response against a meningococcus bacterium, and in one exemplary embodiment against *N. meningitidis* serogroup B bacterium.

In another aspect, the present disclosure relates to a composition as disclosed herein for use in inducing an immune response against a *N. meningitidis* serogroup B bacterium from the ST-41/44, the ST-32, the ST-269, the ST-213, the ST-35, the ST-461, the ST-11 and/or ST-461 Clonal Complexes In another aspect, the present disclosure relates to a composition as disclosed herein for use in inducing an immune response against a *N. meningitidis* serogroup B bacterium from the ST-11 Clonal Complex.

In another aspect, the present disclosure relates to a method for protecting an individual against a meningococcal infection, and in one exemplary embodiment against *N. meningitidis* serogroup B infection, the method comprising at least the step of administering to the individual an immunogenic composition as disclosed herein, or a vaccine as disclosed herein.

In another aspect, the present disclosure relates to a method for reducing a risk of occurrence of an invasive meningococcal disease caused by a meningococcal infection in an individual, and in one exemplary embodiment caused by *N. meningitidis* serogroup B infection, the method comprising at least the step of administering to the individual an immunogenic composition as disclosed herein, or a vaccine as disclosed herein.

In another aspect, the present disclosure relates to a method for eliciting an immune response against a meningococcus bacterium in an individual, and in one exemplary embodiment against *N. meningitidis* serogroup B bacterium, the method comprising at least the step of administering to the individual an immunogenic composition as disclosed herein, or a vaccine as disclosed herein.

In another aspect, the present disclosure relates to a method for eliciting an immune response against a *N. meningitidis* serogroup B bacterium from the ST-41/44, the ST-32, the ST-269, the ST-213, the ST-35, the ST-461, the ST-11 and/or ST-461 Clonal Complexes, the method comprising at least the step of administering to the individual an immunogenic composition as disclosed herein, or a vaccine as disclosed herein.

In another aspect, the present disclosure relates to a method for eliciting an immune response against a *N. meningitidis* serogroup B bacterium from the ST-11 Clonal Complex, the method comprising at least the step of administering to the individual an immunogenic composition as disclosed herein, or a vaccine as disclosed herein.

In one embodiment, immunogenic compositions as disclosed herein may be for use to elicit in individuals an immune response against *Neisseria meningitidis* serogroup B. Concerned individuals may be mammals, for example human beings, and for example infants, toddlers, children, teenagers, young adults, adults, and seniors. In one embodiment, an individual may be from 6 weeks-old or more, 2 months-old or more, or 10 years-old or more. As exemplary embodiments, an individual may be from 6-weeks to 55 years-old or more, for example from 2 months to 55 years-old or more, or for example from 10 to 55 years-old or more.

The methods generally involve administering to an individual in need thereof an effective amount of a subject immunogenic composition. Amounts effective for therapeutic use will depend on, e.g., the antigenic composition, the manner of administration, the weight and general state of health of the patient, and the judgment of the prescribing physician. Single or multiple doses of the antigenic compositions may be administered depending on the dosage and frequency required and tolerated by the patient, and route of administration.

Immunogenic compositions as disclosed here may be administered in a 2, 3, 2+1, or 3+1 doses regimen.

In one embodiment, an immunogenic composition disclosed herein may be administered in 2 or 3 doses. The subsequent dose may be administered about one, about two, about three, about four, about five, about six, about seven, about eight, about nine, about ten, about eleven, about twelve, about thirteen, about fourteen, about fifteen, about sixteen, about seventeen, about eighteen, about nineteen or about twenty months apart from the previous one. In one embodiment, the subsequent dose may be administered about one, about two, about five, about six, about eight, about ten, about twelve, about fourteen or about sixteen months apart from the previous one. In one embodiment, the subsequent dose may be administered about one, about two, about five, about six, or about eight, months apart from the previous one. In one embodiment, the subsequent dose may be administered about 30 days, about 60 days, or about 180 days apart from the previous one.

In a two doses regimen, the second dose may be administered about one month after the first dose, or about 2 months after the first dose, or after 6 months after the first dose. Alternatively, in a two doses regimen, the second dose may be administered about 30 days after the first dose, or about 60 days after the first dose or about 180 days after the first dose. Such two-doses regimen may be suitable for adults and/or adolescents.

In a two doses regimen, the second dose may be administered about 2 months after the first dose. Alternatively, in a two doses regimen, the second dose may be administered about 60 days after the first dose. Such two-doses regimen may be suitable for toddlers.

In a three doses regimen, the second dose may be administered about one month after the first dose and the third dose may be administered about 6 months after the first dose. Alternatively, in a three doses regimen, the second dose may be administered about 30 days after the first dose and the third dose may be administered about 180 days after the first dose. Such three-doses regimen may be suitable for adults and/or adolescents.

In a three doses regimen, the second dose may be administered about two months after the first dose and the third dose may be administered about 10 months after the first dose. Alternatively, in a three doses regimen, the second dose may be administered about 60 days after the first dose and the third dose may be administered at about 12 months of age. Such three-doses regimen may be suitable for infants.

In one embodiment, further to the 2 or 3 doses, a third or fourth dose may be administered. This subsequent dose may be administered at least one year after the last dose of the 2 or 3 doses, for example 16 months after the last dose. In such regimen the first two or three doses may be qualified as prime doses, and the subsequent one (+1) may be qualified as a boost dose.

In one embodiment, infants and toddlers, for example from 6-weeks or 2-months to 2 years-old may receive a 2+1 or a 3+1 doses regiment. In another embodiment, children, for example from 2 to 10 years-old, may receive a 2 doses regimen. In another embodiment, teenagers and adults, for example from 10 to 55 years-old may receive a 2+1 doses regimen.

Immunogenic compositions as disclosed herein may be administered by any suitable route. For example, administration by intramuscular route may be considered.

The present invention will be further described according to the following clauses and embodiments.

According to an embodiment 1, the invention relates to an immunogenic composition comprising a combination of *Neisseria meningitidis* serogroup B antigens, said combination comprising at least one factor H binding protein (fHBP) A protein, at least one fHBP B protein, at least one *Neisseria* adhesin A (NadA) protein, and at least one detergent-extracted Outer Membrane Vesicle (dOMV).

According to an embodiment 2, the invention relates to a composition according to embodiment 1, wherein the fHBP A protein and/or the fHBP B protein are non-lipidated.

According to an embodiment 3, the invention relates to a composition according to embodiment 1 or 2, wherein the fHBP A protein is a mutated protein comprising at least about 85% identity with SEQ ID NO: 1 and/or wherein the fHBP B protein is a mutated protein comprising at least about 85% identity with SEQ ID NO: 3.

According to an embodiment 4, the invention relates to a composition according to anyone of embodiments 1 to 3, wherein the fHBP A protein comprises at least one amino acid substitution selected from at least one of: a) an amino acid substitution of the asparagine at amino acid 115 (N115); b) an amino acid substitution of the aspartic acid at amino acid 121 (D121); c) an amino acid substitution of the serine at amino acid 128 (S128); d) an amino acid substitution of the leucine at amino acid 130 (L130); e) an amino acid substitution of the valine at position 131 (V131); f) an amino acid substitution of the glycine at position 133 (G133); g) an amino acid substitution of the lysine at position 219 (K219); and h) an amino acid substitution of the glycine at position 220 (G220), based on the numbering of SEQ ID NO:6, or comprises or consists of SEQ ID NO: 2, and/or wherein the fHBP B protein comprises at least one amino acid substitution selected from at least one of: a) an amino acid substitution of the glutamine at amino acid 38 (Q38); b) an amino acid substitution of the glutamic acid at amino acid 92 (E92); c) an amino acid substitution of the arginine at amino acid 130 (R130); d) an amino acid substitution of the serine at amino acid 223 (S223); and e) an amino acid substitution of the histidine at amino acid 248 (H248), based on the numbering of SEQ ID NO:6, or comprises or consists of SEQ ID NO: 4.

According to an embodiment 5, the invention relates to a composition according to anyone of embodiments 1 to 4 wherein the fHBP A protein and/or the fHBP B are present in an amount ranging from about 20 µg/dose to about 200 µg/dose, or from about 25 µg/dose to about 180 µg/dose, or from about 40 µg/dose to about 140 µg/dose, or from about 50 µg/dose to about 120 µg/dose, or from about 75 µg/dose to about 100 µg/dose, or at about 25 µg/dose, or at about 50 µg/dose, or at about 100 µg/dose.

According to an embodiment 6, the invention relates to a composition according to anyone of embodiments 1 to 5, wherein the NadA protein is NadA1 protein, or comprises at least about 85% identity with SEQ ID NO: 5 or comprises or consists of SEQ ID NO:5.

According to an embodiment 7, the invention relates to a composition according to anyone of embodiments 1 to 6, wherein the NadA protein is present in an amount ranging from about 20 µg/dose to about 200 µg/dose, or from about 25 µg/dose to about 180 µg/dose, or from about 40 µg/dose to about 140 µg/dose, or from about 50 µg/dose to about 120 µg/dose, or from about 75 µg/dose to about 100 µg/dose, or at about 50 µg/dose.

According to an embodiment 8, the invention relates to a composition according to anyone of embodiments 1 to 7, wherein the dOMV comprises porin A (PorA).

According to an embodiment 9, the invention relates to a composition according to anyone of embodiments 1 to 8, wherein the dOMV is present in an amount ranging from about 5 µg/dose to about 400 µg/dose, or from about 10 µg/dose to about 300 µg/dose, or from about 25 µg/dose to about 250 µg/dose, or from about 35 µg/dose to about 225 µg/dose, or from about 50 µg/dose to about 200 µg/dose, or from about 75 µg/dose to about 180 µg/dose, or from about 100 µg/dose to about 150 µg/dose, or from about 110 µg/dose to about 125 µg/dose, or at about 25 µg/dose, or at about 50 µg/dose, or at about 125 µg/dose.

According to an embodiment 10, the invention relates to a composition according to anyone of embodiments 1 to 9, further comprising an adjuvant, optionally an aluminum-based adjuvant that is optionally selected from the group consisting of aluminum hydroxide adjuvant, aluminum phosphate adjuvant, sulphate aluminum salt adjuvant, aluminium hydroxyphosphate sulfate adjuvant, potassium aluminium sulfate adjuvant, aluminum hydroxycarbonate, a combination of aluminum hydroxide and magnesium hydroxide, and mixtures thereof.

According to an embodiment 11, the invention relates to a composition according to anyone of embodiments 1 to 10, comprising or consisting of 25 to 100 µg/dose of a non-lipidated fHBP A protein consisting of SEQ ID NO: 2, 25 to 100 µg/dose of a non-lipidated fHBP B protein consisting of SEQ ID NO: 4, 25 to 100 µg/dose of a NadA protein consisting of SEQ ID NO: 5, 20 to 150 µg/dose of dOMV from a MenB strain expressing PorA VR2 P1.2, 100 to 600 µg/dose of aluminum phosphate adjuvant, 50 mM acetate buffer and pH 6.0.

According to an embodiment 12, the invention relates to a composition according to anyone of embodiments 1 to 11, further comprising at least a conjugated capsular saccharide from one or more of *Neisseria meningitidis* serogroups A, C, W135 and/or Y.

According to an embodiment 13, the invention relates to a vaccine comprising a composition according to anyone of embodiments 1 to 13.

According to an embodiment 14, the invention relates to a composition according to anyone of embodiments 1 to 12 or a vaccine according to embodiment 12, for use in protecting against a meningococcal infection or for use in inducing an immune response against a meningococcus bacterium.

According to an embodiment 15, the invention relates to a composition comprising or consisting of a mRNA coding for a fHBP A protein comprising at least about 85%, at least about 90%, at least about 95%, at least about 98%, at least about 99%, at least about 99.5%, or about 100% amino acid sequence identity to SEQ ID NO: 2, a mRNA coding for a fHBP B protein comprising at least about 85%, at least about 90%, at least about 95%, at least about 98%, at least about 99%, at least about 99.5%, or about 100% amino acid sequence identity to SEQ ID NO: 4, a mRNA coding for a NadA protein comprising at least about 85%, at least about 90%, at least about 95%, at least about 98%, at least about 99%, at least about 99.5%, or about 100% amino acid sequence identity to SEQ ID NO: 5 and dOMV from a MenB expressing a PorA VR2 P1.2.

According to an embodiment 16 the invention relates to an immunogenic composition comprising a combination of *Neisseria meningitidis* serogroup B antigens, said combination comprising at least one non-lipidated factor H binding protein (fHBP) A protein comprising at least about 85% identity with SEQ ID NO: 1 and comprising at least the amino acid substitution G220S based on the numbering of SEQ ID NO:6, at least one non-lipidated fHBP B protein, at least one *Neisseria* adhesin A (NadA) protein, and at least one detergent-extracted Outer Membrane Vesicle (dOMV).

According to an embodiment 17, the invention relates to a composition according to embodiment 16, wherein the non-lipidated fHBP B protein is a mutated protein comprising at least about 85% identity with SEQ ID NO: 3.

According to an embodiment 18, the invention relates to a composition according to embodiment 16 or 17, wherein the non-lipidated fHBP B protein comprises the amino acid substitution H248L based on the numbering of SEQ ID NO:6.

According to an embodiment 19, the invention relates to a composition according to anyone of embodiments 16 to 18, wherein the non-lipidated fHBP A protein comprises or consists of SEQ ID NO: 4.

According to an embodiment 20, the invention relates to a composition according to anyone of embodiments 16 to 19, wherein the non-lipidated fHBP A protein further comprises the amino acid substitutions L130R and G133D based on the numbering of SEQ ID NO:6.

According to an embodiment 21, the invention relates to a composition according to anyone of embodiments 16 to 20, wherein the non-lipidated fHBP A protein comprises or consists of SEQ ID NO: 2.

According to an embodiment 22, the invention relates to a composition according to anyone of embodiments 16 to 21, wherein the NadA protein is NadA1 protein, or comprises at least about 85% identity with SEQ ID NO: 5 or comprises or consists of SEQ ID NO:5.

According to an embodiment 23, the invention relates to a composition according to anyone of embodiments 16 to 22, wherein the dOMV comprises a PorA VR2 subtype.

According to an embodiment 24, the invention relates to a composition according to anyone of embodiments 16 to 23, wherein the dOMV comprises a PorA VR2 P1.2.

According to an embodiment 25, the invention relates to a composition according to anyone of embodiments 16 to 24, further comprising an adjuvant, optionally an aluminum-based adjuvant that is optionally selected from the group consisting of aluminum hydroxide adjuvant, aluminum phosphate adjuvant, sulphate aluminum salt adjuvant, aluminium hydroxyphosphate sulfate adjuvant, potassium aluminium sulfate adjuvant, aluminum hydroxycarbonate, a combination of aluminum hydroxide and magnesium hydroxide, and mixtures thereof.

According to an embodiment 26, the invention relates to a composition according to anyone of embodiments 16 to 25, wherein the fHBP A protein and/or the fHBP B are present in an amount ranging from about 20 µg/dose to about 200 µg/dose, or from about 25 µg/dose to about 180 µg/dose, or from about 40 µg/dose to about 140 µg/dose, or from about 50 µg/dose to about 120 µg/dose, or from about 75 µg/dose to about 100 µg/dose, or at about 25 µg/dose, or at about 50 µg/dose, or at about 100 µg/dose, the NadA protein is present in an amount ranging from about 20 µg/dose to about 200 µg/dose, or from about 25 µg/dose to about 180 µg/dose, or from about 40 µg/dose to about 140 µg/dose, or from about 50 µg/dose to about 120 µg/dose, or from about 75 µg/dose to about 100 µg/dose, or at about 50 µg/dose and the dOMV is present in an amount ranging from about 5 µg/dose to about 400 µg/dose, or from about 10 µg/dose to about 300 µg/dose, or from about 25 µg/dose to about 250 µg/dose, or from about 35 µg/dose to about 225 µg/dose, or from about 50 µg/dose to about 200 µg/dose, or from about 75 µg/dose to about 180 µg/dose, or from about 100 µg/dose to about 150 µg/dose, or from about 110 µg/dose to about 125 µg/dose, or at about 25 µg/dose, or at about 50 µg/dose, or at about 125 µg/dose.

According to an embodiment 27, the invention relates to a composition according to anyone of embodiments 16 to 26, comprising or consisting of 25 to 100 µg/dose of a non-lipidated fHBP A protein consisting of SEQ ID NO: 2, 25 to 100 µg/dose of a non-lipidated fHBP B protein consisting of SEQ ID NO: 4, 25 to 100 µg/dose of a NadA protein consisting of SEQ ID NO: 5, 20 to 150 µg/dose of dOMV from a MenB strain expressing PorA VR2 P1.2, 100 to 600 µg/dose of aluminum phosphate adjuvant, 50 mM acetate buffer and pH 6.0.

According to an embodiment 28, the invention relates to a composition according to anyone of embodiments 16 to 27, further comprising at least a conjugated capsular saccharide from one or more of *Neisseria meningitidis* serogroups A, C, W135 and/or Y.

According to an embodiment 29, the invention relates to a vaccine comprising a composition according to anyone of embodiments 16 to 28.

According to an embodiment 30, the invention relates to a method of treating a meningococcal infection or inducing an immune response against a meningococcus bacterium comprising administering to an individual in need thereof a composition comprising or consisting of a fHBP A protein comprising at least about 85%, at least about 90%, at least about 95%, at least about 98%, at least about 99%, at least about 99.5%, or about 100% amino acid sequence identity to SEQ ID NO: 2, a fHBP B protein comprising at least about 85%, at least about 90%, at least about 95%, at least about 98%, at least about 99%, at least about 99.5%, or about 100% amino acid sequence identity to SEQ ID NO: 4, a NadA protein comprising at least about 85%, at least about 90%, at least about 95%, at least about 98%, at least about 99%, at least about 99.5%, or about 100% amino acid sequence identity to SEQ ID NO: 5 and dOMV from a MenB expressing a PorA VR2 P1.2.

It is to be understood that the disclosure encompasses all variations, combinations, and permutations in which at least one limitation, element, clause descriptive term, etc., from at least one of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should be understood that, in general, where the disclosure, or aspects of the disclosure, is/are referred to as comprising particular elements, features, etc., they also encompass embodiments consisting, or consisting essentially of, such elements, features, etc. For purposes of simplicity those embodiments have not in every case been specifically set forth in so many words herein. It should also be understood that any embodiment or aspect of the disclosure can be explicitly excluded from the claims, regardless of whether the specific exclusion is recited in the specification. The publications and other reference materials referenced herein to describe the background of the disclosure and to provide additional detail regarding its practice are hereby incorporated by reference.

The sequences disclosed in the present specification serve as references. The same sequences are also presented in a sequence listing formatted according to standard requirements for the purpose of patent matters. In case of any sequence discrepancy with the standard sequence listing, the sequences described in the present specification shall be the reference.

Without limiting the present disclosure, a number of embodiments of the present disclosure are described below for the purpose of illustration.

EXAMPLES

Example 1: Antigens Preparation and Immunogenic Compositions

1. Preparation and Purification of the MenB Antigens
1. Non-Lipidated Mutated fHBP A05 (A05tmN)

For preparing the non-lipidated A05tmN, three point-mutations (G220S, L130R and G133D numbering with respect to SEQ ID NO: 6) were introduced in wild-type fHBP A05 sequence and to achieve a non-lipidated protein the first cysteine residue anchoring the lipid moiety at the N-terminal end was replaced by a Methionine (non-lipidated A05tmN: SEQ ID NO: 2). The DNA sequence for A05tmN was synthesized and then used to prepare the plasmid construct. In short, the DNA sequences of Xba1 and Xho 1 sites were added on both ends of the A05tmN sequence. To create the expression plasmids, the Xba1/Xho1 containing plasmids were digested and the resulting DNA fragments were ligated into Xba1/Xho1 digested pET28a(+) and transformed into Top10 competent cells. A positive clone was confirmed by Xba I/Xho I digestion The A05tmN plasmid was transformed into *E. coli* and the cell bank was manufactured after three rounds of colony purification.

The *E coli* strain transformed with A05tmN was amplified in semi-defined medium at 37° C. under agitation (pH 6.8—Dissolved oxygen: 20%). Expression of the antigen was induced by addition of isopropyl β-D-1-thiogalactopyranoside (IPTG).

The culture was harvested as unprocessed bulk and the bacterial biomass was separated from the media with centrifugation. The resulting cell pellets was resuspended in a buffer (20 mM Tris-HCl, pH 8.5). The resuspended pellet was processed through a homogenizer to produce cell homogenate. The homogenate was subsequently centrifuged to collect the pellet fraction. The homogenate pellet was resuspended in buffer (20 mM Tris-HCl, pH 8.5) and subjected to a pH shock treatment (pH 12 for 1 hour at room temperature with mixing). The pH was brought back down to 8.5 with 85% phosphoric acid. The supernatant fraction of the pH-shocked material was collected following centrifugation and then filtered to obtain a filtered supernatant.

The supernatant was conditioned to pH 8.5 and <5.0 mS/cm conductivity and loaded onto a capture column, GigaCap Q-650M. The elution pool is conditioned to 0.9 M ammonium sulfate (AmS), then further purified with the intermediate chromatography, Toyopearl Phenyl 600M. After the hydrophobic interaction chromatography, the eluted pool is conditioned to pH 8.5 and <8.0 mS/cm conductivity, and further purified through Nuvia aPrime 4A chromatography. This is followed by the final ultrafiltration and diafiltration using 5 kDa regenerated cellulose tangential flow filtration (TFF) membrane, and a 0.2-μm filtration.

The A05tmN was adsorbed onto $AlPO_4$ defined at 1.00 mg Al/mL of AlPO 4 in acetate buffer (50 mM sodium acetate, 150 mM NaCl, pH 6.0).

2. Non-Lipidated Mutated fHBP B01 (B01smN)

For preparing the non-lipidated B01smN, a single point-mutation was introduced in the wild-type fHBP B01 sequence and to achieve a non-lipidated protein the first cysteine residue anchoring the lipid moiety at the N-terminal end was replaced by a Methionine (non-lipidated B01smN: SEQ ID NO: 4). The DNA sequence for B01smN was synthesized and then used to prepare the plasmid construct. In short, the DNA sequences of Xba1 and Xho 1 sites were added on both ends of the B01smN sequence. To create the expression plasmids, the Xba1/Xho1 containing plasmids were digested and the resulting DNA fragments were ligated into Xba1/Xho1 digested pET28a(+) and transformed into Top10 competent cells. A positive clone was confirmed by Xba I/Xho I digestion. The B01smN plasmid was transformed into E. coli and the cell bank was manufactured after three rounds of colony purification.

The E coli strain transformed with B01smN was amplified in semi-defined medium at 37° C. under agitation (pH 6.8—Dissolved oxygen: 20%). Expression of the antigen was induced by addition of isopropyl β-D-1-thiogalactopyranoside (IPTG).

The culture was harvested as unprocessed bulk and the bacterial biomass was separated from the media with centrifugation. The resulting cell pellets was resuspended in a buffer (20 mM Tris-HCl, pH 8.5). The resuspended pellet was processed through a homogenizer to produce cell homogenate. The homogenate was subsequently centrifuged to collect the supernatant fraction. The supernatant faction was then filtered.

The filtered supernatant was conditioned to pH 8.5 and <5.0 mS/cm conductivity and loaded onto a chromatography CaptoQ ImpRes, and purified in a bind and elute mode. The CaptoQ ImpRes elution pool is then conditioned to 1.8 M AmS for loading onto the second chromatography, Phenyl Sepharose HP. After elution, the material was concentrated and diafiltered into the acetate buffer (50 mM sodium acetate, 150 mM NaCl, pH 6.0) using 5 kDa Ultracel TFF membrane, then 0.2-μm filtered.

The B01smN was adsorbed onto $AlPO_4$ defined at 1.00 mg Al/mL of AlPO 4 in acetate buffer (50 mM sodium acetate, 150 mM NaCl, pH 6.0).

3. NadA

A truncated version of NadA was prepared from Nad-A_MC58. The truncated NadA has leader sequence (residues 1 to 23) and anchor domain (residues 308 to 362) of NadA_MC58 removed (truncated NadA: SEQ ID NO: 5). In the truncated sequence of NadA_MC58, the first amino acid after the leader sequence is alanine, which is replaced by a methionine. The DNA sequence for NadA was synthesized and then used to prepare the plasmid construct. DNA sequences of Xba1 and Xho 1 sites were added on both ends of the NadA sequence. To create the expression plasmids, the Xba1/Xho1 containing plasmids were digested and the resulting DNA fragments were ligated into Xba1/Xho1 digested pET28a(+) and transformed into Top10 competent cells. A positive clone was confirmed by Xba I/Xho I digestion. The NadA plasmid was transformed into E. coli and the cell bank was manufactured after three rounds of colony purification.

The E coli strain transformed with NadA1 was amplified in semi-defined medium at 37° C. under agitation (pH 6.8—Dissolved oxygen: 20%). Expression of the antigen was induced by addition of isopropyl β-D-1-thiogalactopyranoside (IPTG).

The culture was harvested as unprocessed bulk and the bacterial biomass was separated from the media with centrifugation. The resulting cell pellets was resuspended in a buffer (20 mM Tris-HCl, pH 8.5). The resuspended pellet was processed through a homogenizer to produce cell homogenate. The homogenate was subsequently centrifuged to collect the supernatant fraction. The supernatant faction was then filtered.

The supernatant fraction was loaded onto a Capto DEAE column. The Capto DEAE elution fraction is conditioned with powdered AmS until a concentration of 500 mM AmS is achieved. The conditioned Capto DEAE elution fraction is loaded onto a Toyopearl Butyl-650M column. The Toyopearl Butyl-650M elution fraction was loaded onto a CHT Type I 40 μm column and the CHT elution fraction is concentrated using a 30 kDa regenerated cellulose TFF membrane followed by diafiltration into 50 mM sodium acetate, 150 mM NaCl, pH 6.0. Following TFF, the product is 0.2-μm filtered to produce the NadA antigen.

NadA was adsorbed onto $AlPO_4$ defined at 1.00 mg Al/mL of AlPO 4 in acetate buffer (50 mM sodium acetate, 150 mM NaCl, pH 6.0).

4. dOMV

The dOMV was purified from wild-type N. meningitidis serotype B, strain 99M that was provided by the Walter Reed Army Institute of Research (WRAIR).

The Nm B 99M was cultured in a chemically defined medium described in Fu et al. (*Biotechnology* (N Y). 1995 February; 13(2):170-4) and in U.S. Pat. No. 5,494,808 in presence of yeast extract at 1 g/L and Hepes 1 M, at 37° C., under $CO_2$ 5%.

Culture harvest was carried out using a low-speed centrifugation of the heat-treated suspension (55° C. for 2 hours) in order to recover wet bacterial pellets. Two serial detergent-mediated extraction steps (56° C. for 15 minutes) were performed with extraction buffer composed of a detergent (sodium deoxycholate) to extract dOMV from the bacterial outer membrane and deplete lipooligosaccharides (as disclosed in Helting et al., *Acta Pathol Microbiol Scand*

C. 1981 April; 89(2):69-78). The sodium deoxycholate and EDTA solubilize the bacterial outer membranes which then re-organize themselves into dOMV (vesicles and particulates). Resuspension was completed by using Ultra-Turrax (rotor-stator equipment) to homogenize the pellets suspended in the extraction buffer. The dOMV supernatants were pooled before benzonase treatment in the presence of MgCl 2 (37° C. for 15 minutes).

Following the dOMV extraction, the concentration of dOMV was performed using hollow fibers in modified PolyEtherSulfone (mPES) of 300 kDa. Several ultracentrifugation steps are used to separate dOMV from the "soluble" content such as nucleic acids, cytosolic proteins, extracted lipopolysaccharides or buffer components. The resulting pellets were then resuspended in the extraction buffer using Ultra-Turrax (rotor-stator equipment) at the minimum speed for a few seconds. After primary resuspension, high pressure homogenization was used to fully resuspend dOMV in the extraction buffer and to increase accessibility of detergent to the dOMV surface.

Centrifugation was then performed prior to final filtration of supernatant with a 0.45/0.2-μm cellulose acetate filter.

5. Combinations of Antigens

The MenB antigens in the multicomponent immunogenic compositions are purified non-lipidated mutated A05 fHBP (A05tmN), non-lipidated mutated fHBP (B01smN), NadA and dOMV. The A05tmN, B01smN and NadA antigens were adsorbed to aluminum phosphate (AlPO$_4$).

The vehicle was consisting of acetate buffer (50 mM sodium acetate, 150 mM NaCl, pH 6.0) and AlPO$_4$ (1.00 mg AL$^{3+}$/mL).

To formulate the final immunogenic compositions formulations, AlPO$_4$, B01smN adsorbed onto AlPO$_4$, A05tmN adsorbed onto AlPO$_4$, and acetate buffer (50 mM sodium acetate, 150 mM NaCl, pH 6.0) were blended together to achieve target antigen and aluminum concentrations (250 μg/mL for B01smN, 250 μg/mL for A05tmN and 1.00 mg Al/mL of AlPO$_4$). Different NadA-dOMV compositions were formulated by blending dOMV with acetate buffer (50 mM sodium acetate, 150 mM NaCl, pH 6.0) and NadA adsorbed onto AlPO$_4$ to achieve the different concentrations of the antigens of the different formulations tested below (F1 to F5). The fHBPs only formulation was diluted in the carrier to achieve the formulation F6.

2. TRUMENBA®

TRUMENBA® is a MenB bivalent recombinant lipidated fHBP (rLP2086) composition in a sterile liquid suspension composed of fHBP subfamily A (A05) and B (B01) proteins formulated at 60 μg/mL/subfamily in 10 mM histidine buffer pH 6.0, sodium chloride (NaCl), and 0.5 mg/mL aluminum as aluminum phosphate (AlPO$_4$), and Polysorbate 80 (PS80).

3. BEXSERO®

BEXSERO® contains three recombinant proteins: rp287-953 (NHBA chimera) at 50 μg/0.5 mL dose, rp936-741 (fHBP chimera with non-lipidated B24 at 50 μg/0.5 mL dose), and rp961c (NadA) at 50 μg/0.5 mL dose; dOMV at 25 μg/0.5 mL dose and AlOOH at 1.5 mg/0.5 mL dose (e.g., 0.5 mg of Al) in a buffer comprising histidine 0.776 mg/0.5 mL dose, sodium chloride at 3.125 μg/0.5 mL dose, sucrose 10 mg/0.5 mL dose and water.

4. MENQUADFI®

MENQUADFI® is a commercially available vaccine comprising ACWY polysaccharides antigens obtained and conjugated to tetanus toxoid (TT) as disclosed in WO 2018/045286 A1. The formulation comprises the *N. meningitidis* capsular polysaccharides from serogroups A, C, Y, and W135, separately conjugated to tetanus toxoid protein. The target active ingredients concentrations are 10 μg of each polysaccharide and approximately 55 μg of tetanus toxoid protein per 0.5 mL dose. The antigens were formulated in a sterile, aqueous solution containing 30 mM sodium acetate buffer (1.23 mg/dose) and sodium chloride (0.67%, 3.35 mg/dose).

5. Tested Compositions

Six formulations of the MenB multicomponent vaccine as disclosed herein (F1-F5, and F1 co-administered with MENQUADFI) were tested and compared to the benchmark compositions BEXSERO, TRUMENBA and a comparative bivalent (fHBP A and fHBP B) composition (F6) in the following studies. The different amounts of the different antigens of the tested compositions are summarized in the following Table 1. F1, F2, F4-F6 and F1 co-administered with MENQUADFI comprised 0.4 mg AlPO$_4$ per dose while F3 comprised 0.8 mg AlPO$_4$ per dose.

TABLE 1

Formulations of the Tested Immunogenic Compositions

| Antigens | F1 | F2 | F3 | F4 | F5 | F6 | F1 co-administered with MENQUADFI | Trumenba | Bexsero |
|---|---|---|---|---|---|---|---|---|---|
| | Amount in μg per injected dose | | | | | | | | |
| fHBP A | 50 | 25 | 100 | 50 | 50 | 50 | 50 | 60 | |
| fHBP B | 50 | 25 | 100 | 50 | 50 | 50 | 50 | 60 | 50 |
| NadA | 50 | 50 | 50 | 50 | 50 | | 50 | | 50 |
| NHBA | | | | | | | | | 50 |
| dOMV | 50 | 50 | 50 | 25 | 125 | | 50 | | 25 |
| MENQUADFI (ACWY) | | | | | | | 4 × 10 + 55 μg of TT | | |

The following volume per formulation was used for administration in Example 2:

F1: 400 μL

F2: 400 μL

F3: 800 μL

F4: 400 μL

F5: 400 μL

F6: 400 μL

F1+MENQUADFI: Animals received 400 μL of F1 at D0, D28 and D56. On day 0 they also received 500 μl of MENQUADFI in the opposite thigh.

TRUMENBA: 500 μL

BEXSERO: 500 μL

Example 2: Preclinical Assessment of the MenB Vaccine Immunogenicity: Rabbit Immunogenicity Study

1. Materials & Methods
1. Study Design 9 groups of seven rabbits (New-Zealand KBL—females—8 weeks old) received three immunizations each of one of the seven formulations—referred as F1 to F6 and F1+MENQUADFI in Table 1 of Example 1—or the licensed benchmark vaccines TRUMENBA and BEXSERO (see Example 1) given by the IM route, on D0, D28 and D56. Formulation F1 was also tested in coadministration with MENQUADFI. Compositions were administered via the IM route in the right thigh for the first injection, in the left thigh for the second injection and in the right thigh for the last one. For the group receiving F1+MENQUADFI, animals were co-administered with MENQUADFI given by the IM route in the opposite thigh on D0.

Clinical signs and temperature were measured 4, 24 and 48 hours following the immunization. Blood samples were collected on D0 and two weeks after the second immunization (at D42), and at D63, in tubes containing clot activator and serum separator (BD Vacutainer SST II 8.5 mL, ref 366468A). Tubes were centrifuged at 3500 rpm for 15 min in order to separate serum from blood cells. The sera were transferred into 4.5 mL NUNC tubes and heat-inactivated at +56° C. for 30 min. The serum was stored at −20° C. until use for ELISA, purification and bacterial killing assays.

The plateau of the antibody response was already reached after the $2^{nd}$ dose, so the immunogenicity was analyzed after the $2^{nd}$ dose.

The immunogenicity of the tested compositions was measured on D42 by assessing antigen (Ag)-specific IgG response measured by ELISA and the functional serum bactericidal antibody activity (hSBA) against a panel of seven or eighteen MenB strains. A responder showed at least a 4-fold increase of hSBA between D0 and D42.

Positive threshold for positive response was defined as follows:

Pre (D0): hSBA<8—Post (D42): serum is positive if hSBA>8

Pre (D0): hSBA≥8—Post (D42): serum is positive if hSBA≥4-fold increase versus D0.

The number of immunized animals for which sera was able to induce a specific hSBA was greater than 70% of responders observed (i.e., 5/7 animals per formulation).

2. Determination of IgG Antibody Titers by ELISA

The specific IgG responses raised against each antigen were measured on D0 and D42 from rabbit sera. The ELISA analyses were performed from individual sera collected from each immunized group.

Briefly, 96-well micro-plates were coated with 100 µL per well of 1 µg/mL of specific antigen in the carbonate buffer coating solution and kept overnight at +4° C. Coating solution was removed by plates inversion followed by plate tapping on a paper towel. Free sites were blocked with 150 µL of buffer 1 (PBS/Tween20 0.05%/Skim milk 1%) and after a 60 min incubation period at +37° C., the plates were emptied. The sera were serially diluted in buffer 1 in a volume of 100 µL (12 times) in the microplates. The plates were incubated for 90 min at +37° C. and then washed with buffer 2 (PBS/Tween20 0.05%). Then, 100 µL of a diluted anti-rabbit IgG was added in each well. After 90 min incubation at +37° C., the plates were washed with buffer 2. The reaction was developed by adding 100 µL of a tetramethylbenzidine substrate solution in each well. The reaction was chemically stopped after 30 min at room temperature with HCl (1N) and absorbance was measured at 450-650 nm on a spectrophotometer (Versamax reader p 248, Molecular Devices). The results were expressed in arbitrary ELISA units/mL by the reciprocal of the dilution corresponding to the OD=1 using CODUNIT program for robotic ELISA.

3. IgG Purification of Rabbit Sera for hSBA Testing

To avoid non-specific bactericidal killing induced by rabbit sera on D0, D42, a purification of IgG was necessary. Purification of rabbit sera was performed using RPROTEIN A GRAVTITRAP™ columns (GE healthcare GE28-9852-54) and Ab Buffer Kit GE Healthycare ref 28-9030-59). After first step of equilibration of the columns with binding buffer (Phosphate Sodium 20 mM pH=7), the sera (2 mL) adjusted to neutral pH with binding buffer (V/V), were added on the column to perform IgG binding. Column were washed with binding buffer and eluted with Elution buffer (Glycine HCl 0.1M pH2.7) to collect IgG. To preserve activity of IgG, neutralizing buffer (Tris-HCl 1M, pH9.0) was added to the elution fraction to obtain a final approximatively neutral pH. Dialysis of each sample was performed using Slide-A-Lyser G2 Dialysis Cassette (Thermo Scientific 87730) to switch the samples in PBS buffer. Quantification of IgG concentration was done by NANODROP.

4. hSBA Testing

The measurement of serum bactericidal antibodies using human complement as the complement source is widely accepted as a surrogate marker of protection against meningococcal disease (Borrow et al., *Vaccine*. 2005; 23(17-18): 2222-7; Borrow et al., *Vaccine*. 2006; 24(24):5093-107; Frasch et al., *Vaccine*. 2009; 27 Suppl 2:B112-6; et al., *J Exp Med*. 1969; 129(6):1307-26).

The SBA assay measures the ability of the antibodies to lyse and kill bacteria in the presence of complement. The source of complement was a human complement (Pel Freez IgG/IgM depleted batch #13441). Briefly, sera were heat-inactivated 30 min at +56° C., then IgG purification was performed. Purified IgG were subsequently serially two-fold diluted (9 times) in Dulbecco PBS buffer containing Ca++ and Mg++)+0.2% gelatin (dilution buffer) in a 96 well microplate.

Preculture of bacteria was performed onto Mueller Hinton agar (Petri dish) for 18 h at +37° C. in 5% $CO_2$ to obtain confluent bacterial growth. Thereafter, bacteria were grown in BHI suspension, at initial OD of about 0.20 at λ 600 nm, for 2 h 30 at +37° C. with shaking (100 rpm). After incubation, bacteria were 5-fold diluted to obtain 1.4.104 CFU/mL. 25 µL of working bacteria suspension, 50 µL of pre-diluted sera and 25 µL of diluted human complement (15% final concentration) were deposit in a 96 well microplate and incubated at +37° C. for 1 hour with shaking (100 rpm). The Zephyr robotic application automatically deposited 40 µL of each well on square plate with Mueller Hinton agar (40*40). Agar plates were incubated at +37° C. with 5% CO2 for 10 12 hours. After incubation the number of colonies per well is counted by using Cybele Software from Microvision company.

The bactericidal titer is defined as the serum dilution that results a 50% decrease in colony forming units (CFUs) per mL of bacteria compared to complement control well. SBA titers are calculated by modeling a 4 parameters curve in Soft Max Pro v6.5.1 GxP by a user-defined protocol adapted to plate plan. If the modeling doesn't fit the 4-parameters curve, a trend function around the K50 and a manual reading was then applied; the bactericidal titer is defined as the final reciprocal serum dilution that results in at least a 50% decrease.

Positive threshold for positive response was defined as follows:

Pre (D0): hSBA<8—Post (D42): serum is positive if hSBA>8

Pre (D0): hSBA≥8—Post (D42): serum is positive if hSBA≥4-fold increase versus D0.

The number of immunized animals for which sera was able to induce a specific hSBA was greater than 70% of responders observed (i.e., 5/7 animals per formulation).

5. MenB Strains

A set of 18 wild-type serogroup B *N. meningitidis* isolates that were isolated from geographically distinct locations at different date of isolation, the majority being recent clinical isolates, and that represented diverse MLST Clonal Complexes were selected. MenB strains were selected in order to assess the immunogenicity of each component of the immunogenic compositions and to assess breadth of coverage. The immunogenicity was measured with an SBA using MenB strains selectively recognized by antibodies against one of the antigens of the composition while not matching any of the other antigens of the composition. Further, the selection was performed to ensure that some selected strains represent the well-described fHBP sequence diversity and distribution among both A and B subfamilies. The breadth of coverage was assessed using MenB strains representative of epidemiological characteristics such as Clonal Complex (CC) distribution, geographical origin, antigen prevalence and diversity.

The main features of the selected strains are listed in Table 2.

TABLE 2

Strains Selected to Measure Antigen-specific SBA Responses to the Vaccine Components

| MenB strain no | Antigen profile fHBP family variant type | NadA genotype | PorA VR2 P1.2 genotype | Clonal Complex |
|---|---|---|---|---|
| 1 | A56 | Absent | Mismatch | ST-213 |
| 2 | A22 | Absent | Mismatch | ST-41/44 |
| 3 | B44 | Absent | Mismatch | ST-269 |
| 4 | B24 | Absent | Mismatch | ST-32 |
| 5 | A10 | Absent | Match | ST-11 |
| 6 | B79 | NadA1 | Mismatch | ST-32 |
| 7 | A19 | Absent | Mismatch | ST-35 |
| 8 | A05 | NadA4/5 off | Mismatch | ST-213 |
| 9 | A12 | Absent | Mismatch | ST-41/44 |
| 10 | A47 | Absent | Mismatch | ST-35 |
| 11 | A06 | Absent | Mismatch | ST-461 |
| 12 | A15 | Absent | Mismatch | ST-103 |
| 13 | A10 | NadA 2/3 | Match | ST-11 |
| 14 | A07 | NadA1 | Mismatch | ST-32 |
| 15 | B16 | Absent | Mismatch | ST-41/44 |
| 16 | B03 | Absent | Mismatch | ST-41/44 |
| 17 | B09 | NadA4/5 off | Mismatch | ST-213 |
| 18 | B24 | NadA1 | Mismatch | ST-32 |

The 18 strains were selected on the basis of epidemiological characteristics such as Clonal Complex distribution, prevalence and hypervirulence of the Clonal Complex, geographical origin, antigen prevalence and diversity, and are characterized as followed with regards to the antigen distribution:

11 strains express fHBP subfamily A (2 close to the fHBP A05 antigen—no 1 & 8—and 9 distant from the fHBP A05 antigen—no 2, 5, 7, 9, 10, 11, 12, 13, 14) and 7 strains express fHBP subfamily B (1 close to the fHBP B01 antigen—no 3—and 6 distant from the fHBP B01 antigen—no 4, 6, 15, 16, 17, 18).

14 strains do not express NadA (gene absent or frameshift NadA4/5 off) and 4 strains express either the homologous NadA1 variant (3 strains) or the heterologous NadA2/3 variant (1 strains); and 2 strains express a matched PorA VR2 P1.2 of the dOMV, expressing a low level of fHBP A, one not expressing NadA protein (no 5) and one expressing a heterologous NadA protein (no 13).

2. Results

1. ELISA Results

Total IgG antibodies were quantified by ELISA on D0 (grey) from pooled sera and on D42 (blue) from individual sera collected from immunized rabbits with various formulations (F), TRUMENBA or BEXSERO.

Whatever the ELISA response, results were homogeneous within the groups (all p-values≥0.061). No outlier animal was detected.

Figure 1B:
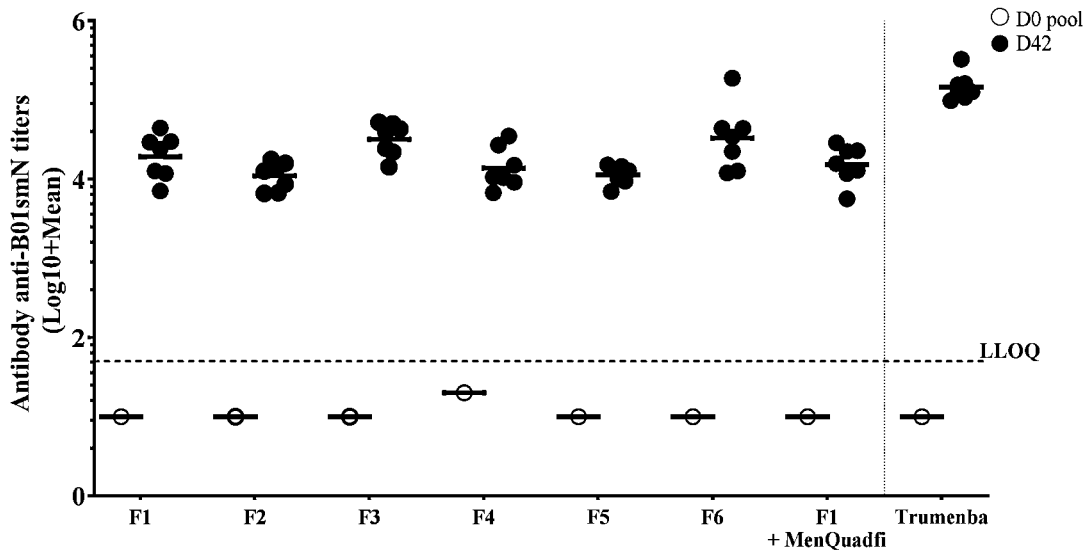
Figure 2A:
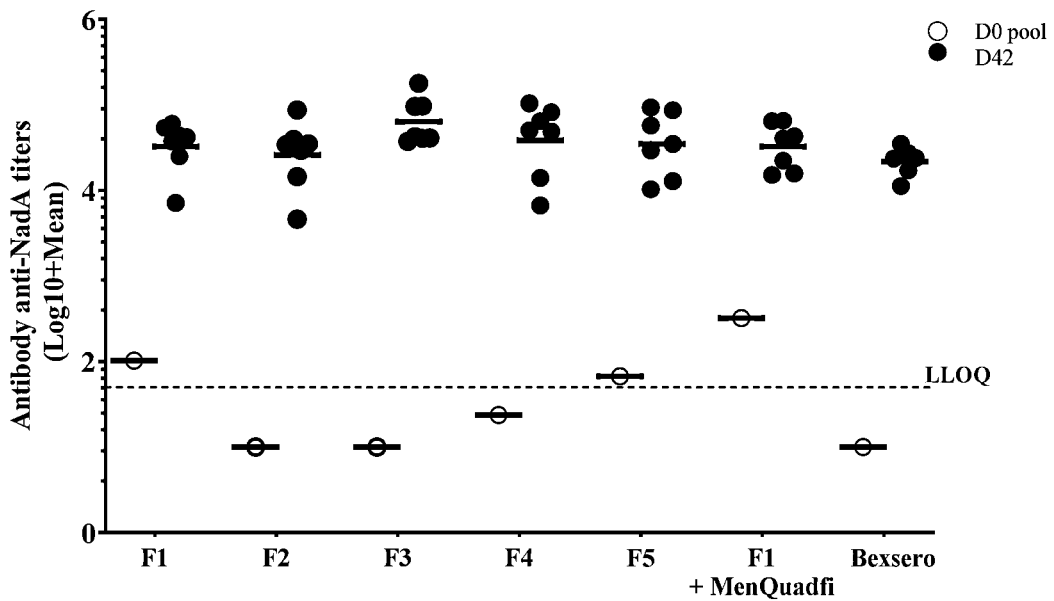
FIGS. 2A & 2B.
Figure 2B:
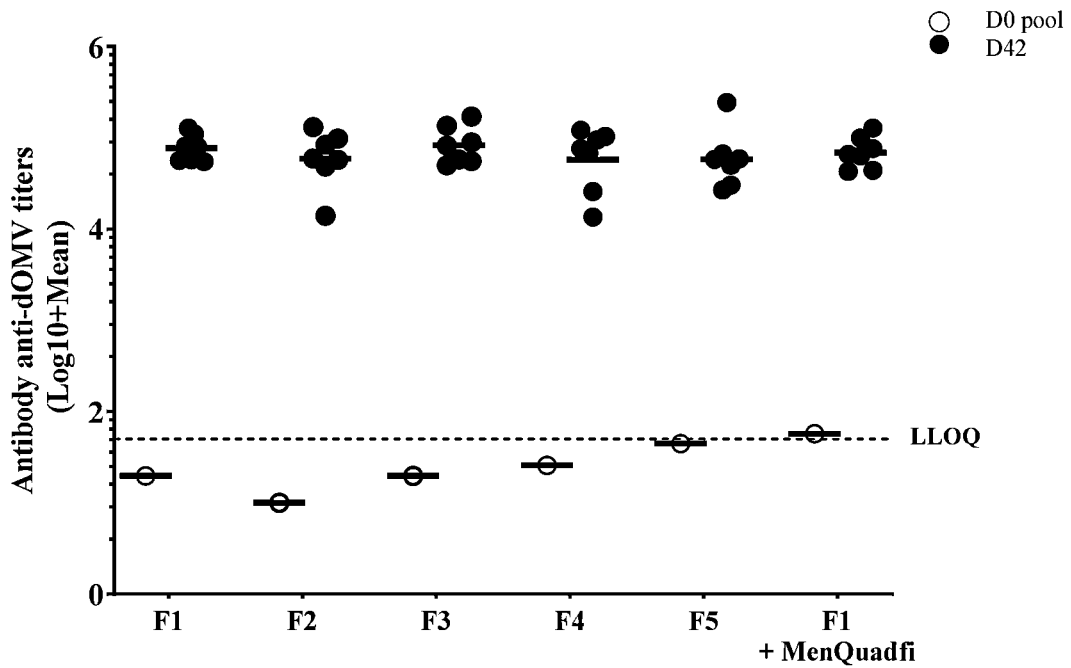

The ELISA results show that all the F1-F5 formulations and F1 formulation co-administered with MENQUADFI elicited an antibody response with Ag specific-IgG titers ranging from 4.05 to 4.99 Log 10, as depicted in FIGS. 1A & 1B for fHBP-specific IgG response, and FIGS. 2A & 2B for NadA-specific IgG response and dOMV-specific IgG response.

Furthermore, as depicted in FIGS. 1A & B and FIGS. 2A & 2B, whatever the formulation used, the injection of each of the four MenB antigens formulated in combination with $AlPO_4$ allowed production of antibodies in 100% of animals with moderate to high titers against fHBP A05 tmN, fHBP B01 smN, NadA proteins and dOMV. The formulations prepared with 50 μg of A05tmN and B01smN fHBP Ags (F1+/−MENQUADFI, F4, F5 and F6) induced fHBP-specific IgG responses with mean titers ranging from 4.28 Log 10 to 4.59 Log 10 and from 4.05 Log 10 to 4.52 Log 10, respectively. The formulations prepared with 50 μg of NadA (F1 to F5), induced NadA-specific IgG responses with mean titers ranging from 4.42 Log 10 to 4.81 Log 10. The formulations prepared with 50 μg of dOMV (F1 to F3) induced dOMV-specific IgG responses with mean titers ranging from 4.77 Log 10 to 4.99 Log 10. Finally, regarding the various doses of fHBP proteins (F2 at 25 μg and F3 at 100 μg) or of dOMV (F4 at 25 μg and F5 at 125 μg), similar mean titers were measured for all dosages.

TRUMENBA was able to induce specific IgG against fHBP A05 tmN, fHBP B01 smN antigens with mean titers of 5.16 and 5.15 Log 10, respectively.

BEXSERO was able to induce specific IgG against NadA variant 1 antigen with mean titers of 4.34 Log 10.

2. hSBA Results Obtained with the Different Compositions F1 to F6 or F1+MENQUADFI, TRUMENBA and BEXSERO Over 7 MenB Strains (No 1 to 6 and 18)

In a first set of experiments the different compositions F1 to F6 or F1+MENQUADFI, TRUMENBA and BEXSERO were assayed over 7 MenB strains (no 1 to 6 and 18).

The hSBA results show that the six formulations F1-F5 and F1 co-administered with MENQUADFI were immunogenic in rabbits. Percentage of responders is the percentage of animals with sera that were measured based on a post versus pre-immunization with a 4-fold increase of hSBA GMT, demonstrating the surrogate of protection.

Figure 3:
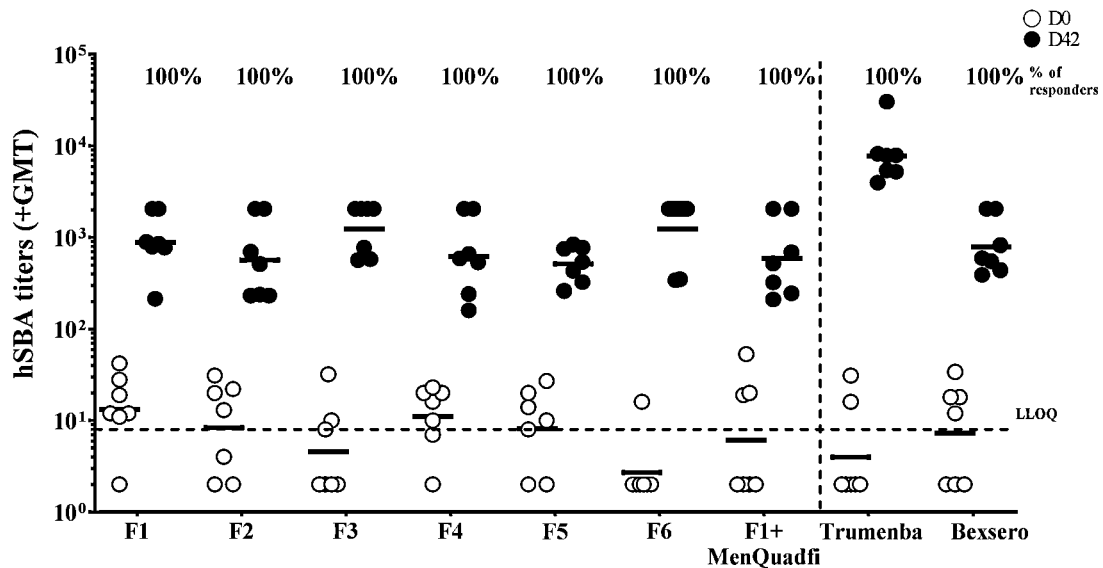
FIG. 3 represents the hSBA measured against a closely-related MenB B44 strain (strain no 3) in purified IgG on D0 (Open/White symbols) and D42 (Closed/Black symbol) from rabbits immunized on D0, D28 and D56 with TRUMENBA, BEXSERO or the Formulations F1 to F6 or F1 co-administered with MENQUADFI.

As depicted in FIG. 3, whatever the immunization dose used (25 μg F2, 50 μg F1, F4, F5, F6 and 100 μg F3), the mutated non-lipidated fHBP B01 smN in combination with the mutated non-lipidated fHBP A05 tmN+NadA+dOMV was able to induce at D42 bactericidal activity in 100% of animals against the closely-related fHBP B44 variant strain with GMT ranging from 443 to 1147.

TRUMENBA and BEXSERO were able to induce bactericidal activity in 100% of animals against a MenB strain expressing a closely-related fHBP B44 variant with GMT of 5773 and 646 respectively.

Figure 4:
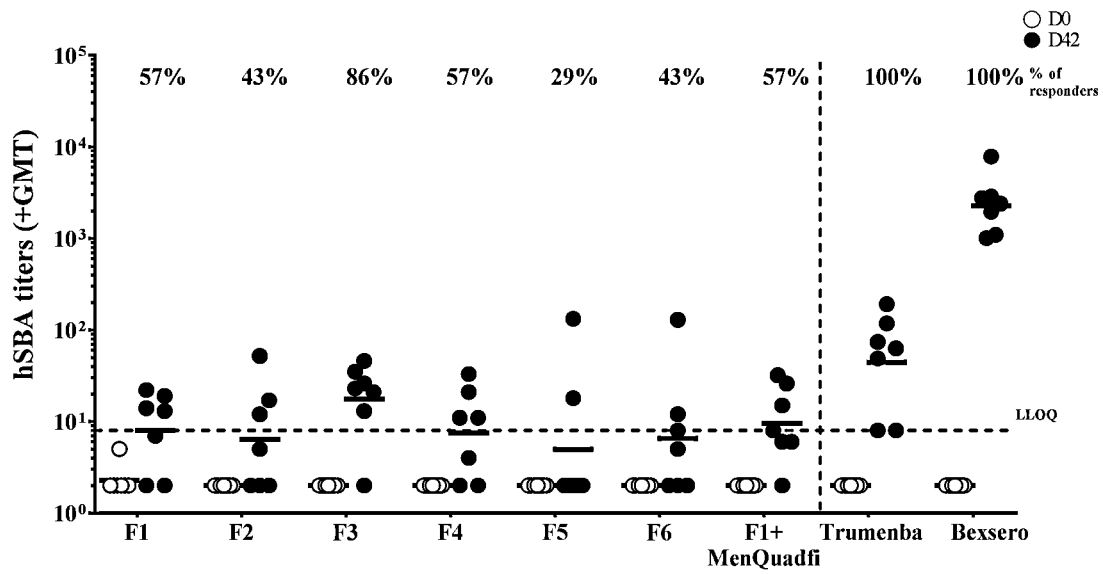
FIG. 4 represents the hSBA measured against a heterologous MenB B24 strain (strain no 4) in purified IgG on D0 (Open/White symbols) and D42 (Closed/Black symbol) from rabbits immunized on D0, D28 and D56 with TRUMENBA, BEXSERO or the Formulations F1 to F6 or F1 co-administered with MENQUADFI.
Figure 5:
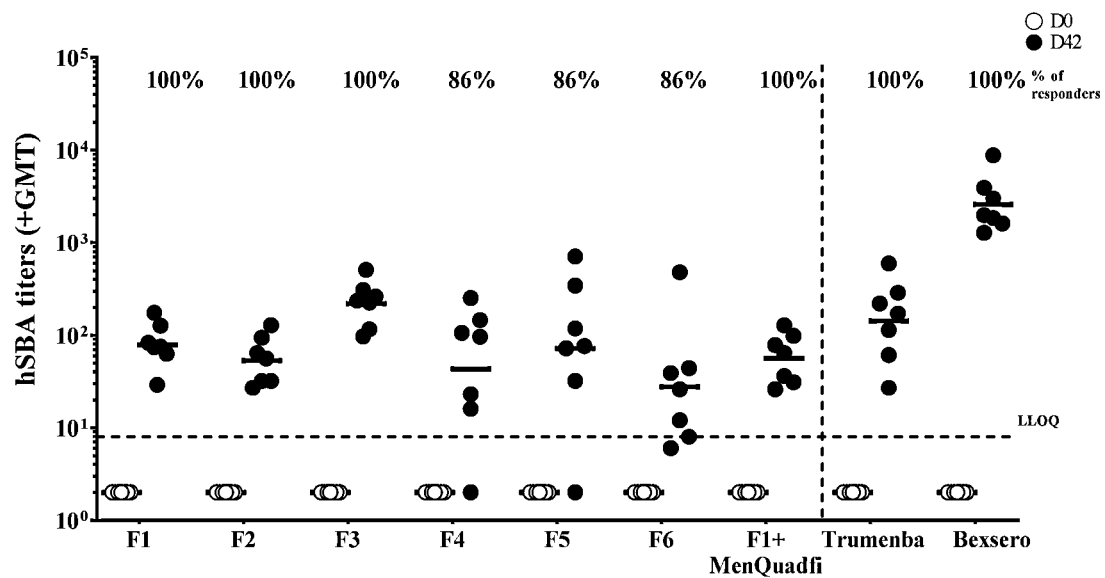
FIG. 5 represents the hSBA measured against a heterologous MenB B24 strain (strain no 18) in purified IgG on D0 (Open/White symbols) and D42 (Closed/Black symbol) from rabbits immunized on D0, D28 and D56 with TRUMENBA, BEXSERO or the Formulations F1 to F6 or F1 co-administered with MENQUADFI.

As depicted in FIGS. 4, and 5, the mutated non-lipidated fHBP B01 smN in combination with the mutated non-lipidated fHBP A05tmN+NadA+dOMV was able to induce bactericidal activity in 43 to 86% of animals against a first MenB strain expressing a divergent fHBP B24 variant (FIG. 4) and in 86 to 100% of animals against a second divergent fHBPB24 variant strain tested (FIG. 5) with GMT ranging from 5 to 18 and from 28 to 219 respectively.

Of interest, against the first heterologous B24-variant strain, only the mutated non-lipidated fHBP B01smN in formulation F3 induced hSBA response in 86% animals, with GMT at 18.

TRUMENBA was able to induce bactericidal activity in 100% of animals against the two B24 strains with GMT of 44 and 143, respectively. BEXSERO was able to induce bactericidal activity in 100% of animals against the two B24 strains with GMT of 2274 and 2587, respectively.

Furthermore, no significant dose effect was shown between 25 to 100 μg B01 smN fHBP doses (all p-values≥0.056).

Finally, no significant difference was shown on the mutated non-lipidated B01 smN response when the MENQUADFI was co-administered with the Formulation F1 (all MenB Ags at 50 μg, all p values≥0.339).

Figure 6:
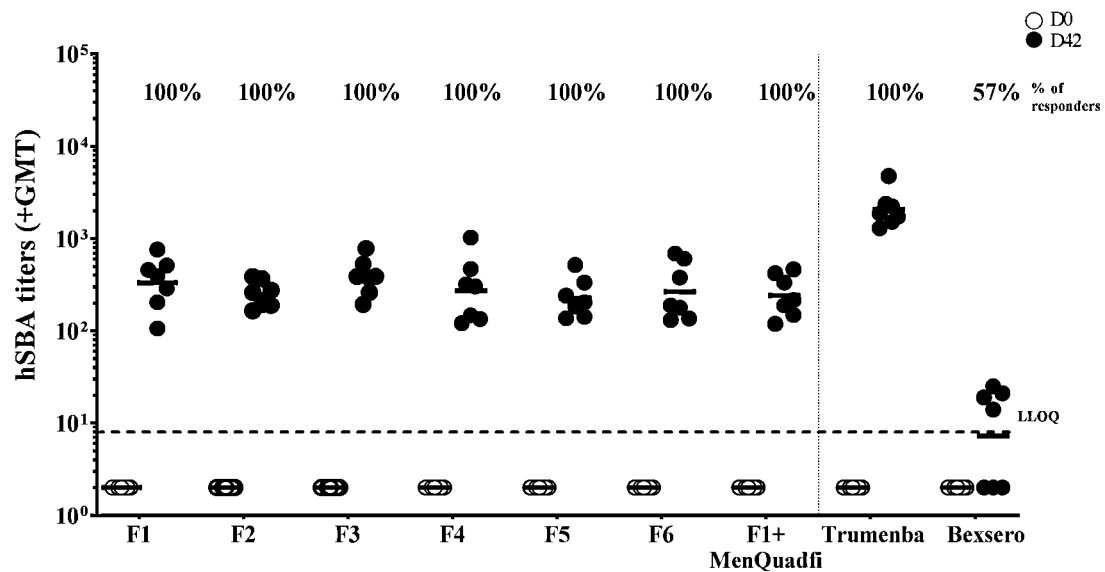
FIG. 6 represents the hSBA measured against a closely-related MenB A56 strain (strain no 1) in purified IgG on D0 (Open/White symbols) and D42 (Closed/Black symbol) from rabbits immunized on D0, D28 and D56 with TRUMENBA, BEXSERO or the Formulations F1 to F6 or F1 co-administered with MENQUADFI.
Figure 7:
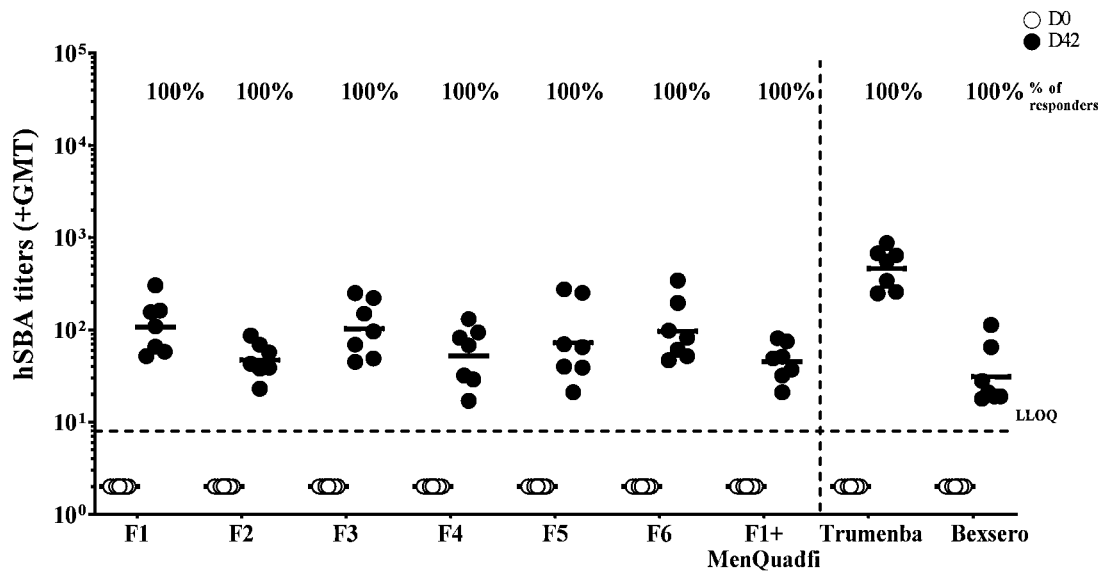
FIG. 7 represents the hSBA measured against a heterologous MenB A22 strain (strain no 2) in purified IgG on D0 (Open/White symbols) and D42 (Closed/Black symbol) from rabbits immunized on D0, D28 and D56 with TRUMENBA, BEXSERO or the Formulations F1 to F6 or F1 co-administered with MENQUADFI.

As depicted in FIGS. 6 and 7, whatever the immunization dose used (25 μg F2, 50 μg F1, F4, F5, F6 and 100 μg F3), the mutated non-lipidated fHBP A05 tmN in combination with the mutated non-lipidated fHBP B01smN+NadA+dOMV was able to induce bactericidal activity in 100% of animals against the closely-related fHBP A56 variant expressing strain (FIG. 6) and the divergent fHBP A22 variant expressing strain (FIG. 7), with geometric mean titers (GMT) ranging from 226 to 382 and from 45 to 108 respectively.

TRUMENBA was able to induce bactericidal activity in 100% of animals against fHBP A56 and fHBP A22 variant expressing strains with GMT of 2058 and 463 respectively. BEXSERO was able to induce bactericidal activity in 57% of animals against a fHBP A56 variant expressing strain and in 100% of animals against a fHBP A22 variant expressing strain with GMT of 7 and 331 respectively.

Furthermore, no significant dose effect was shown between 25 to 100 μg of the mutated non-lipidated A05 tmN fHBP doses (all p-values 0.066).

Finally, no significant difference was shown on the mutated non-lipidated A05 tmN response when the MENQUADFI was co-administered with the Formulation F1 against the A56 strain (p values=0.281). For hSBA against fHBP A22 expressing strain, titers obtained with F1+MENQUADFI were significantly lower than those obtained with F1 alone (p=0.020) however with 2.4-fold decrease that has no biological relevance.

Figure 8:
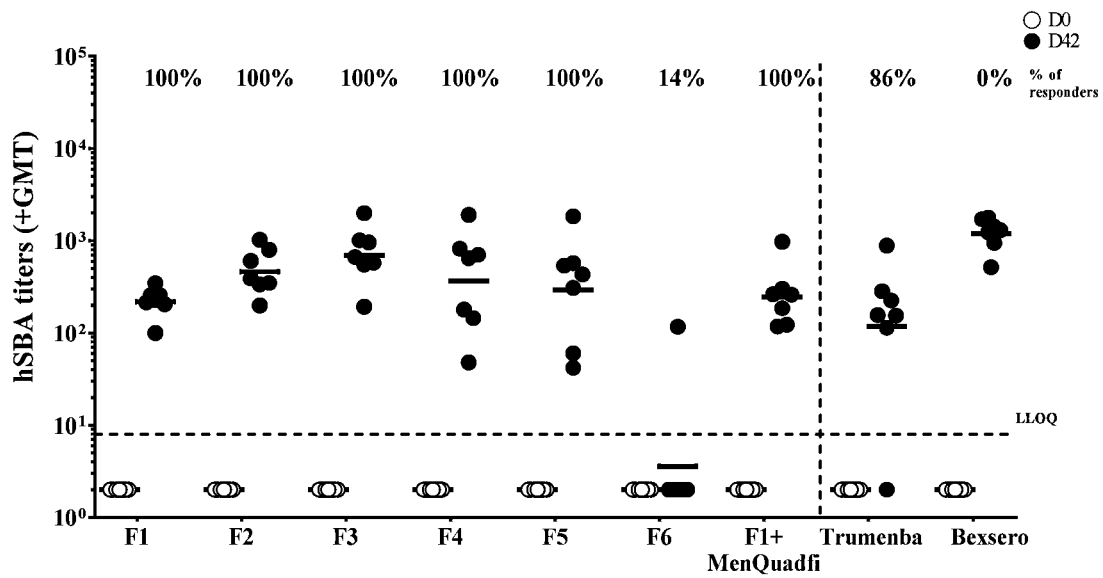
FIG. 8 represents the hSBA measured against a MenB NadA1 strain (strain no 6) in purified IgG on D0 (Open/White symbols) and D42 (Closed/Black symbol) from rabbits immunized on D0, D28 and D56 with TRUMENBA, BEXSERO or the Formulations F1 to F6 or F1 co-administered with MENQUADFI.

As depicted in FIG. 8, the formulations prepared with 50 μg of NadA (F1 to F5) were able to induce bactericidal activity in 100% of animals against the homologous NadA variant 1 strain with GMT ranging from 217 to 696.

TRUMENBA and BEXSERO were able to induce bactericidal activity in 86 and 100% of animals against the homologous NadA variant 1 strain with GMT of 118 and 1191, respectively.

Finally, no significant difference was shown on the NadA response when MENQUADFI was co-administered with the multicomponent MenB vaccine (p-values=0.688).

Figure 9:
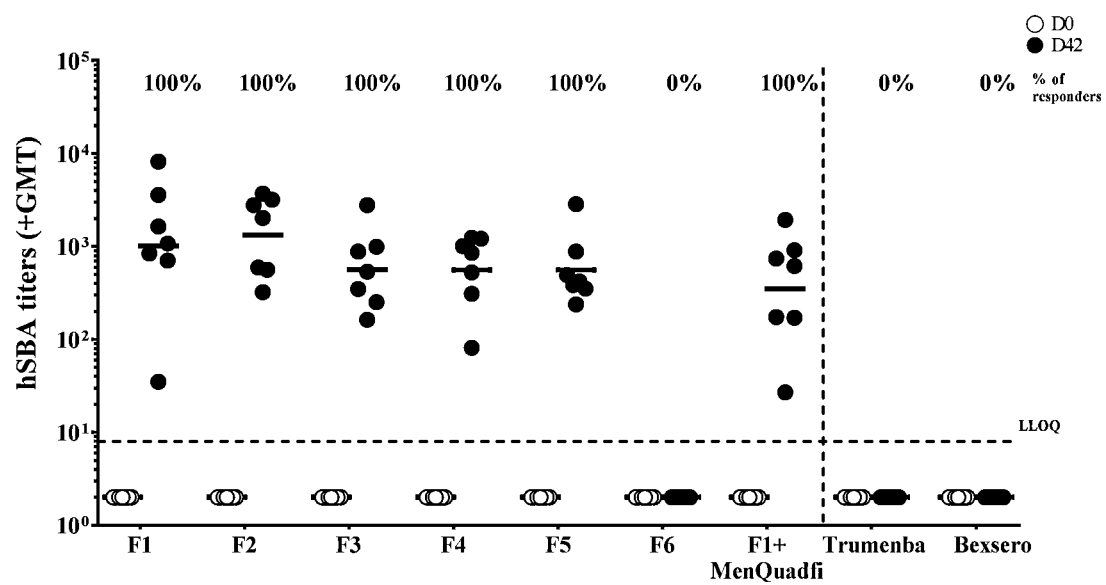
FIG. 9 represents the hSBA measured against a MenB OMV PorA 1.2 strain (strain no 5) in purified IgG on D0 (Open/White symbols) and D42 (Closed/Black symbol) from rabbits immunized on D0, D28 and D56 with TRUMENBA, BEXSERO or the Formulations F1 to F6 or F1 co-administered with MENQUADFI.

As depicted in FIG. 9, whatever the formulation prepared with dOMV at 25 μg F4, 50 μg F1, F2, F3 and 125 μg F5, dOMV was able to induce bactericidal activity in 100% of animals against the homologous PorA_1.2 strain with GMT ranging from 350 to 1324.

TRUMENBA and BEXSERO were not able to induce bactericidal activity against this dOMV strain.

Furthermore, no significant dose effect of dOMV was shown (all p-values 0.637).

No significant impact of NadA and dOMV antigens was observed on the fHBP A or B responses (all p-values 0.208).

The only significant impact of the dose of fHBP antigens combined with the NadA/dOMV antigens was for the NadA specific hSBA response between F1 (50 μg) and F3 (100 μg) formulation. As depicted in FIG. 8A, titers obtained with F3 formulation were higher than those obtained with F1 formulation (p=0.004, 3.2-fold increase). No significant difference between all the formulations was shown for the porA/dOMV-specific hSBA response.

This study demonstrated the immunogenicity of each of the four selected MenB antigens, the mutated non-lipidated fHBPs A05 tmL and B01 smL, NadA and dOMV, in combination, formulated with $AlPO_4$.

All antigens included in the new vaccine formulations were able to mount an Ag-specific bactericidal antibody response measured by hSBA against Ag-specific MenB strains. In the rabbit model, no significant dose effect was observed for fHBP. Similarly, no significant dose effect was observed for dOMV and dOMV at the lowest dose (25 μg) provides potent hSBA response. Of interest, formulation F3, i.e., containing fHBP at 100 μg, NadA at 50 μg and dOMV at 50 μg/dose, tends to provide the highest hSBA response and induced a positive response in more than 71% of animals against all strains tested. In addition, no impact of MenQuadfi coadministration was observed on the MenB-specific hSBA response. fHBP A05tmN vaccine Ag, in all tested formulations, induced hSBA response in 100% of animals against the closely related A56- and the heterologous A22-variant strains, with Geometric Mean Titer (GMT) ranging from 226 to 382 and from 45 to 108, respectively. fHBP B01smN vaccine Ag, in all tested formulations, induced hSBA response in 100% of animals against the closely related B44-variant strain with GMT ranging from 443 to 1147. When testing hSBA response against a first heterologous H44/76 B24-variant strain, only fHBP B01smN in formulation F3 induced a positive hSBA response in 86% animals, with GMT at 18, whereas all the other tested formulations induced hSBA response in only 29 to 57% of animals with GMT ranging from 5 to 10. In contrast, when using a second heterologous B24 strain, strain 03S-0291, fHBP B01smN, in all tested formulations, induced hSBA in 86 to 100% of animals with GMT ranging from 28 to 219.

NadA vaccine Ag, in all formulations tested, induced hSBA in 100% of animals against the NadA1 variant strain, with a GMT ranging from 217 to 696.

dOMV, in all formulations tested, induced hSBA in 100% of animals against the PorA subtype VR2 P1.2 strain, with GMT ranging from 350 to 1324.

Overall, immunogenicity results show that the six formulations of the immunogenic compositions disclosed herein were immunogenic in rabbits. All antigens included in the new vaccines were able to mount an Ag-specific bactericidal antibody response measured by hSBA against Ag-specific MenB strains. In the rabbit model, no significant dose effect was observed for fHBP, even if formulation prepared with 100 μg of fHBP tended to provide the highest hSBA response and also induced a response in more than 70% of animals against all strain tested. Similarly, no significant dose effect was observed for dOMV and the lowest dOMV dose (25 µg) was sufficient to induce a potent hSBA response. Of interest, no impact of MENQUADFI coadministration was observed on the MenB-specific hSBA response.

Of note, no temperature increases and no major findings (such as erythema . . . ) were observed in animals throughout the study.

In conclusion, immunogenicity results show that the six formulations of the immunogenic compositions disclosed were immunogenic in rabbits. All antigens included in the MenB multicomponent vaccine were able to mount an Ag-specific bactericidal antibody response measured by hSBA against Ag-specific MenB strains.

3. hSBA Results Obtained with the Compositions F1. F3. TRUMENBA and BEXSERO Over the 17 MenB Strains (No 1 to 17)

In a second set of experiment the sera obtained after immunization in the preceding experiments with compositions F, F3, TRUMENBA and BEXSERO were assayed over 11 additional MenB strains (for a total of 17 MenB strains including the 6 strains tested above).

The overall results are summarized in the Table 3 below representing the efficacy of the different tested compositions against the panel of selected MenB strains.

Figure 19:
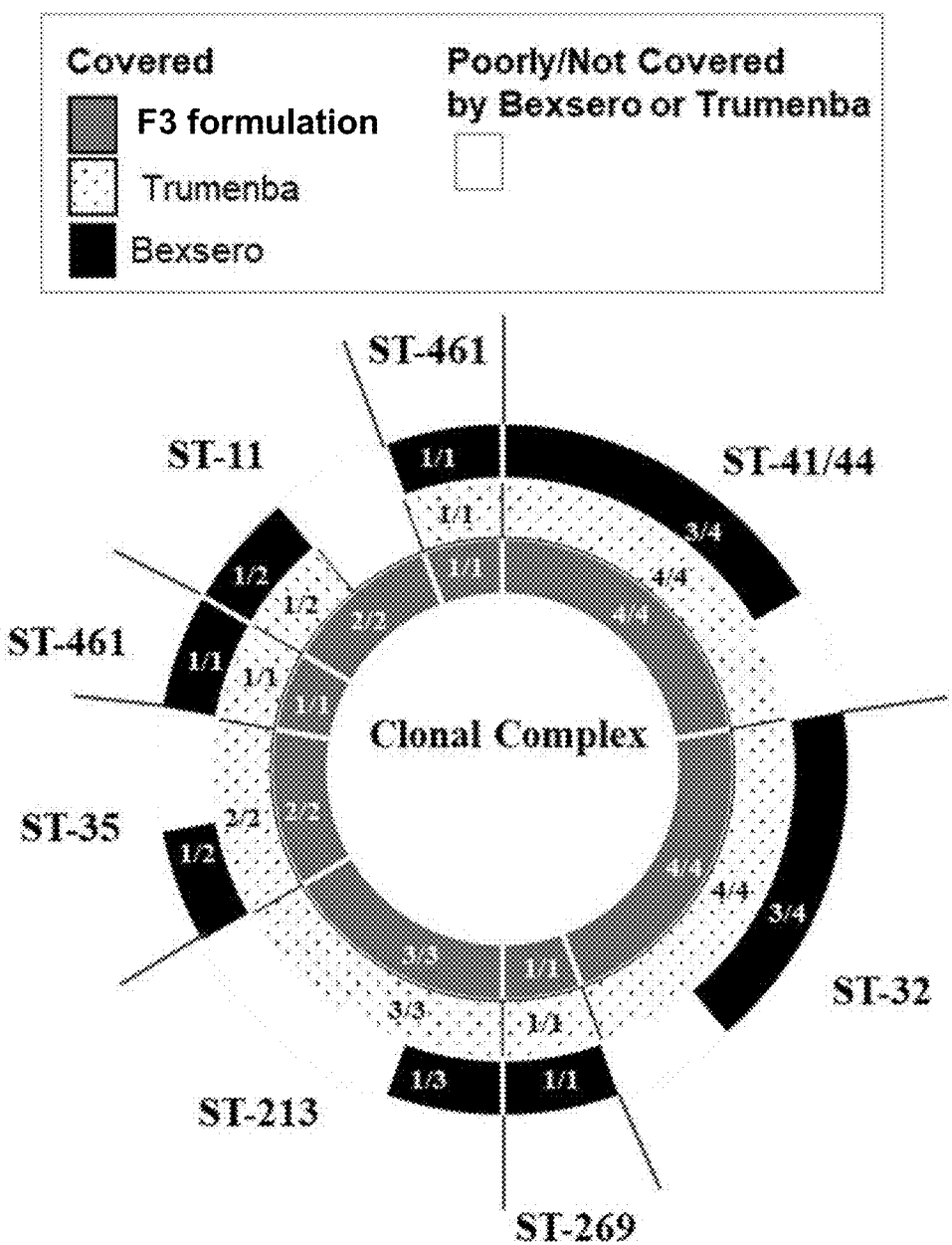
FIG. 19 represents a summary of the hSBA results illustrating the different Clonal Complexes covered or not covered by the different formulations tested: F3, TRUMENBA and BEXSERO on the 18 MenB strains from different Clonal Complexes. Black circle arcs: BEXSERO. Dotted circle arcs: TRUMENBA. Grey circle arcs: F3 formulations. Numbers within the circle arcs indicate the number of MenB strains covered by the formulations out of the total number of MenB strains tested per Clonal Complex.

As shown on FIG. 19, the tested formulation F3, was able to induce a protection over all the different MenB strains from the different Clonal Complexes, ST-41/44, the ST-32, the ST-269, the ST-213, the ST-35, the ST-461, the ST-11 and ST-461. In contrast, the coverage induced by TRUMENBA and BEXSERO present some gaps.

In conclusion of the data, it can be noted that the MenB multicomponent immunogenic compositions of the disclosure provide a good strain coverage, even against fHBP low expressor and divergent strains. The F3 formulation covered 17/17 MenB strains with >71% responders, and the F1 formulation covered 16/17 MenB strains with >71% responders.

TRUMENBA covered 15/17 MenB strains. The strain not covered (0% responders) was null for fHBP A10 expression and belonged to the ST-11 Clonal Complex. The strain poorly covered (71% responders) was a B24 expressing strain.

BEXSERO covered 11/17 MenB strains. The 6 strains poorly or not covered (0-57% responders) expressed fHBP A variants. They may represent up to 29% of the circulating MenB strains and belonged to prevalent or hypervirulent Clonal Complexes: ST-213; ST-11; ST-35; and ST-461.

The newly developed vaccine composition presents an increased breadth of protection over the 18 strains representative of the current MenB molecular epidemiology; i.e.,

TABLE 3

Efficacy of Tested Compositions Against a Panel of MenB Strains

| Compos. | F1 | | F3 | | Trumenba | | Bexsero | |
|---|---|---|---|---|---|---|---|---|
| MenB strains | GMT | %* | GMT | %* | GMT | %* | GMT | %* |
| 1 | 2.5 | 100 | 2.6 | 100 | 3.3 | 100 | 0.8 | 57 |
| 2 | 2.0 | 100 | 2.0 | 100 | 2.7 | 100 | 1.5 | 100 |
| 3 | 2.9 | 100 | 3.1 | 100 | 3.8 | 100 | 2.8 | 100 |
| 4 | 0.9 | 57 | 1.3 | 86 | 1.6 | 71 | 3.4 | 100 |
| 5 | 3.0 | 100 | 2.8 | 100 | 0.3 | 0 | 0.3 | 0 |
| 6 | 2.3 | 100 | 2.8 | 100 | 3.1 | 86 | 3.1 | 100 |
| 7 | 2.3 | 86 | 2.8 | 100 | 3.4 | 100 | 2.1 | 57 |
| 8 | 2.2 | 100 | 2.2 | 100 | 2.9 | 100 | 0.5 | 14 |
| 9 | 1.7 | 100 | 2.0 | 100 | 2.6 | 100 | 1.1 | 43 |
| 10 | 2.3 | 86 | 2.5 | 100 | 3.1 | 100 | 3.1 | 100 |
| 11 | 1.5 | 100 | 1.8 | 100 | 1.2 | 86 | 0.6 | 29 |
| 12 | 1.5 | 100 | 2.0 | 100 | 2.6 | 100 | 1.5 | 100 |
| 13 | 2.2 | 100 | 2.7 | 100 | 2.6 | 100 | 2.2 | 100 |
| 14 | 3.4 | 100 | 3.5 | 100 | 2.4 | 100 | 3.0 | 100 |
| 15 | 1.6 | 100 | 1.8 | 100 | 3.1 | 100 | 3.4 | 100 |
| 16 | 2.1 | 100 | 2.1 | 100 | 3.4 | 100 | 2.9 | 100 |
| 17 | 1.4 | 86 | 1.9 | 100 | 2.8 | 100 | 2.3 | 100 |

*: percentage of responders

The results showed that strains no 4 and 5 were poorly (<71% responders) or not covered (0% responders) by TRUMENBA. While these strains were covered in a greater extent or completely by the F1 and F3 formulations.

Also, the results showed that the strains no 1, 5, 7, 8, 9, and 11 were poorly or not covered by BEXSERO, while they tended to be well or completely covered by the F1 and F3 formulations.

Of note, the strain no 5 is not covered at all by TRUMENBA or BEXSERO.

The Table 3 shows that 16 out 17 and 17 out 17 of the MenB strains were covered by the F1 and F3 compositions. By contrast, TRUMENBA appeared to cover 15 out 17 of the MenB strains, and BEXSERO only 11 out 17 of the MenB strains.

strains from the most prevalent and hypervirulent Clonal Complexes (CC) and from the most prevalent antigen variants.

Example 3: MIMIC PTE Assay

1. Materials & Methods
1. Tested Compositions & Design of Experiment

In a first study, commercially available vaccines BEXSERO and TRUMENBA were compared in MIMIC adult and neonate Peripheral Tissue Equivalent (PTE) cultures (see below) using 20 donors each. TRUMENBA and BEXSERO vaccine compositions were as disclosed in Example 1.

In a second study, MIMIC PTE cultures (see below) were treated with five vaccine candidate formulations—F1, F2, F3; F4 and F5 (formulations were as indicated in Table 1 of Example 1)—in a dose range curve from 1:100 to 1:1000000, based on 10-fold dilutions of the human dose. F1 is considered the standard formulation as it contains 50 μg/dose of each component and a standard dose of AlPO4 (0.4 mg/dose); the F2 formulation is a combination of a low dose fHBP (25 ug/dose) and standard doses of NadA and dOMV (50 μg/dose) in 0.4 mg/dose $AlPO_4$; the F3 formulation is a combination of a high-dose fHBP (100 μg/dose), standard doses of NadA and dOMV (50 μg/dose), and a high dose of AlPO4 (0.8 mg/dose); the F4 formulation combines standard doses of fHBP and NadA (50 μg/dose each), a low dose of dOMV (25 μg/dose), and a standard dose of AlPO4; and the F5 formulation includes a combination of standard doses of fHBP and NadA (50 μg/dose), a high dose of dOMV (125 μg/dose), and a standard dose of $AlPO_4$. In this study, the dOMV-based MenB vaccine, BEXSERO, was used as a benchmark reference control.

The mock or control composition was a no treatment control containing serum free culture media only.

2. Adult and Neonate MIMIC PTE Assay

The MIMIC PTE construct (Higbee et al., *Altern Lab Anim.* 2009 September; 37 Suppl 1:19-27) was assembled on a robotic line using the method taught in Ma et al. (*Immunology*, 2010, 130: 374-87).

Briefly, endothelial cells were grown to confluence atop a collagen matrix (Advanced Biomatrix, San Diego, CA). Thereafter, donor PBMCs (adult MIMIC PTE) or donor cord bloods (Neonate MIMIC PTE) prepared from frozen stocks were applied to the assay wells. After an incubation of 90 minutes (adult version) or 3 hours (cord blood version), non-migrated cells were washed off prior to adding the various treatments (Table 1 of Example 1) in a final incubation step for 48 hours. A mixture of 100 ng/mL LPS (from *Pseudomonas aeruginosa*, Cat #L8643, Millipore Sigma, Burlington, MA) and 10 μg/mL R848 (Cat #TLRL-R848, InvivoGen, San Diego, CA) was used as a positive control (assay control) in these assays. Reverse-migrated cells were harvested after a 48 hours treatment period and phenotyped for cell viability using Flow Cytometry, while culture supernatants harvested at the same time pointe were analyzed for cytokines/chemokines by a multiplex assay.

In a first series of experiments, BEXSERO and TRUMENBA were compared together. In a second series of experiments, immunogenic compositions of the disclosure F1, F2, F3, F4 and F5 were compared to BEXSERO.

The culture supernatants were harvested after a 48-hr treatment period and analyzed for cytokines/chemokines by a multiplex assay. Cells, harvested at the same time point, were phenotyped for cell viability using flow cytometry.

3. Cytokine/Chemokine Analysis

MIMIC culture supernatants were analyzed using the Milliplex human 12-plex multi-cytokine detection system (Millipore). The kit includes IL-1β, IL-6, MIP-1β and TNFα. Analyte concentrations were calculated based on relevant standard curves using the Bio-Plex manager software (Luna et al. PloS One vol. 13,6 e0197478. 6 Jun. 2018).

For run acceptance criteria, the lower limit of quantification (LLOQ) and the upper limit of quantification (ULOQ) for each analyte was established based on the percent recovery (Observed/Expected*100) of each point against a 5-parameter logistic (5PL) curve fit of the standard values. A recovery percentage of 80%-120% was considered acceptable, such that values falling within this range define the lower and upper bounds of the standard curve. The raw data file was reviewed for bead counts; a data point was considered valid when a minimum of 35 beads per region was counted.

4. Flow Cytometry

MIMIC® PTE-derived cells were washed with PBS and stained with Live-Dead Aqua (InvitroGen, Carlsbad, CA) for 20 min on ice to assess for cell viability. Data analysis was performed using FlowJo software (Tree Star, Ashland, OR). For flow gating, singlets were selected, followed by live cells.

5. Data Analysis and Graph Plotting

Data were exported to GraphPad Prism (GraphPad Software, San Diego, CA, USA) for graph preparation. Cytokine data was exported into excel databases. Out-of-range high (>OOR) values (values higher than the highest point of the curve) were replaced with ULOQ; out-of-range low (<OOR) values were replaced with ½ the LLOQ (Lower limit of quantification).

6. Statistical Analysis

Statistical analyses were performed using a non-inferiority model. Parameters including cell viability, CD86, IL-6, IL-1b, TNF-a, and MIP-1b were employed as endpoints for this analysis. Geometric means (GMs) for different antigen formulations vs Bexsero® vaccine were compared and $\delta=\frac{2}{3}$ was used as the measure of non-inferiority. The analysis described here was done using the SA procedure, PROC TTEST, and is represented in dot plot graphs showing GM and 95% Cl range, as recommended in published literature.

2. Results

1. BEXSERO and TRUMENBA in Adult and Neonate MIMIC PTE

Culture supernatants from untreated and treated adult and neonate MIMIC PTE cultures were harvested after 48 hours and analyzed for cytokine/chemokine secretion using a Millipore custom multiplex array. The innate chemokines/cytokines IL-6, TNFα, MIP-1β and IL-1β were included in this analysis since they are critical for innate immune activity and can also drive immune-cytotoxicity.

Figure 10:
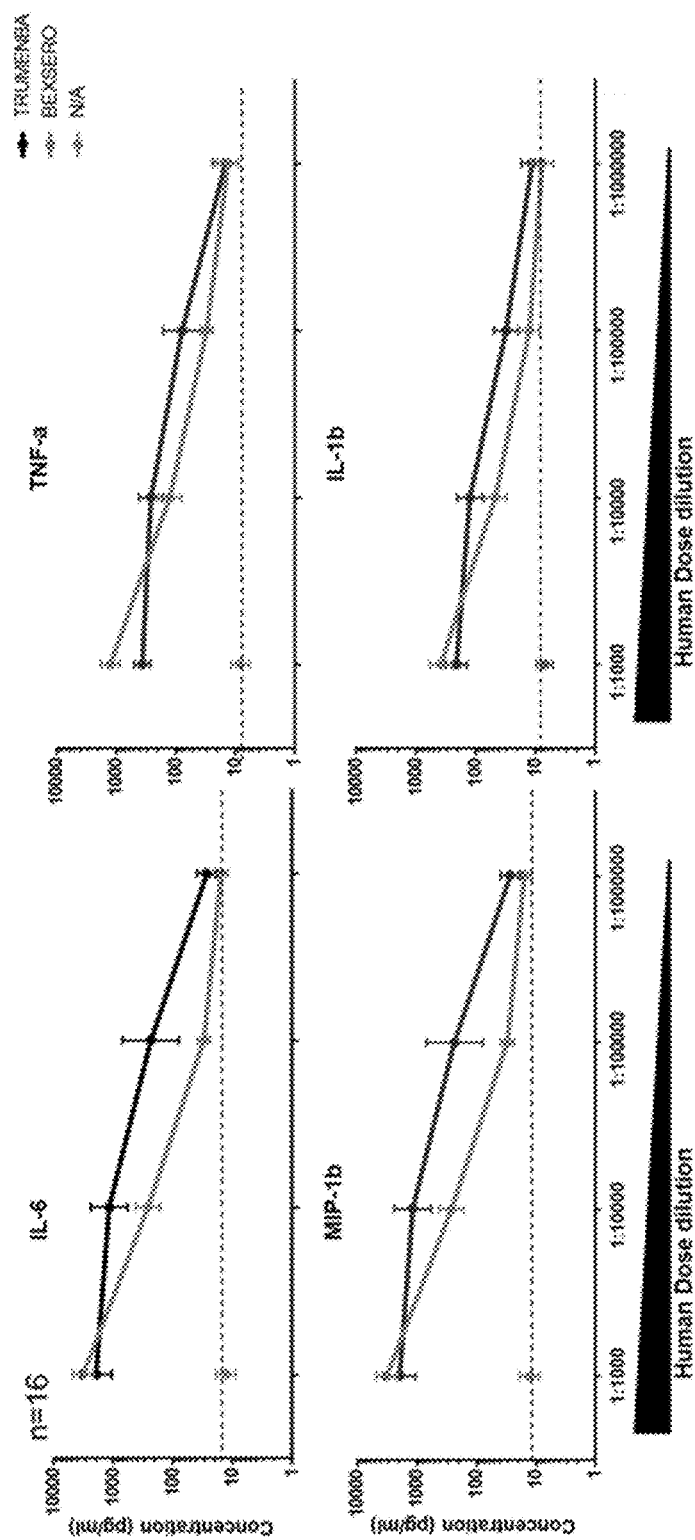
FIG. 10 represents the cytokine production (IL-6, TNFα, MIP-1β and IL-1β) of adult PTE derived dendritic cells (DCs) treated with different doses of BEXSERO and TRUMENBA: culture supernatants from PTE were harvested 48 hrs. post-treatment and evaluated for cytokine secretion using multiplex array. Graphs represent Geometrical Mean Value (GMV) of cytokine production of IL-6, TNFα, IL-1β, and MIP-1β, in dendritic cells (DCs). Treatments were in 10-fold dilutions of the human dose (n=20 donors). N/A is mock control with no antigen.
Figure 11:
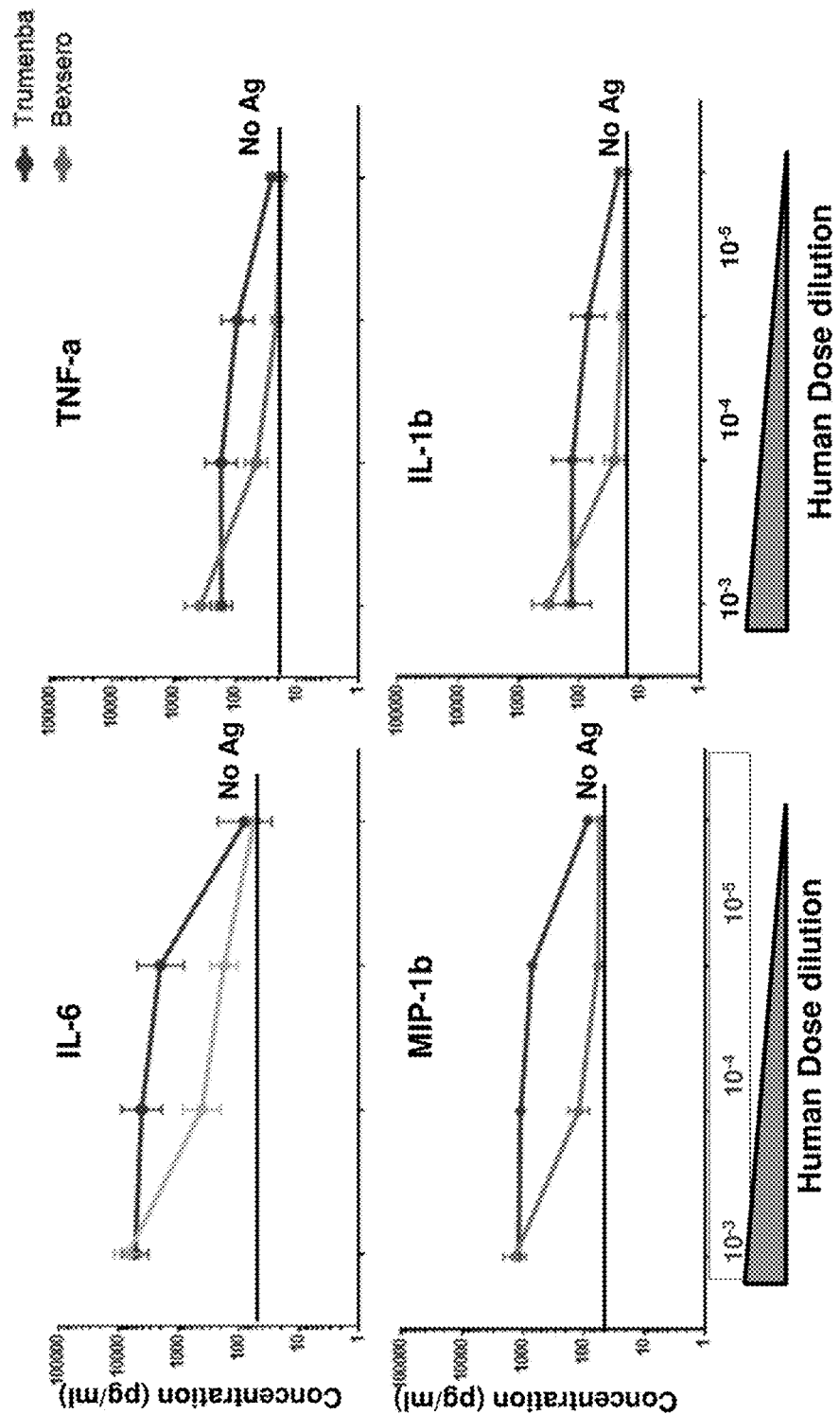
FIG. 11 represents the cytokine production (IL-6, TNFα, MIP-1β and IL-1β) of Neonate PTE derived DCs treated with different doses of BEXSERO and TRUMENBA: culture supernatants from PTE were harvested 48 hrs. post-treatment and evaluated for cytokine secretion using multiplex array, graphs represent GMV of cytokine production of IL-6, TNFα, IL-1β, and MIP-1β, in DCs. Treatments were in 10-fold dilutions of the human dose (n=20 donors).

The obtained results (FIG. 10) showed that TRUMENBA exhibited a stronger proinflammatory cytokine profile than BEXSERO in the adult MIMIC PTE. Also, TRUMENBA exhibited a stronger proinflammatory cytokine profile than BEXSERO in the neonate MIMIC PTE (FIG. 11).

Figure 12A:
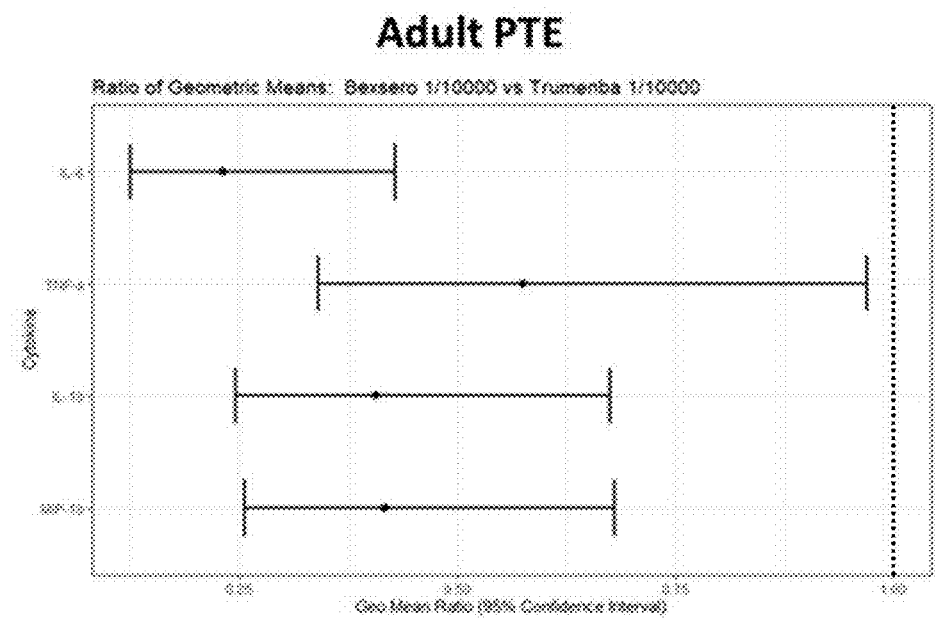
FIGS. 12A & 12B represents a Forest plot of ratio of Geometric Mean Value with 95% confidence interval of cytokine secretions triggered by BEXSERO in adult and neonate PTE over TRUMENBA at dilution of 1:10000. Dotted line is set at value of 1, value and confidence of interval below 1 means BEXSERO is inferior to TRUMENBA, and if value and interval above 1, BEXSERO is superior to the TRUMENBA.
Figure 12B:
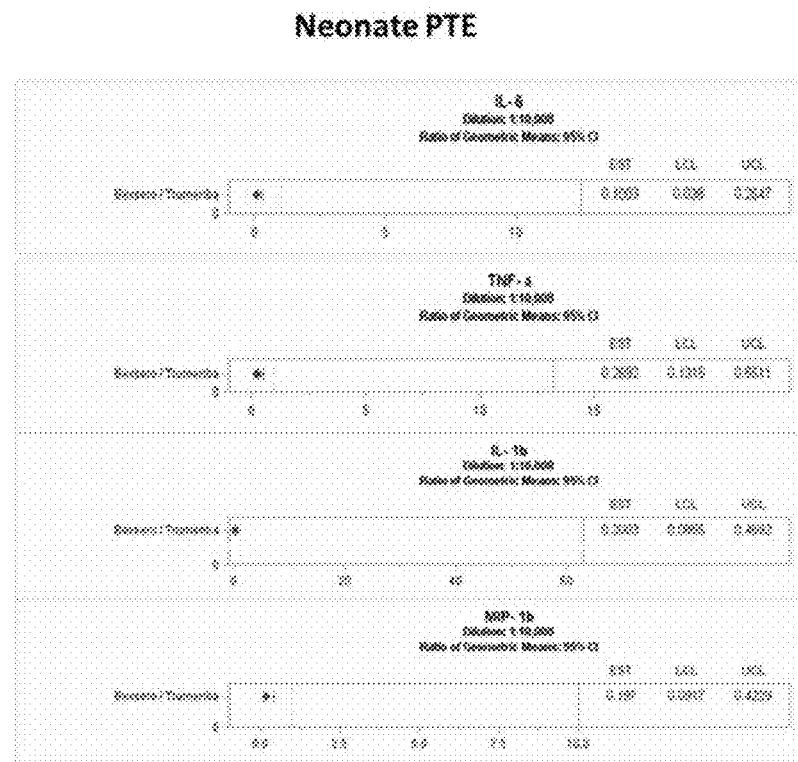

Statistical analysis as presented on FIG. 12 confirmed observations that TRUMENBA generated stronger responses than BEXSERO in adult and neonate platforms for most cytokines. Indeed, as shown by the Forest plot ratio of geometric mean with 95% confidence interval of cytokine secretions triggered by BEXSERO in adult and neonate PTE over TRUMENBA, BEXSERO is inferior to TRUMENBA.

2. F1, F2, F3, F4, F5 and BEXSERO in Adult and Neonate MIMIC PTE

Culture supernatants from untreated and treated adult and neonate MIMIC PTE cultures were harvested after 48 hours and analyzed for cytokine/chemokine secretion using a Millipore custom multiplex array. The innate chemokines/cytokines IL-6, TNFα, MIP-1β and IL-1β were included in this analysis since they are critical for innate immune activity and can also drive immune-cytotoxicity.

Figure 13:
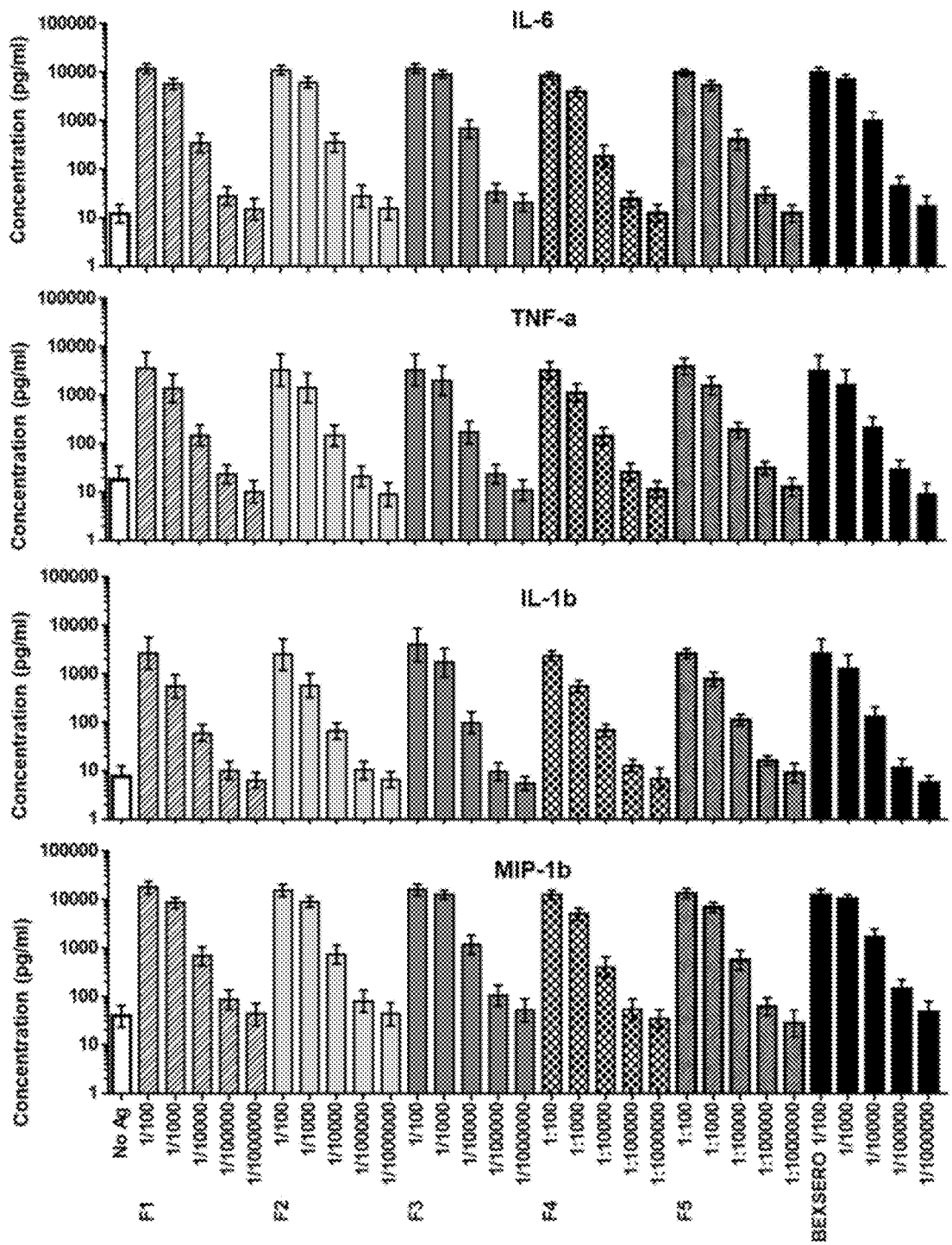
FIG. 13 represents the cytokine (IL-6, TNFα, MIP-1β and IL-1β) secretion induced by F1-F5 formulations in the adult PTE module. The MIMIC adult PTE was treated with different doses of F1-F5 formulations and control (BEXSERO). Thereafter, culture supernatants were collected and evaluated for the secretion of cytokines via multiplex array. Mean value±95% Cl of IL-6, TNFα, IL-1β, and MIP-1β; n=16 to 24.

In the adult MIMIC PTE system (see FIG. 13), all the tested formulations produced about one log higher cytokine secretion than the mock control (i.e., without antigen) at the highest treatment doses (1:100, 1:1000, 1:10000). In almost all cases the formulations tracked equal to, or slightly lower than, BEXSERO.

Figure 14A:
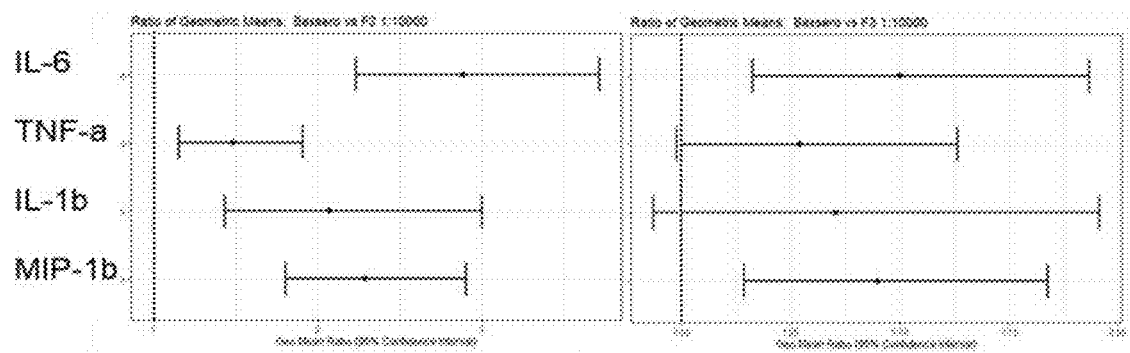
FIGS. 14A, 14B & 14C represent a Forest plot of Ratio of Geometric Mean with 95% confidence interval of cytokine secretions induced by BEXSERO over formulations F1, F2, F3, F4, and F5 in adult PTE at dilution of 1:10000. Dotted line is set at value of 1, value and confidence of interval below 1 means BEXSERO is inferior to the treatment, and if value and interval above 1, BEXSERO is superior to the treatment.
Figure 14B:
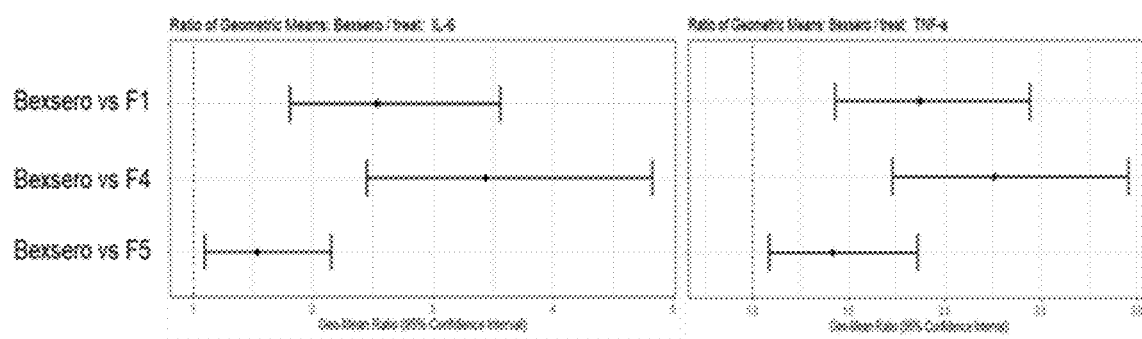
Figure 14C:
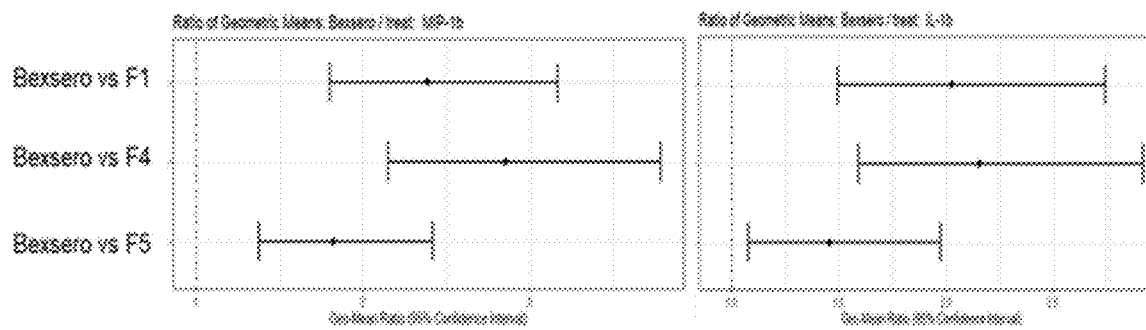

In FIGS. 14A, 14B & 14C, statistical analyses showed that, for all of cytokines reported, the F1, F2, F4, and F5 formulations generated less inflammatory responses than BEXSERO in the adult MIMIC PTE. The F3 formulation induced similar (TNF-α or IL-1β) or less (IL6 or MIP-1b) secretions of pro-inflammatory cytokines than Bexsero in the adult MIMIC PTE system.

Figure 15:
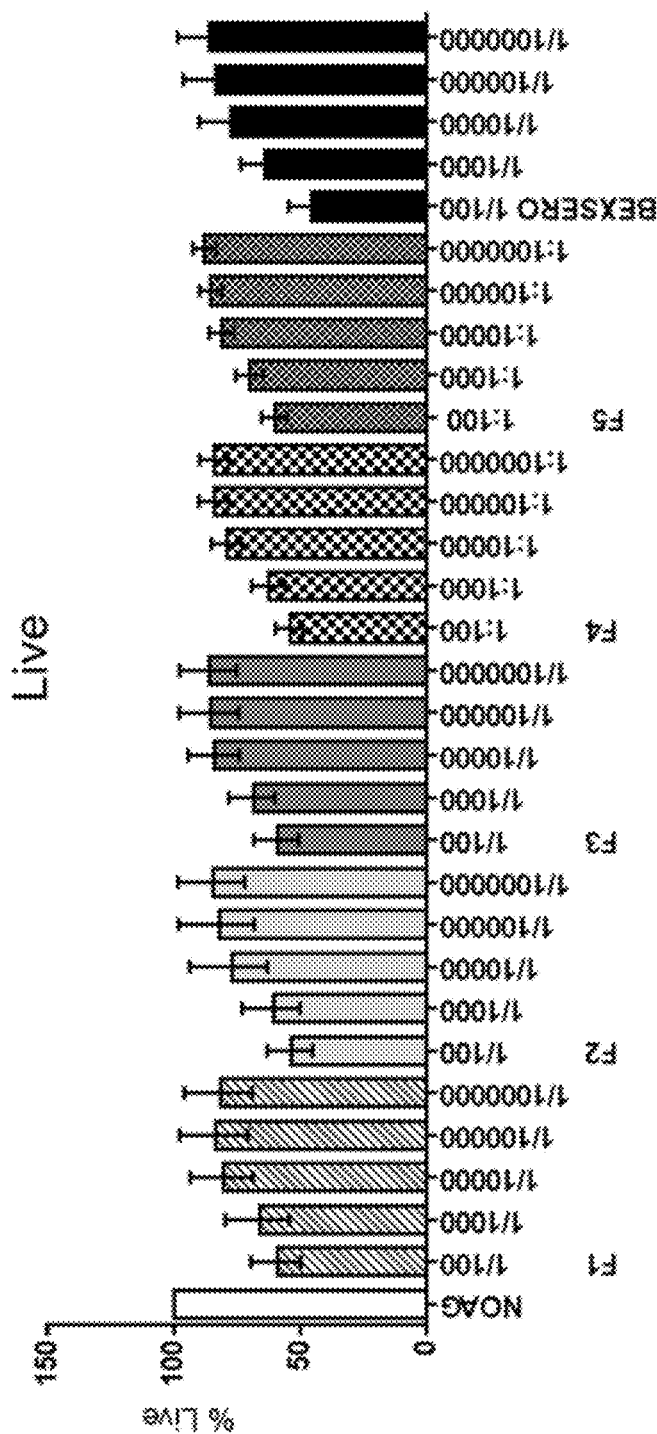
FIG. 15 represent the immunocytotoxicity (or percentage of living cells after treatment) following treatment with the F1-F5 formulations, and BEXSERO in the adult MIMIC PTE.

Furthermore, all formulations exhibited immunocytotoxicity in a dose-dependent fashion and in a range similar to BEXSERO in the adult PTE model. Indeed, as shown in FIG. 15, cell viability was nearly unimpacted at the lowest treatment doses (1:100000 and 1:000000 dilutions) and was reduced by up to approximately 50% at the highest dose (1:100 dilution) in some test conditions.

Figure 16:
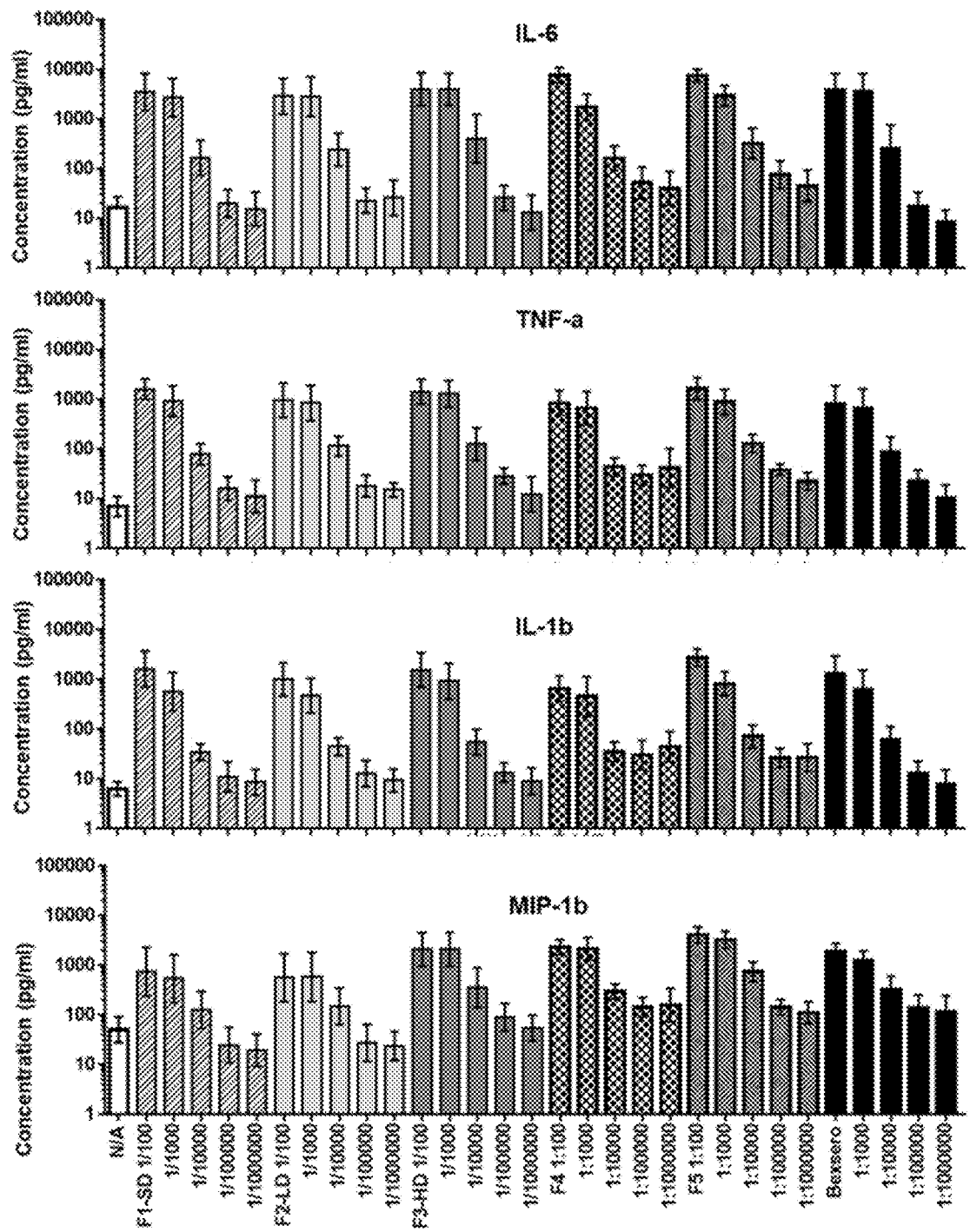
FIG. 16 represents the increase of cytokine (IL-6, TNFα, MIP-1β and IL-1β) secretion levels of F1-F5 formulations compared to BEXSERO in the neonate PTE module. The MIMIC neonate PTE was treated with different doses of F1-F5 formulations and control (BEXSERO). Thereafter, culture supernatants were collected and evaluated for the secretion of cytokines via multiplex array. Mean±95% Cl of IL-6, TNFα, IL-1b, and MIP-1b (n=16 to 24). N/A is mock control with no antigen.

Also, in the neonate MIMIC PTE, the F1, F2, F3, F4, and F5 formulations exhibited proinflammatory cytokine profiles in line with BEXSERO (FIG. 16). All formulations produced about 4-fold to one log higher cytokine secretion relative to the mock condition. The F1, F2, F3, and F4 formulations induced similar or less IL-6 and TNF-α secretion than BEXSERO. The F5 formulation induced slightly higher proinflammatory cytokine secretion than BEXSERO.

Figure 17A:
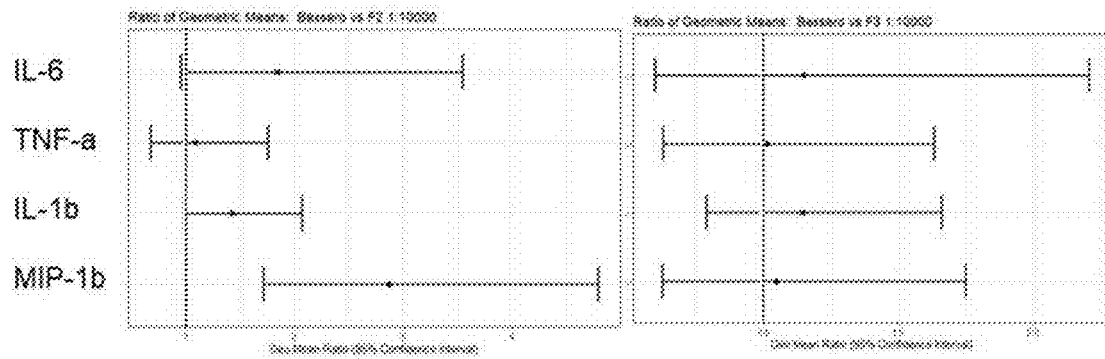
FIGS. 17A & 17B represent a Forest plot of Ratio of Geometric Mean with 95% confidence interval of cytokine secretions induced by BEXSERO over formulations F1, F2, F3, F4, and F5 in neonate PTE at dilution of 1:10000. Dotted line is set at value of 1, value and confidence of interval below 1 means Bexsero® is inferior to treatment, and if value and interval above 1, Bexsero® is superior to the treatment.
Figure 17B:
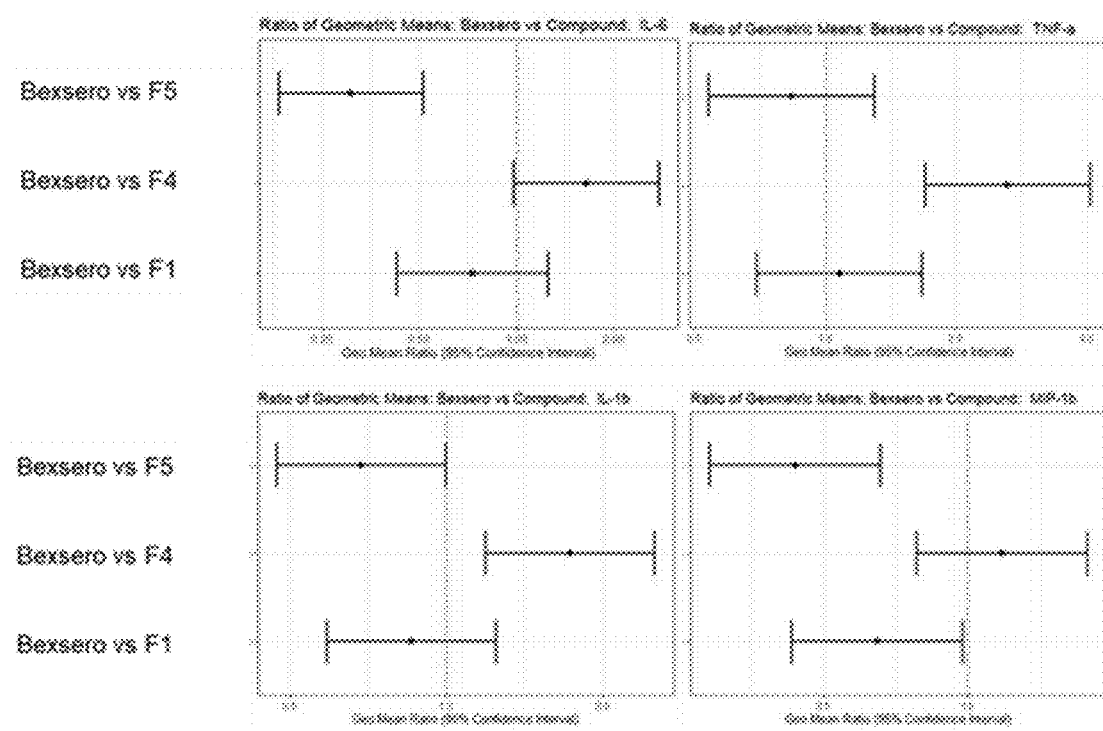

On FIGS. 17A & 17B, statistical analysis showed that, overall, the F1, F2 and F3 formulations generated inflammatory responses that were comparable to BEXSERO in the neonate MIMIC PTE. The F5 formulation tended to generate slightly higher inflammatory responses than BEXSERO in the neonate MIMIC PTE, while the F4 formulation tended to generate weaker responses than BEXSERO in the neonate MIMIC PTE.

Figure 18:
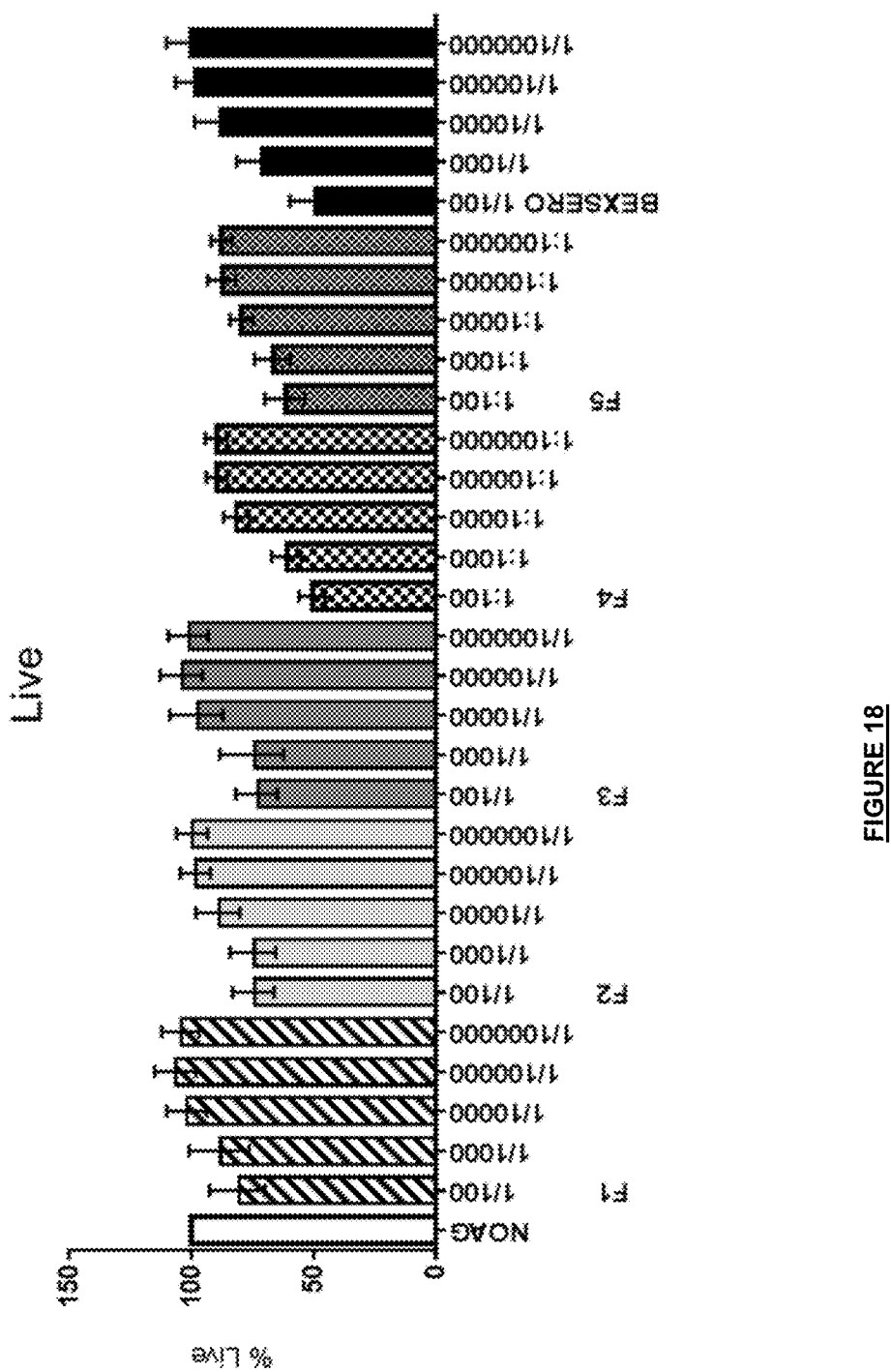
FIG. 18 represent the immunocytotoxicity (or percentage of living cells after treatment) following treatment with the F1-F5 formulations, and BEXSERO in the neonate MIMIC PTE.

Similarly to the adult MIMIC PTE system, all formulations exhibited immunocytotoxicity profiles that were similar to BEXSERO. Indeed, as shown on FIG. 18, cell viability was nearly unimpacted at the lowest treatment doses (1:100000 and 1000000 dilutions) and was reduced by up to ~50% at the highest dose (1:100 dilution) in some test conditions in the MIMIC neonate PTE.

3. Conclusions

TRUMENBA induced a stronger pro-inflammatory cytokine response than BEXSERO in both adult and neonate versions of the MIMIC PTE.

The F1, F2, F3, F4, and F5 formulations generated similar or less secretion of pro-inflammatory cytokines than BEXSERO in the adult MIMIC PTE construct.

Overall, the F5 formulation induced more proinflammatory cytokines than BEXSERO in the neonate MIMIC PTE, while the F1, F2, F3 and F4 formulations induced similar or lower cytokine responses.

The F1, F2, F3, F4 and F5 formulations had minimal effects on cell viability viability (except at dilution of 1:100 where some formulations induced ~ 40% reduction in cell viability) and trended similarly to BEXSERO.

Example 4: General Conclusion

From the above presented results, it can be concluded that the disclosed immunogenic compositions comprising a combination of meningococcal antigens which comprises at least one factor H binding protein (fHBP) A protein, at least one fHBP B protein, at least one *Neisseria* adhesin A (NadA) protein, and at least one detergent-extracted Outer Membrane Vesicle (dOMV) is able to induce an immunogenic protective response as evidenced by the hSBA results. This confirms the usefulness of those compositions as vaccine and for inducing immunogenic protective response against meningococcal infection.

Furthermore, the data shows that the breadth of prevalent and hypervirulent MenB strains coverage is larger than the ones of TRUMENBA and BEXSERO and that it allows to fill some gaps left by those two vaccines.

Finally, the data shows that those compositions present a good safety profile, present a similar or less reactogenic profile than BEXSERO which is already less reactogenic than TRUMENBA.

REFERENCES

Atkinson B, Gandhi A, Balmer P. History of Meningococcal Outbreaks in the United States: Implications for Vaccination and Disease Prevention. *Pharmacotherapy*. 2016; 36(8):880-92.

Ausubel F M, Brent R, Kingston R E, Moore D M, Short Protocols in Molecular Biology: A Compendium of Methods from Current Protocols in Molecular Biology, John Wiley & Sons, ISBN: 047132938X; 4th edition (April 1999)

Bambini S, Muzzi A, Olcen P, Rappuoli R, Pizza M, Comanducci M. Distribution and genetic variability of three vaccine components in a panel of strains representative of the diversity of serogroup B meningococcus. *Vaccine*. 2009; 27(21):2794-803.

Batista R S, Gomes A P, Dutra Gazineo J L, Balbino Miguel P S, Santana L A, Oliveira L, et al. Meningococcal disease, a clinical and epidemiological review. *Asian Pac J Trop Med*. 2017; 10(11):1019-29.

Bijlsma M W, Brouwer M C, Spanjaard L, van de Beek D, van der Ende A. A decade of herd protection after introduction of meningococcal serogroup C conjugate vaccination. *Clin Infect Dis*. 2014; 59(9):1216-21.

Borrow R, Alarcon P, Carlos J, Caugant D A, Christensen H, Debbag R, et al. The Global Meningococcal Initiative: global epidemiology, the impact of vaccines on meningococcal disease and the importance of herd protection. *Expert Rev Vaccines*. 2017; 16(4):313-28.

Borrow R, Balmer P, Miller E. Meningococcal surrogates of protection—serum bactericidal antibody activity. *Vaccine*. 2005; 23(17-18):2222-7.

Borrow R, Carlone G M, Rosenstein N, Blake M, Feavers I, Martin D, et al. *Neisseria meningitidis* group B correlates of protection and assay standardization—international meeting report Emory University, Atlanta, Ga., United States, 16-17 Mar. 2005. Vaccine. 2006; 24(24):5093-107.

Bruce M G, Rosenstein N E, Capparella J M, Shutt K A, Perkins B A, Collins M. Risk factors for meningococcal disease in college students. *JAMA*. 2001; 286(6):688-93.

Brunelli B, Del Tordello E, Palumbo E, Biolchi A, Bambini S, Comanducci M, et al. Influence of sequence variability on bactericidal activity sera induced by Factor H binding protein variant 1.1. *Vaccine*. 2011; 29(5):1072-81.

Campsall P A, Laupland K B, Niven D J. Severe meningococcal infection: a review of epidemiology, diagnosis, and management. *Crit Care Clin*. 2013; 29(3):393-409.

Capecchi B A-B J, Di Marcello F, Ciucchi L, Masignani V, Taddei A, Rappuoli R, Pizza M, Arico B. *Neisseria meningitides* NadA is a new invasin which promotes bacterial adhesion to and penetration into human epithelial cells. *Mol. Microbiol.* 2005; 55:(687-98).

Caron F, du Chatelet I P, Leroy J P, Ruckly C, Blanchard M, Bohic N, et al. From tailor-made to ready-to-wear meningococcal B vaccines: longitudinal study of a clonal meningococcal B outbreak. *Lancet Infect Dis.* 2011; 11(6):455-63.

Chang H Y ea. Distribution of *Neisseria meningitidis* serogroup b (NmB) vaccine antigens in meningococcal disease causing isolates in the United States during 2009-2014, prior to NmB vaccine licensure. *J Infect* 2019; S0163-4453(19):30272-5.

Christensen H, May M, Bowen L, Hickman M, Trotter C L. Meningococcal carriage by age: a systematic review and meta-analysis. *Lancet Infect Dis.* 2010; 10(12): 853-61.

Costa I, Pajon R, Granoff D M. Human factor H (F H) impairs protective meningococcal anti-FHbp antibody responses and the antibodies enhance F H binding. *mBio.* 2014; 5(5):e01625-14.

Dyet K H, Martin D R. Clonal analysis of the serogroup B meningococci causing New Zealand's epidemic. *Epidemiol Infect.* 2006; 134(2):377-83.

Einhorn M S, Weinberg G A, Anderson E L, Granoff P D, Granoff D M. Immunogenicity in infants of *Haemophilus influenzae* type B polysaccharide in a conjugate vaccine with *Neisseria meningitidis* outer-membrane protein. *Lancet* (London, England). 1986; 2(8502):299-302.

Folaranmi T, Rubin L, Martin S W, Patel M, MacNeil J R, Centers for Disease C. Use of Serogroup B Meningococcal Vaccines in Persons Aged>/=10 Years at Increased Risk for Serogroup B Meningococcal Disease: Recommendations of the Advisory Committee on Immunization Practices, 2015. *MMWR Morb Mortal Wkly Rep.* 2015; 64(22):608-12.

Frasch C E, Borrow R, Donnelly J. Bactericidal antibody is the immunologic surrogate of protection against meningococcal disease. *Vaccine.* 2009; 27 Suppl 2:B1112-6.

Fredriksen J H, Rosenqvist E, Wedege E, Bryn K, Bjune G, Froholm L O, et al. Production, characterization and control of MenB-vaccine "Folkehelsa": an outer membrane vesicle vaccine against group B meningococcal disease. *NIPH Ann.* 1991; 14(2):67-79; discussion –80.

Fu J, Bailey F J, King J J, Parker C B, Robinett R S, Kolodin D G, George H A, Herber W K. Recent advances in the large scale fermentation of *Neisseria meningitidis* group B for the production of an outer membrane protein complex. Biotechnology (N Y). 1995 February; 13(2):170-4. doi: 10.1038/nbt0295-170. PMID: 9634759.

Germinario C, Tafuri S, Napoli C, Montagna M T, Balducci M T, Fortunato F, et al. Young-adult carriers of *Neisseria meningitidis* in Puglia (Italy): will the pattern of circulating meningococci change following the introduction of meningococcal serogroup C conjugate vaccines? *Hum Vaccin.* 2010; 6(12):1025-7.

Giuliani M, Bartolini E, Galli B, Santini L, Lo Surdo P, Buricchi F, et al. Human protective response induced by meningococcus B vaccine is mediated by the synergy of multiple bactericidal epitopes. *Sci Rep.* 2018; 8(1):3700.

Goldschneider I, Gotschlich E C, Artenstein M S. Human immunity to the meningococcus. I. The role of humoral antibodies. *J Exp Med.* 1969; 129(6):1307-26.

Granoff D M, Ram S, Beernink P T. Does binding of complement factor H to the meningococcal vaccine antigen, factor H binding protein, decrease protective serum antibody responses? *Clin Vaccine Immunol.* 2013; 20(8):1099-107.

Grodet C, Dequin P F, Watt S, Lanotte P, de Gialluly C, Taha M K, et al. Outbreak in France of *Neisseria meningitidis* B:15:P1.12 belonging to sequence type 1403. Clin *Microbiol Infect.* 2004; 10(9):845-8.

Harrison L, Granoff D, Pollard A. Meningococcal capsular group A, C, W, and Y conjugate vaccines. [ed.] Orenstein W A, Offit P A, Edwards K M Plotkin S A. Vaccines. 7. Philadelphia (PA): Elsevier; 2018. p. 619-43.

Harrison O B, Claus H, Jiang Y, Bennett J S, Bratcher H B, Jolley K A, et al. Description and nomenclature of *Neisseria meningitidis* capsule locus. *Emerg Infect Dis.* 2013; 19(4):566-73.

Helting T B, Guthöhrlein G, Blackkolb F, Ronneberger H. Serotype determinant protein of *Neisseria Meningitidis.* Large scale preparation by direct detergent treatment of the bacterial cells. *Acta Pathol Microbiol Scand C.* 1981 April; 89(2):69-78. PMID: 6794337.

Higbee R G, Byers A M, Dhir V, Drake D, Fahlenkamp H G, Gangur J, Kachurin A, Kachurina O, Leistritz D, Ma Y, Mehta R, Mishkin E, Moser J, Mosquera L, Nguyen M, Parkhill R, Pawar S, Poisson L, Sanchez-Schmitz G, Schanen B, Singh I, Song H, Tapia T, Warren W, Wittman V. An immunologic model for rapid vaccine assessment—a clinical trial in a test tube. *Altern Lab Anim.* 2009 September; 37 Suppl 1:19-27. doi: 10.1177/026119290903701S05. PMID: 19807200.

Kvalsvig A J, Unsworth D J. The immunopathogenesis of meningococcal disease. *J Clin Pathol.* 2003; 56(6): 417-22.

Lucidarme J ea. Characterization of fHBP, nhba (gna2132), nadA, porA, and sequence type in group B meningococcal case isolates collected in England and Wales during January 2008 and potential coverage of an investigational group B meningococcal vaccine. *Clin Vaccine Immunol* 2010; 17(6):919-29.

Luna et al. "Evaluation of the innate immunostimulatory potential of originator and non-originator copies of insulin glargine in an in vitro human immune model." *PloS one,* vol. 13,6 e0197478. 6 Jun. 2018, doi: 10.1371/journal.pone.0197478

Ma Y, Poisson L, Sanchez-Schmitz G, Pawar S, Qu C, Randolph G J, Warren W L, Mishkin E M, Higbee R G. 2010. Assessing the immunopotency of Toll-like receptor agonists in an in vitro tissue-engineered immunological model. *Immunology* 130: 374-87

MacLennan J, Kafatos G, Neal K, Andrews N, Cameron J C, Roberts R, et al. Social behavior and meningococcal carriage in British teenagers. *Emerg Infect Dis.* 2006; 12(6):950-7.

Maiden M C, Ibarz-Pavon A B, Urwin R, Gray S J, Andrews N J, Clarke S C, et al. Impact of meningococcal serogroup C conjugate vaccines on carriage and herd immunity. *J Infect Dis.* 2008; 197(5):737-43.

Marshall H S, Richmond P C, Nissen M D, Jiang Q, Anderson A S, Jansen K U, et al. Safety and immunogenicity of a meningococcal B bivalent rLP2086 vaccine in healthy toddlers aged 18-36 months: a phase 1 randomized-controlled clinical trial. *Pediatr Infect Dis J.* 2012; 31(10):1061-8.

Martin D R, Walker S J, Baker M G, Lennon D R. New Zealand epidemic of meningococcal disease identified by a strain with phenotype B:4:P1.4. *J Infect Dis.* 1998; 177(2):497-500.

Martinon-Torres F, Gimenez-Sanchez F, Bernaola-Iturbe E, Diez-Domingo J, Jiang Q, Perez J L. A randomized, phase ½ trial of the safety, tolerability, and immunogenicity of bivalent rLP2086 meningococcal B vaccine in healthy infants. Vaccine. 2014; 32(40):5206-11.

McNeil L K, Zagursky R J, Lin S L, et al. Role of factor H binding protein in Neisseria meningitidis virulence and its potential as a vaccine candidate to broadly protect against meningococcal disease. Microbiol Mol Biol Rev. 2013; 77(2):234-252. doi:10.1128/MMBR.00056-12

Meri S, Jordens M, Jarva H. Microbial complement inhibitors as vaccines. Vaccine. 2008; 26 Suppl 8:I113-7.

Moro P L, Jankosky C, Menschik D, Lewis P, Duffy J, Stewart B, et al. Adverse events following Haemophilus influenzae type b vaccines in the Vaccine Adverse Event Reporting System, 1990-2013. The Journal of pediatrics. 2015; 166(4):992-7.

Murphy E, Andrew L, Lee K L, Dilts D A, Nunez L, Fink P S, et al. Sequence diversity of the factor H binding protein vaccine candidate in epidemiologically relevant strains of serogroup B Neisseria meningitidis. The Journal of infectious diseases. 2009; 200(3):379-89.

Needleman S. B. and Wunsch C. D., "A general method applicable to the search of similarities in the amino acid sequence of two proteins" Journal of Molecular Biology, 1970, pages 443-53, volume 48

Pace D, Pollard A J. Meningococcal disease: clinical presentation and sequelae. Vaccine. 2012; 30 Suppl 2:B3-9.

Pagotto F J, Salimnia H, Totten P A, Dillon J R. Stable shuttle vectors for Neisseria gonorrhoeae, Haemophilus spp. and other bacteria based on a single origin of replication. Gene. 2000 Feb. 22; 244(1-2):13-9. doi: 10.1016/s0378-1119(99)00557-0. PMID: 10689182.

Pizza M, Scarlato V, Masignani V, Giuliani M M, Arico B, Comanducci M, et al. Identification of vaccine candidates against serogroup B meningococcus by whole-genome sequencing. Science. 2000; 287(5459):1816-20.

Pollard A J. Global epidemiology of meningococcal disease and vaccine efficacy. Pediatr Infect Dis J. 2004; 23(12 Suppl):S274-9.

Rodriguez A P, Dickinson F, Baly A, Martinez R. The epidemiological impact of antimeningococcal B vaccination in Cuba. Mem Inst Oswaldo Cruz. 1999; 94(4):433-40.

Rouphael N G, Stephens D S. Neisseria meningitidis: biology, microbiology, and epidemiology. Methods Mol Biol. 2012; 799:1-20.

Seib K L S M, Comanducci M, Toneatto D, Masignani V. Neisseria meningitidis factor H-binding protein fHBP: a key virulence factor and vaccine antigen. Expert Rev Vaccines. 2015; 14(6):841-59.

Stephens D S, Apicella M A. Neisseria meningitidis. [ed.] J. E. Bennett, R. Dolin and M. J. Blaser. Philadelphia: Elsevier Saunders; 2015. p. 2425-45.

Stephens D S. Biology and pathogenesis of the evolutionarily successful, obligate human bacterium Neisseria meningitidis. Vaccine. 2009; 27 Suppl 2:B71-7.

Syed Y Y. DTaP5-HB-IPV-Hib Vaccine (Vaxelis®): A Review of its Use in Primary and Booster Vaccination. Paediatric drugs. 2017; 19(1):69-80.

Trotter C L, Andrews N J, Kaczmarski E B, Miller E, Ramsay M E. Effectiveness of meningococcal serogroup C conjugate vaccine 4 years after introduction. Lancet. 2004; 364(9431):365-7.

U.S. Pat. No. 10,300,122—Novel immunogenic compositions for the prevention and treatment of meningococcal disease U.S. Pat. No. 10,625,025—Prefilled syringe U.S. Pat. No. 10,695,505—Dual-chamber syringe U.S. Pat. No. 11,077,180 B2—Non-lipidated variants of Neisseria meningitidis ORF2086 antigens U.S. Pat. No. 4,695,624—Covalently-modified polyanionic bacterial polysaccharides, stable covalent conjugates of such polysaccharides and immunogenic proteins with bigeneric spacers, and methods of preparing such polysaccharides and conjugates and of confirming covalency U.S. Pat. No. 5,494,808—Defined medium OMPC fermentation process U.S. Pat. No. 9,724,402 B2—Neisseria meningitidis compositions and methods thereof Vu D M, Wong T T, Granoff D M. Cooperative serum bactericidal activity between human antibodies to meningococcal factor H binding protein and neisserial heparin binding antigen. Vaccine. 2011; 29(10):1968-73.

Vuocolo S, Balmer P, Gruber W C, Jansen K U, Anderson A S, Perez J L, et al. Vaccination strategies for the prevention of meningococcal disease. Hum Vaccin Immunother. 2018; 14(5):1203-15.

Wang X, Cohn A, Comanducci M, Andrew L, Zhao X, MacNeil J R, et al. Prevalence and genetic diversity of candidate vaccine antigens among invasive Neisseria meningitidis isolates in the United States. Vaccine. 2011; 29(29-30):4739-44.

WO 2001/064920—Hybrid expression of neisserial proteins

WO 2001/064922—Heterologous expression of neisserial proteins

WO 2002/058737—Multivalent meningococcal polysaccharide-protein conjugate vaccine WO 2003/020756—Hybrid and tandem expression of neisserial proteins WO 2009/109550—Process for stabilizing an adjuvant containing vaccine composition WO 2010/046715—Vaccine compositions comprising a mutated factor h binding protein WO 2011/126863—Factor H binding proteins (FHBP) with altered properties and methods of use thereof WO 2013/046855—Liquid injector WO 2015/017817—Non-naturally occurring factor H binding proteins (fHBP) and methods of use thereof WO 2015/128480—Modified meningococcal fhbp polypeptides WO 2016/008960—Modified meningococcal fhbp polypeptides WO 2016/014719—Factor h binding protein variants and methods of use thereof WO 2018/045286—Neisseria meningitidis vaccine

The invention claimed is:

1. A vaccine comprising an immunogenic composition comprising a combination of *Neisseria meningitidis* serogroup B antigens, said combination consisting of:
   (i) a 25 to 100 µg/dose of at least one non-lipidated factor H binding protein (fHBP) A protein comprising at least about 85% identity with SEQ ID NO: 1 and comprising at least the amino acid substitution G220S based on the numbering of SEQ ID NO: 6;
   (ii) a 25 to 100 µg/dose of at least one non-lipidated fHBP B protein consisting of SEQ ID NO: 4, with the proviso that the N-terminal cysteine of SEQ ID NO: 4 is removed or substituted with another amino acid;
   (iii) a 25 to 100 µg/dose of at least one *Neisseria* adhesin A (NadA) protein consisting of SEQ ID NO: 5; and
   (iv) a 20 to 150 µg/dose of at least one detergent-extracted Outer Membrane Vesicle (dOMV) from a MenB strain expressing PorA,
   wherein the vaccine further comprises 100 to 600 µg/dose of aluminum phosphate adjuvant, and 50 mM acetate buffer, wherein the composition has a pH of 6.0.

2. The vaccine according to claim 1, further comprising a combination of MenA, MenC, MenW-135 and MenY capsular polysaccharides each conjugated to a tetanus toxoid carrier protein, wherein the MenA polysaccharide is conjugated to the tetanus toxoid carrier via an adipic acid dihydrazide (ADH) linker while the MenC, MenW-135 and MenY polysaccharides are each directly conjugated to the tetanus toxoid carrier.

3. The composition according to claim 1, wherein the dOMV comprises a PorA VR2 subtype.

4. The composition according to claim 1, wherein the dOMV comprises a PorA VR2 P1.2.

5. The vaccine according to claim 1, wherein the fHBP A protein is present in an amount ranging from about 75 µg/dose to about 100 µg/dose, or at about 25 µg/dose, or at about 50 µg/dose, or at about 100 µg/dose.

6. The vaccine according to claim 2, wherein the fHBP A protein is present in an amount ranging from about 75 µg/dose to about 100 µg/dose, or at about 25 µg/dose, or at about 50 µg/dose, or at about 100 µg/dose.

7. The vaccine according to claim 1, wherein the fHBP B protein is present in an amount ranging from about 75 µg/dose to about 100 µg/dose, or at about 25 µg/dose, or at about 50 µg/dose, or at about 100 µg/dose.

8. The vaccine according to claim 2, wherein the fHBP B protein is present in an amount ranging from about 75 µg/dose to about 100 µg/dose, or at about 25 µg/dose, or at about 50 µg/dose, or at about 100 µg/dose.

9. The vaccine according to claim 1, wherein the NadA protein is present in an amount ranging from about 75 µg/dose to about 100 µg/dose, or at about 25 µg/dose, or at about 50 µg/dose, or at about 100 µg/dose.

10. The vaccine according to claim 2, wherein the NadA protein is present in an amount ranging from about 75 μg/dose to about 100 μg/dose, or at about 25 μg/dose, or at about 50 μg/dose, or at about 100 μg/dose.

11. The vaccine according to claim 1, wherein the dOMV is present in an amount ranging from about 100 μg/dose to about 150 μg/dose, or from about 110 μg/dose to about 125 μg/dose, or at about 25 μg/dose, or at about 50 μg/dose, or at about 125 μg/dose.

12. The vaccine according to claim 2, wherein the dOMV is present in an amount ranging from about 100 μg/dose to about 150 μg/dose, or from about 110 μg/dose to about 125 μg/dose, or at about 25 μg/dose, or at about 50 μg/dose, or at about 125 μg/dose.

13. The vaccine according to claim 1, wherein the aluminum phosphate adjuvant is present in an amount ranging from about 300 μg/dose to about 600 μg/dose, or from about 350 μg/dose to about 550 μg/dose, or from about 400 μg/dose to about 500 μg/dose.

14. The vaccine according to claim 2, wherein the aluminum phosphate adjuvant is present in an amount ranging from about 300 μg/dose to about 600 μg/dose, or from about 350 μg/dose to about 550 μg/dose, or from about 400 μg/dose to about 500 μg/dose.

15. The vaccine according to claim 2, wherein the non-lipidated factor H binding protein (fHBP) A protein consists of SEQ ID NO:2, with the proviso that the N-terminal cysteine of SEQ ID NO: 2 is removed or substituted with another amino acid.

\* \* \* \* \*